US012636342B2

(12) United States Patent
Kim et al.

(10) Patent No.: US 12,636,342 B2
(45) Date of Patent: May 26, 2026

(54) **TARS DERIVED FROM *AKKERMANSIA MUCINIPHILA* OR FRAGMENT THEREOF, AND USE THEREOF**

(71) Applicants: KOREA RESEARCH INSTITUTE OF BIOSCIENCE AND BIOTECHNOLOGY, Daejeon (KR); SEOUL NATIONAL UNIVERSITY R&DB FOUNDATION, Seoul (KR)

(72) Inventors: Myung Hee Kim, Daejeon (KR); Won-Jae Lee, Seoul (KR); Su-Man Kim, Daejeon (KR); Shinhye Park, Daejeon (KR); Kyung-Ah Lee, Seoul (KR); Eun-Young Lee, Daejeon (KR); Byoung Chan Kim, Daejeon (KR); Chul-Ho Lee, Daejeon (KR); Jungwon Hwang, Daejeon (KR)

(73) Assignees: KOREA RESEARCH INSTITUTE OF BIOSCIENCE AND BIOTECHNOLOGY, Daejeon (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 65 days.

(21) Appl. No.: 17/952,990

(22) Filed: Sep. 26, 2022

(65) Prior Publication Data

US 2023/0024893 A1 Jan. 26, 2023

Related U.S. Application Data

(63) Continuation-in-part of application No. PCT/KR2021/003720, filed on Mar. 25, 2021.

(30) Foreign Application Priority Data

Mar. 25, 2020 (KR) ........................ 10-2020-0036379

(51) Int. Cl.
*A61K 38/16* (2006.01)
*A61K 38/53* (2006.01)
*A61P 29/00* (2006.01)

(52) U.S. Cl.
CPC ............ *A61K 38/164* (2013.01); *A61K 38/53* (2013.01); *A61P 29/00* (2018.01); *C12Y 601/01003* (2013.01)

(58) Field of Classification Search
None
See application file for complete search history.

(56) References Cited

FOREIGN PATENT DOCUMENTS

| | | | |
|---|---|---|---|
| KR | 10-2015-0093711 A | 8/2015 |
| KR | 10-2016-0140565 A | 12/2016 |
| KR | 10-2018-0011130 A | 1/2018 |
| WO | 2017/060698 A1 | 4/2017 |

OTHER PUBLICATIONS

Chelakkot et al (Exp. Mol. Med., 50, e450, 1-11, 2018).*
International Search Report dated Jul. 21, 2021 for corresponding International Patent Application No. PCT/KR2021/003720, 11 pages.
Written Opinion dated Jul. 21, 2021 for corresponding International Patent Application No. PCT/KR2021/003720, 5 pages.
Wang et al., "T regulatory cells and B cells cooperate to form a regulatory loop that maintains gut homeostasis and suppresses dextran sulfate sodium-induced colitis," Mucosal Immunology, Mar. 25, 2015, pp. 1297-1312, vol. 8, No. 6.
NCBI, Genbank accession No. ACD05550.1, "threonyl-tRNA synthetase[Akkermansia muciniphila ATCC BAA-835]," Dec. 11, 2013, 3 pages.
Hae Jun Kim, "Pro-inflammatory function of secreted threonyl-tRNA synthetase," Thesis, Seoul National University, 2016, pp. 1-35.

* cited by examiner

*Primary Examiner* — Brian Gangle
(74) *Attorney, Agent, or Firm* — Hauptman Ham, LLP

(57) ABSTRACT

The present invention relates to uses of threonyl-tRNA synthetase (TARS) derived from *Akkermansia muciniphila* or a fragment thereof as an active ingredient for prevention, alleviation, and treatment of an inflammatory disease. The *Akkermansia muciniphila* TARS or a fragment thereof according to the present invention promotes the differentiation of M2 macrophages, which are anti-inflammatory macrophages, to multiply macrophages, thereby increasing the secretion of IL-10 as an anti-inflammatory cytokine, leading to the proliferation of B cells to result in an anti-inflammatory effect, and thus was verified to show alleviation effects of not only inflammatory diseases but also immune diseases, infectious diseases, and metabolic diseases accompanied by inflammation, and to have excellent effects in the prevention or treatment of an inflammatory bowel disease (IBD).

6 Claims, 36 Drawing Sheets

Specification includes a Sequence Listing.

• DLS: 30~100 nm (Avr 42 nm)          • TEM

FIG. 2

- Mouse adipocyte (3T3-L1)

* AmTARS 24 h incubation

- Insulin signaling pathway

- Peptide activity

- U2(R2) activity

FIG. 26

TARS DERIVED FROM *AKKERMANSIA MUCINIPHILA* OR FRAGMENT THEREOF, AND USE THEREOF

CROSS-REFERENCE TO RELATED APPLICATION

This application is a continuation-in-part of International Application No. PCT/KR2021/003720 filed on Mar. 25, 2021 which is based upon and claims the benefit of priority to Korean Patent Application No. 10-2020-0036379 filed on Mar. 25, 2020, in the Korean Intellectual Property Office, both of which are incorporated herein by reference in their entireties.

INCORPORATION BY REFERENCE

The sequence listing of the present application is submitted electronically via EFS-Web herewith as an ASCII formatted sequence listing with a file name "F-04-5900-0030_Sequence_Listing_Amended_CRF2.txt", with a creation date of May 10, 2025, and a size of 15,542 bytes. This sequence listing submitted via EFS-Web is part of the specification and is herein incorporated by reference in its entirety.

TECHNICAL FIELD

The present invention relates to use of *Akkermansia muciniphila*-derived threonyl-tRNA synthetase (TARS) or a fragment thereof as an active ingredient for prevention, alleviation, and treatment of an inflammatory disease.

BACKGROUND ART

Toll-like receptors (TLRs), cell membrane receptors that have an important role in human innate immunity, induce an inflammatory or anti-inflammatory immune response by recognizing a pathogen-associated molecular pattern (PAMP) derived from microbes and activating cell signaling through adaptor proteins. TLRs are expressed in various species and various cells, and 10 types of TLRs have been known to be expressed in humans. Of these, TLR2 perform functions by forming heterodimers with TLR1, TLR6, and TLR10. These mainly recognize cell wall components (lipoproteins, lipoteichoic acid, zymosan, etc.) of pathogens. When a ligand is recognized by TLR2, inflammatory transcription factors, such as nuclear factor kappa-light-chain-enhancer of activated B cells (NF-kB) and activator protein 1 (AP-1), are activated by myeloid differentiation primary response gene 88 (MyD88) and MyD88 adapter-like (MAL)/Toll/interleukin-1 receptor domain-containing adapter protein (TIRAP)-dependent signaling and the production of anti-inflammatory cytokines are introduced through phosphatidylinositol-3-kinase (PI3K)/protein kinase B (AKT) signaling. TLR2 is also known to have an important role in the regulation of macrophage differentiation.

Macrophages initiate inflammatory responses in response to pathogens or harmful stimulations caused by apoptosis and necrosis. Macrophages are activated through downstream signaling of TLR and cytokine receptors. The activated macrophages cause the production of inflammatory cytokines and chemokines, migration of cells, and removal of harmful substances by transcriptional and epigenetic changes. In the late stage of inflammation, macrophages contribute to the prevention of sustained inflammatory responses causing tissue injury and eliminate inflammation.

Macrophages are classified into functional phenotypes M1 and M2 macrophages according to the intracellular microenvironment, wherein M1 macrophage polarization is accelerated by interferon-γ, lipopolysaccharide (LPS), inflammatory cytokines, or the like, and M2 macrophage polarization is accelerated by interleukin (IL)-4, IL-13 cytokines, or the like. M1 macrophages mainly secrete inflammatory cytokines and chemokines, such as IL-6, IL-12, and tumor necrosis factor (TNF)-α, while M2 macrophages secrete anti-inflammatory cytokines, such as arginase-I, IL-10, and transforming growth factor (TGF)-β, to reduce inflammation and inhibit immune responses. In particular, IL-10 secreted by M2 macrophages is known to be a very important cytokine in the inhibition of inflammatory responses and is also reported to increase the proliferation and viability of B cells. B cells are very well known to have a core role in the regulation of immune responses through antibody production, and a previous study has reported that B cells, together with regulatory T cells, are essential for inhibiting the inflammatory response in inflammatory bowel disease (IBD) (L Wang, et al., T regulatory cells and B cells cooperate to form a regulatory loop that maintains gut homeostasis and suppresses dextran sulfate sodium-induced colitis, *Mucosal Immunol.* 2015, 8(6): 1297-312).

Aminoacyl-tRNA synthetase (AARS) is an enzyme that attaches an amino acid to transport RNA (RNA) in the early stages of protein synthesis. Some of the human-derived AARS proteins are known to be secreted from cells to perform various functions. Typically, it is known that in a specific environment, human tyrosyl-tRNA synthetase (YARS) is secreted from cells to perform a function as a cytokine, and human lysyl-tRNA synthetase (KARS) stimulates immune cells to promote the inflammatory response. In particular, it has been reported that human threonyl-tRNA synthetase (TARS), when secreted from cells, induces angiogenesis via an inflammatory signal and, in pancreatic cancer cells, increases the synthesis of mucin 1 (MUC1), one of the major proteins of mucin, containing a large amount of threonine. Additionally, TARS has been reported as a key component of vertebrate-specific protein synthesis initiation complexes needed for protein synthesis of genes necessary for development of blood vessels, the nervous system, and the like during the evolution from invertebrates to vertebrates.

DISCLOSURE

Technical Problem

On the basis of the functions of human AARSs after being secreted from cells, the present inventors confirmed that *Akkermansia muciniphila*, a gut microbe that has been reported to have an important role in metabolic diseases through human immune regulation, specifically secretes TARS, wherein the TARS activates B cells by promoting IL-10 secretion of macrophages, thereby inducing anti-inflammatory immune homeostasis, and thus confirmed that TARS has efficacy of preventing, alleviating, and treating inflammatory diseases via macrophages.

Technical Solution

An aspect of the present invention is to provide a pharmaceutical composition for prevention or treatment of an inflammatory disease, the pharmaceutical composition containing *Akkermansia muciniphila*-derived threonyl-tRNA synthetase (TARS) or a fragment thereof as an active ingredient.

Another aspect of the present invention is to provide a method for preventing or treating an inflammatory disease, the method including administering to a subject a composition containing *Akkermansia muciniphila*-derived TARS or a fragment thereof as an active ingredient.

Still another aspect of the present invention is to provide a composition for proliferation of B cells, the composition containing *Akkermansia muciniphila*-derived TARS or a fragment thereof as an active ingredient.

Still another aspect of the present invention is to provide a composition for proliferation of macrophages, the composition containing *Akkermansia muciniphila*-derived TARS or a fragment thereof as an active ingredient.

Still another aspect of the present invention is to provide a composition for differentiation of M2 macrophages, the composition containing *Akkermansia muciniphila*-derived TARS or a fragment thereof as an active ingredient.

Still another aspect of the present invention is to provide a quasi-drug for prevention or alleviation of an inflammatory disease, the quasi-drug containing *Akkermansia muciniphila*-derived TARS or a fragment thereof as an active ingredient.

Advantageous Effects

The *Akkermansia muciniphila* TARS or a fragment thereof according to the present invention increases the secretion of the anti-inflammatory cytokine IL-10 by promoting the differentiation of M2 macrophages, anti-inflammatory macrophages, to induce the proliferation of macrophages, and thus exhibits an anti-inflammatory effect through the proliferation of B cells, and therefore exhibits an effect of alleviating not only an inflammatory disease but also an immune disease, an infectious diseases, and a metabolic disease, which are accompanied by inflammation, and especially, has an excellent effect in the prevention or treatment of inflammatory bowel disease (IBD) or the like.

BRIEF DESCRIPTION OF DRAWINGS

FIG. 2 shows the results of analyzing cytokine expression in BMDM and THP1 cells according to AmTARS (*Akkermansia muciniphila*-derived TARS) treatment.

4 alanyl-tRNA synthetase beta subunit; AmGARS, glycyl-tRNA synthetase; AmHARS, histidyl-tRNA synthetase; AmIARS, isoleucyl-tRNA synthetase; AmKARS, lysyl-tRNA synthetase; AmLARS, leucyl-tRNA synthetase; AmMARS, methionyl-tRNA synthetase; AmNARS, asparaginyltRNA synthetase; AmPARS, prolyl-tRNA synthetase; AmQARS, glutaminyl-tRNA synthetase; AmRARS, arginyl-tRNA synthetase; AmTARS, threonyl-RNA synthetase; AmVARS, valyltRNA synthetase; AmWARS, tryptophanyl-tRNA synthetase; AmYARS, tyrosyl-tRNA synthetase; EV, Extracellular vesicle. Data shown in (A), (B) and (D-J) are representative of at least three independent experiments, each with similar results (mean±SEM). P-values were calculated using an unpaired two-tailed Student's t-test. Data shown in (C) are representative and repeated at least three times.

Figure 4:
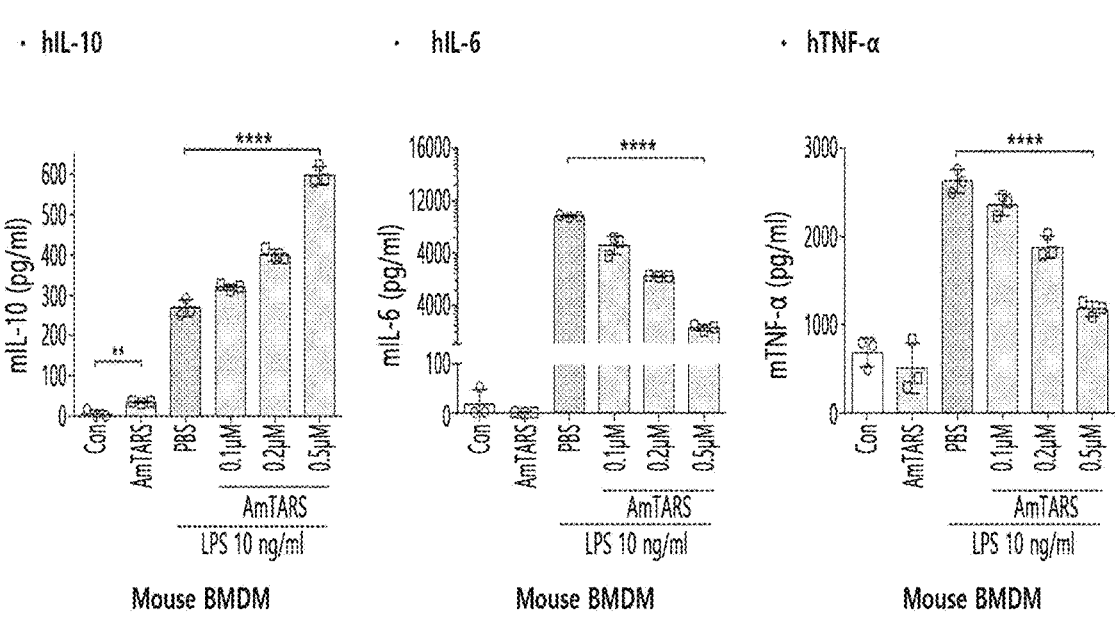

FIG. 4 shows the result of analyzing mouse cytokine expression in bone marrow-derived macrophage (BMDM) cells in an inflammatory environment according to AmTARS treatment.

Figure 5:
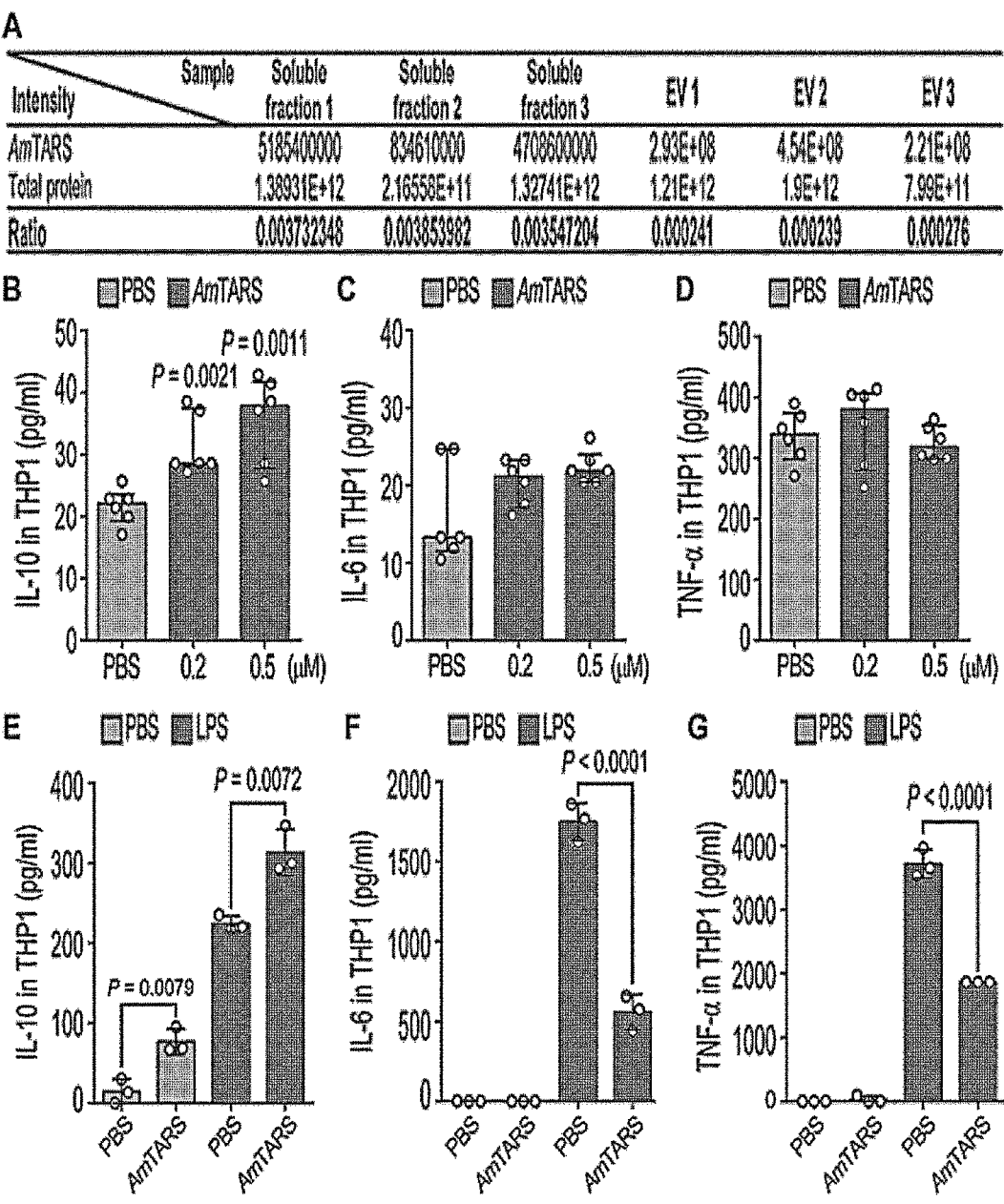

FIG. 5 shows that AmTARS extracellularly secrets to act as an anti-inflammatory immune mediator. (A) Protein intensities of soluble fractions and EVs derived from *A. muciniphila* culture supernatants calculated by LC-MS/MS analysis. The samples used for the analysis were prepared from three independent cultures of *A. muciniphila*. (B-D) Levels of IL-10 (A), IL-6 (B), and TNF-α·(C) in differentiated-THP1 cells treated for 24 h with AmTARS under normal conditions (n=6 per group). (E-G) Levels of cytokines in differentiated-THP1 cells treated for 24 h with AmTARS under LPS-stimulated inflammatory conditions (n=3 per group). Data shown in (B-G) are representative of three independent experiments, each with similar results (mean±SEM). P-values were calculated by an unpaired, two-tailed Student's t-test.

Figure 6:
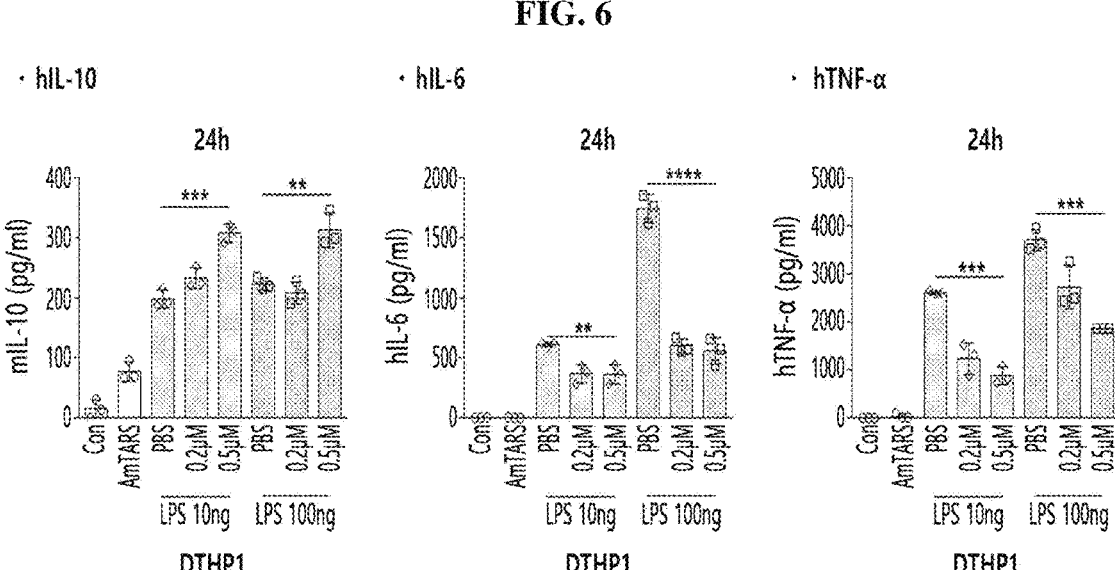

FIG. 6 shows the results of analyzing human cytokine expression in human macrophage (THP1) cells in an inflammatory environment according to AmTARS treatment.

Figure 7:
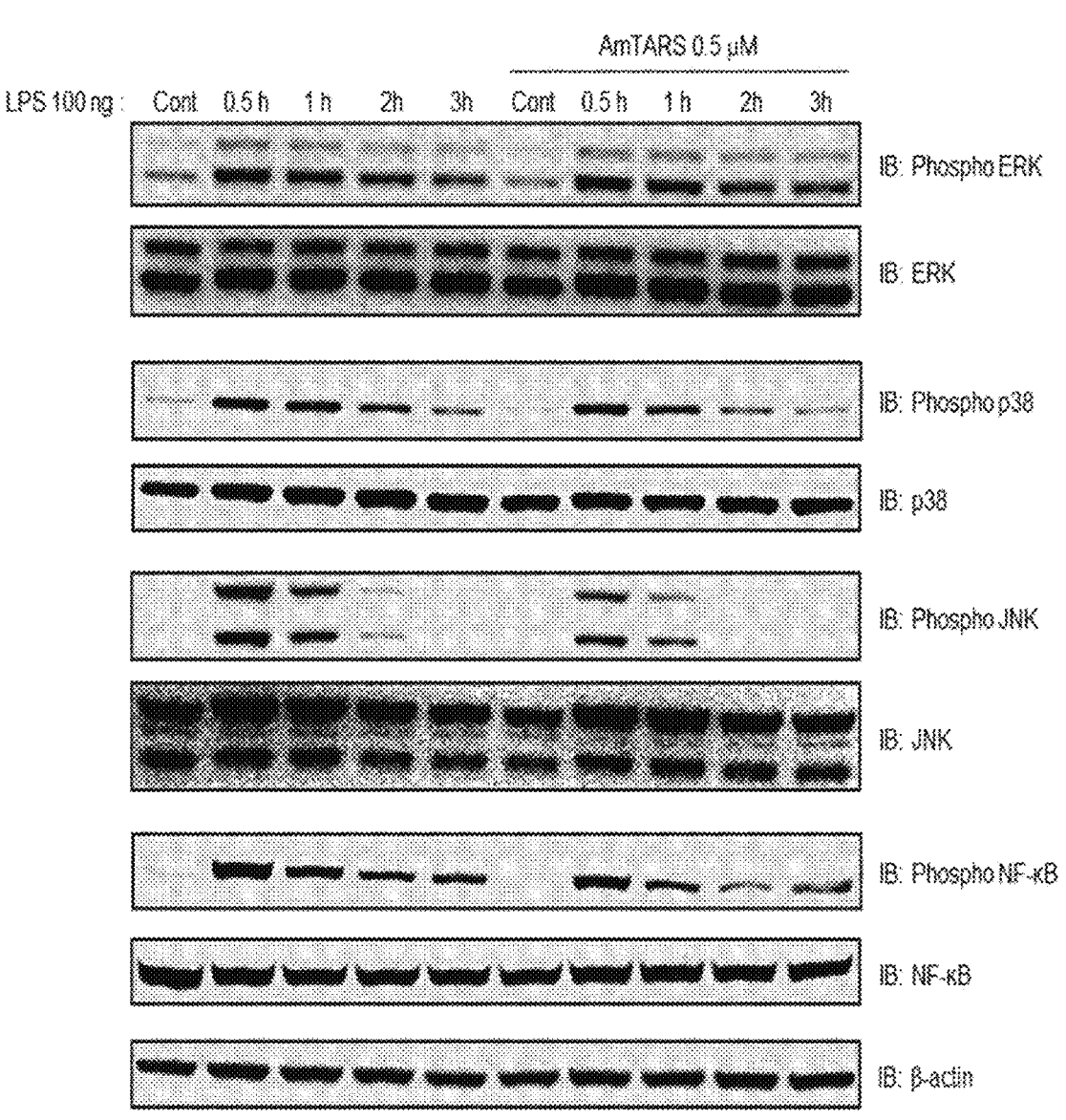

FIG. 7 shows the signaling results in Raw264.7 cells according to the presence or absence of AmTARS treatment in a lipopolysaccharide (LPS)-induced inflammatory environment.

Figure 8:
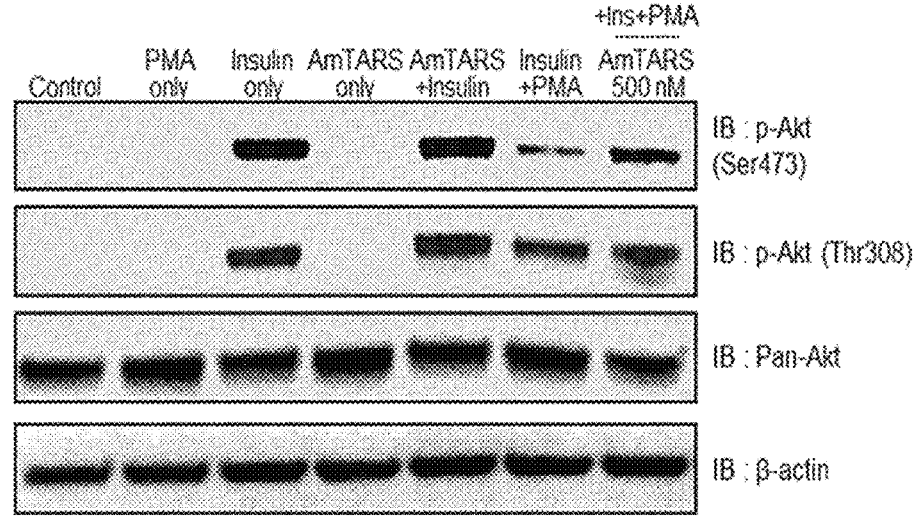
Figure 8:
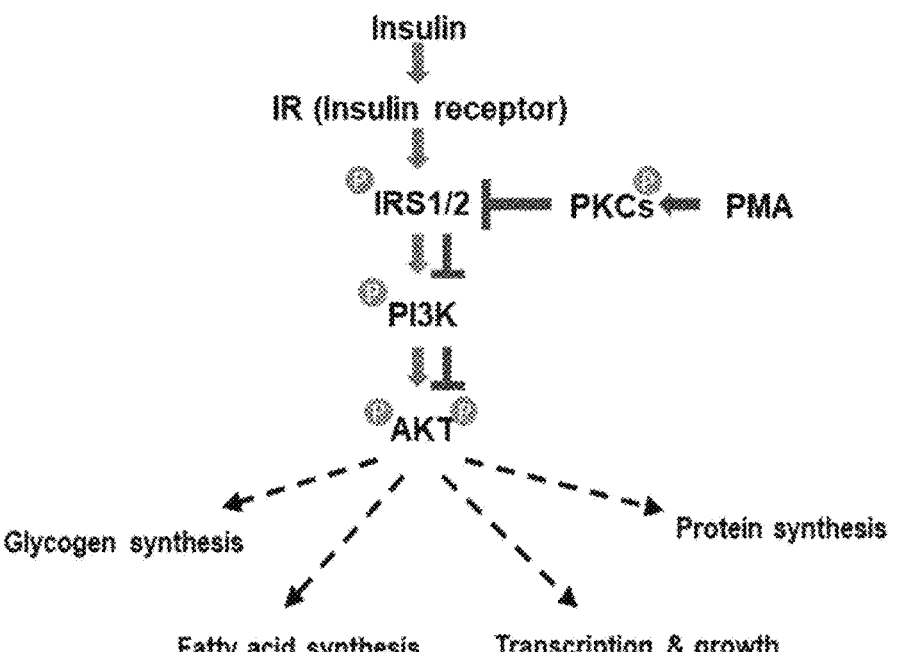

FIG. 8 shows the signaling results in the mouse adipocyte 3T3-L1 cells according to AmTARS treatment in a metabolic inflammation response induced by phorbol 12-myristate 13-acetate (PMA) treatment.

Figure 9:
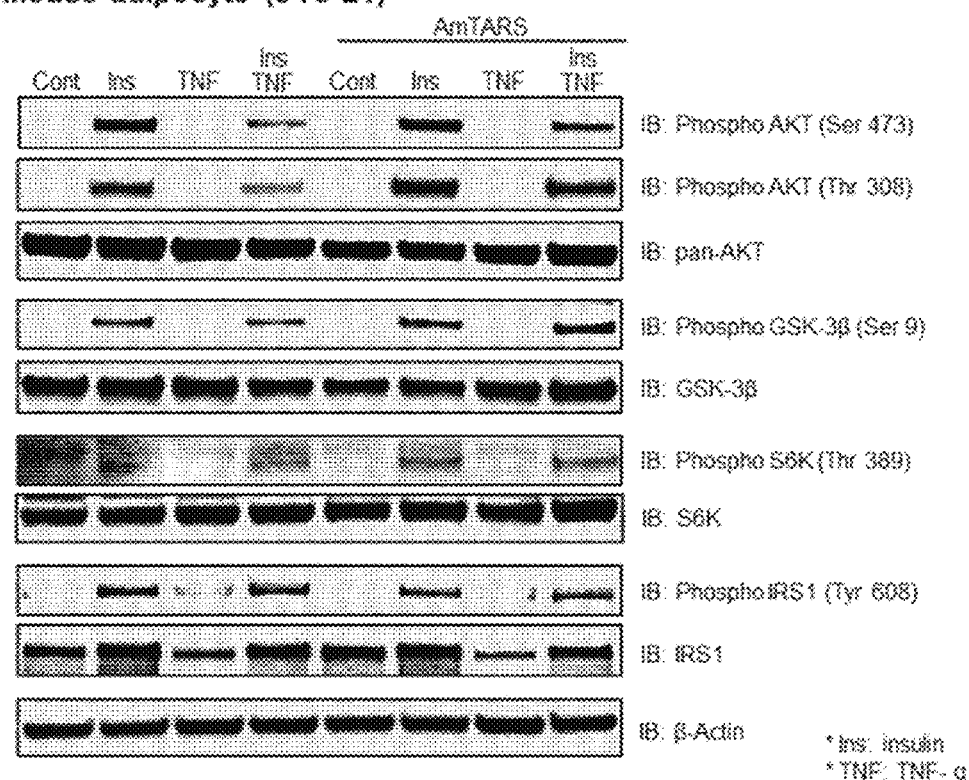
Figure 9:
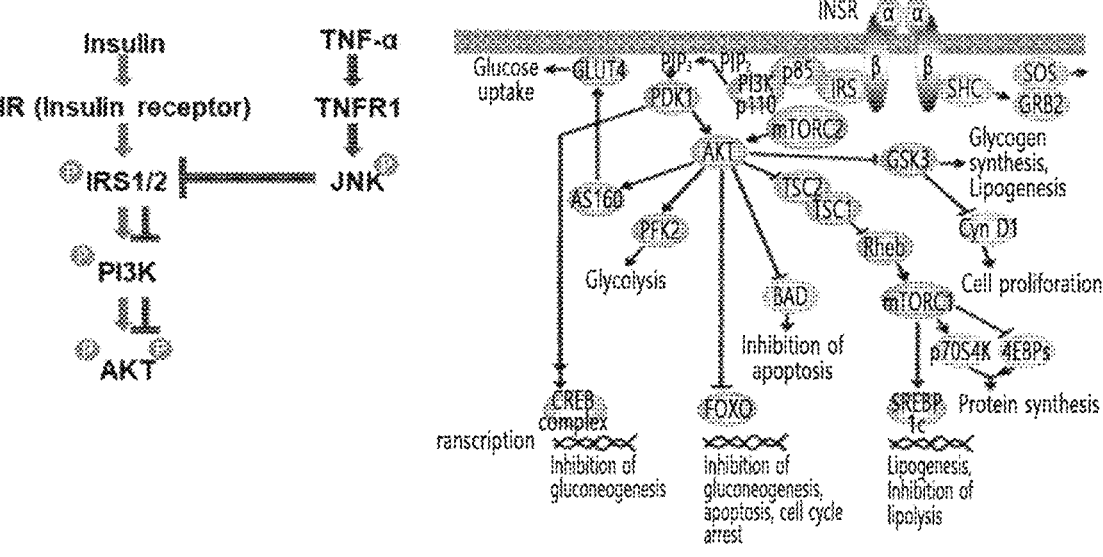

FIG. 9 shows the signaling results in 3T3-L1 cells according to AmTARS treatment in a metabolic inflammation response induced by TNF-α treatment.

Figure 10A:
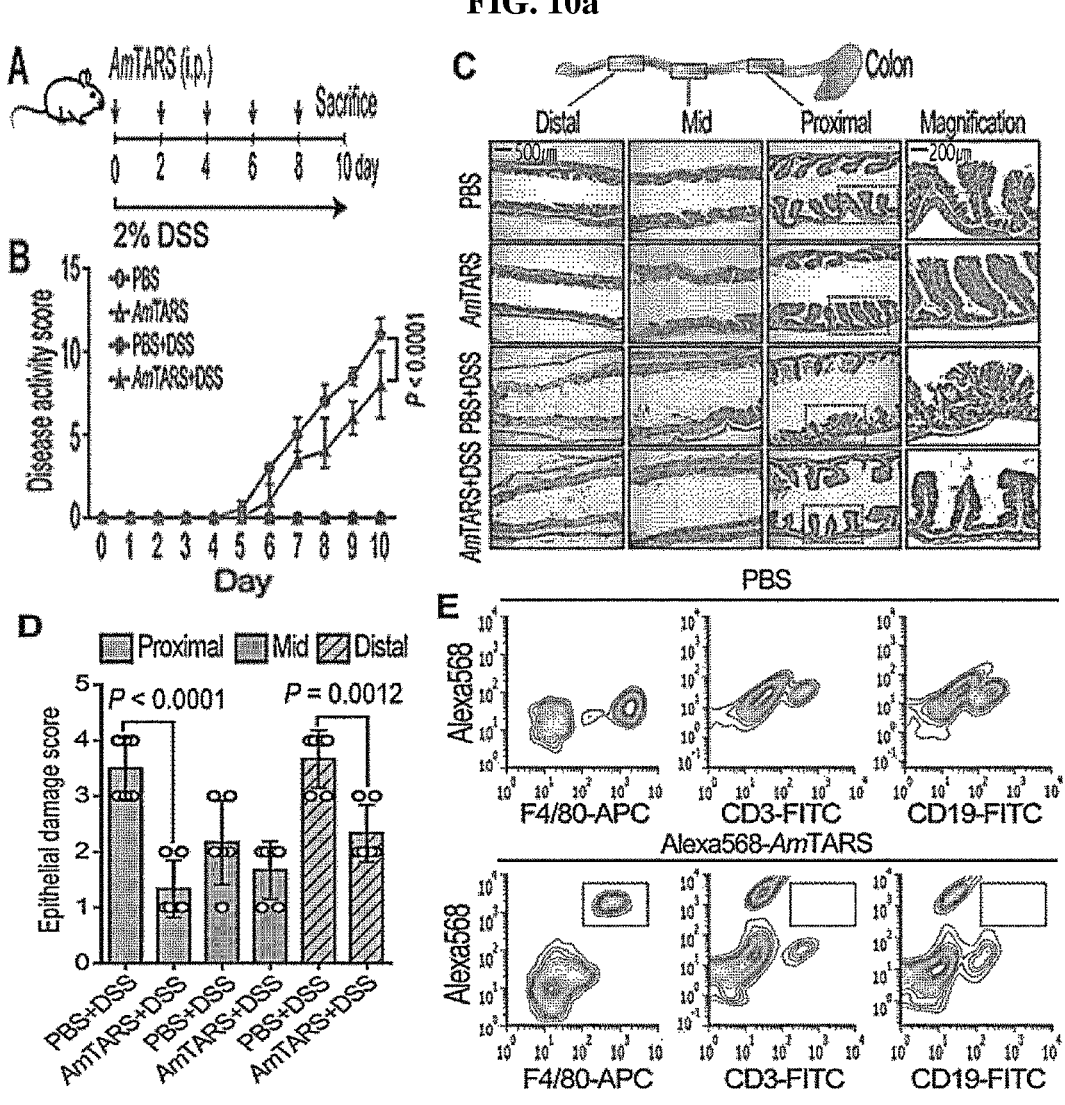
Figure 10B:
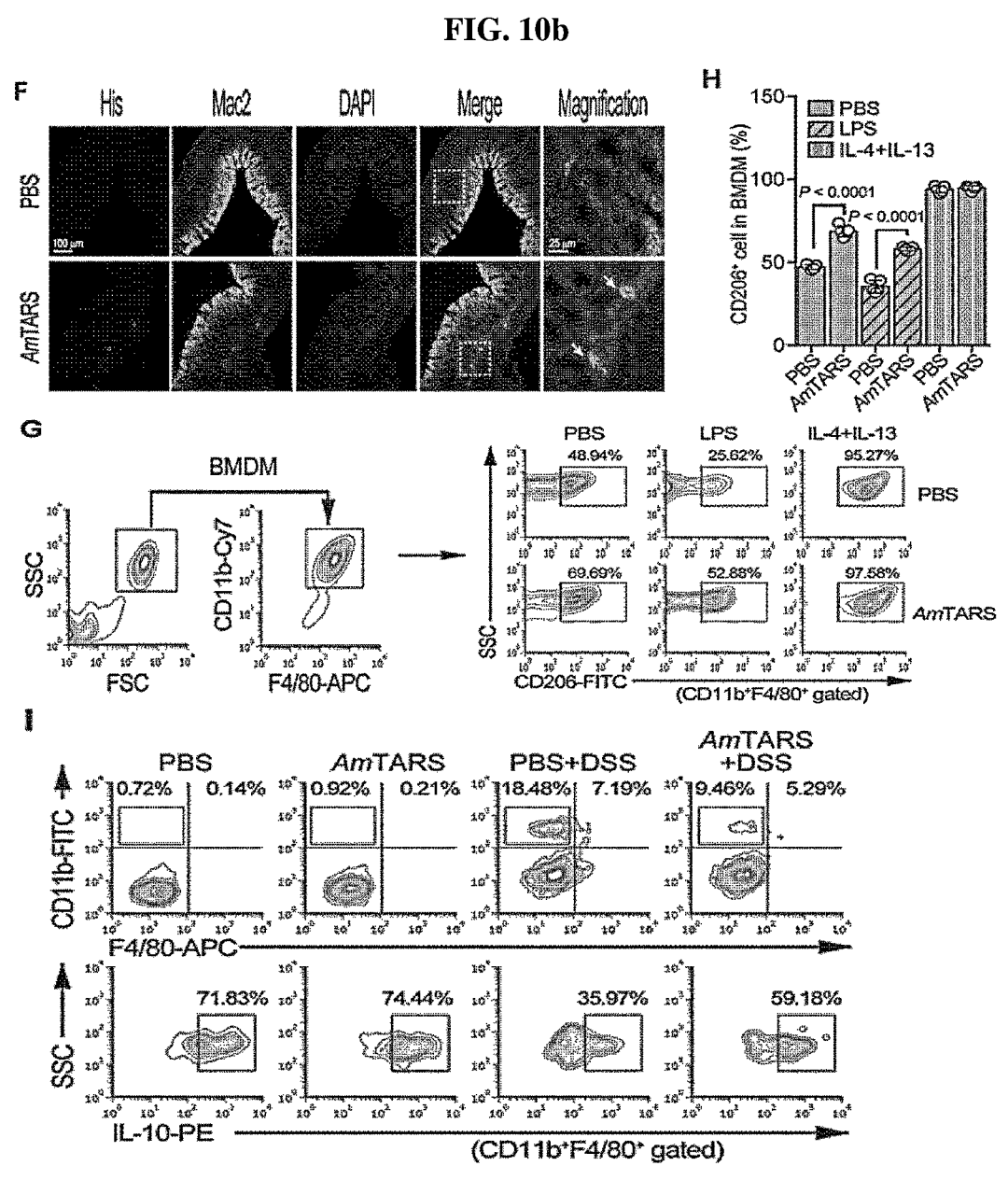
Figure 10C:
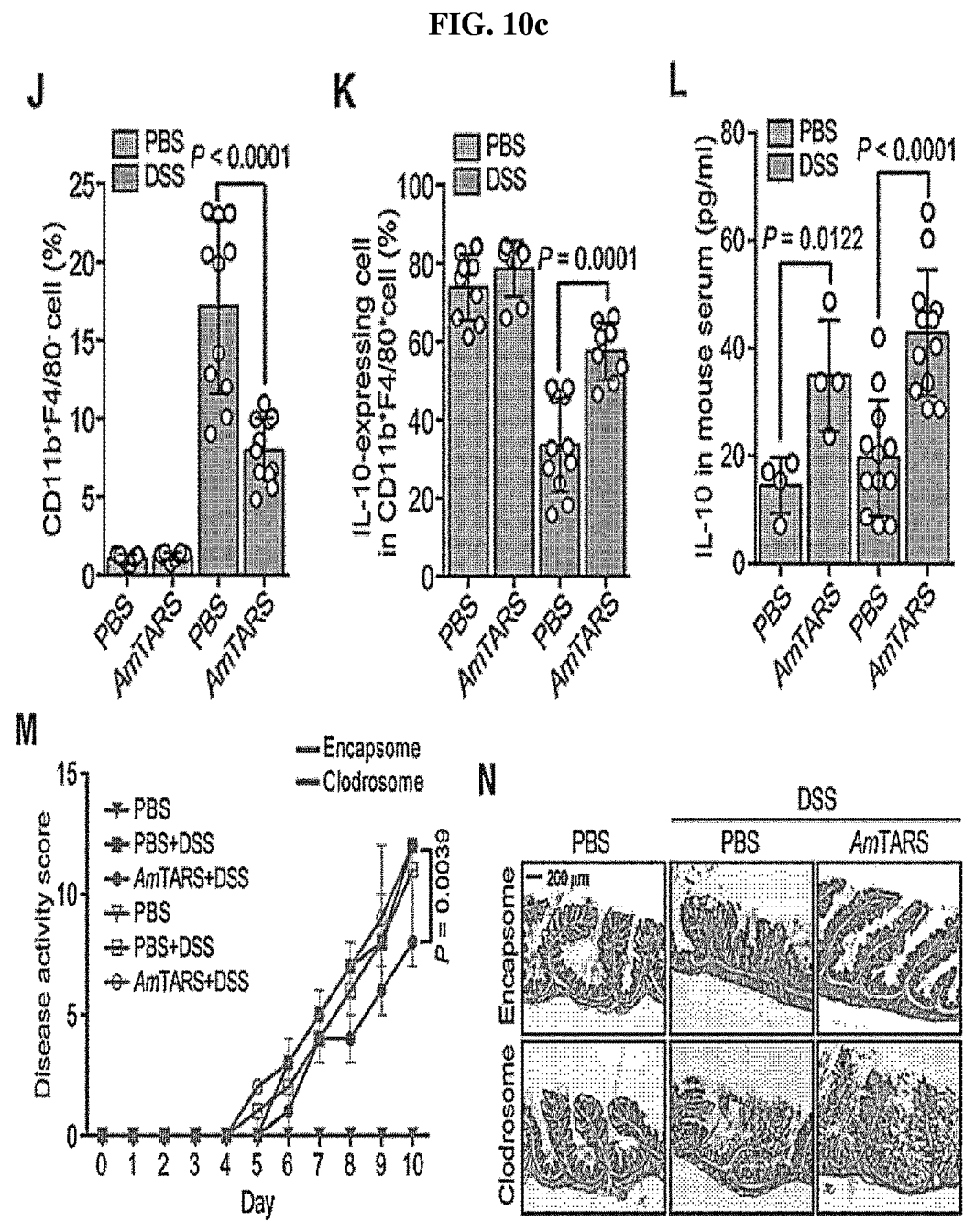

FIG. 10a to FIG. 10c show that AmTARS ameliorates DSS-induced colitis in mice by activating IL-10-positive macrophages. (A-D) Normal or DSS-induced colitis mice injected intraperitoneally (i.p.) with PBS or AmTARS. Experimental scheme (A) and daily changes in disease activity scores (n=10 per group) (B). Representative hematoxylin and eosin staining (H&E) of distal, mid, and proximal regions of the colon (C), and epithelial damage scores (n=6 per group) (D). (E) Flow cytometric analysis of the AmTARS-targeted cells. Macrophages (F4/80+), B cells (CD19+), and T cells (CD3+) were analyzed in PECs isolated from mice injected i.p with PBS or Alexa 568-labeled AmTARS (0.5 mg kg-1) for 1 day. (F) Immunofluorescence staining to detect co-localization of AmTARS (His) and macrophage (Mac2) in the colon of mice treated with His-tagged AmTARS (0.2 mg kg-1) for 1 day. (G) Flow cytometry analysis of CD206+ cells within BMDMs treated with PBS, LPS, or IL-4+IL-13. (H) Percentages of CD206+ cells in G (n=5 per group). (I-L) Normal or DSS-induced colitis mice were treated with PBS or AmTARS. Representative flow cytometry plots showing monocytes (upper panel, CD11b+), macrophages (CD11b+F4/80+), and IL-10-positive macrophages (lower panel) within colon cells (I). Percentage of CD11b+F4/80− (n=7, 8, 11, and 11 per group) (J) and IL-10-expressing macrophages (n=9, 8, 11, and 8 per group) in the mice shown in I (K). IL-10 levels in mouse serum (n=4, 4, 12, and 12 per group) (L). (M and N) Macrophage-dependent AmTARS function. Daily disease activity score (M) and H&E staining in the proximal colon (N) of DSS-induced colitis mice in which macrophages were depleted by Clodrosome treatment (n=5 per group). Encapsome treatment was included as a Clodrosome control. Data shown in (B), (D), (H), and (J-M) are representative of three independent experiments, each with similar results (mean±SEM). P-values were calculated by an unpaired two-tailed Student's t-test. Data shown in (E and F) are representative and repeated at least three times.

Figure 11:
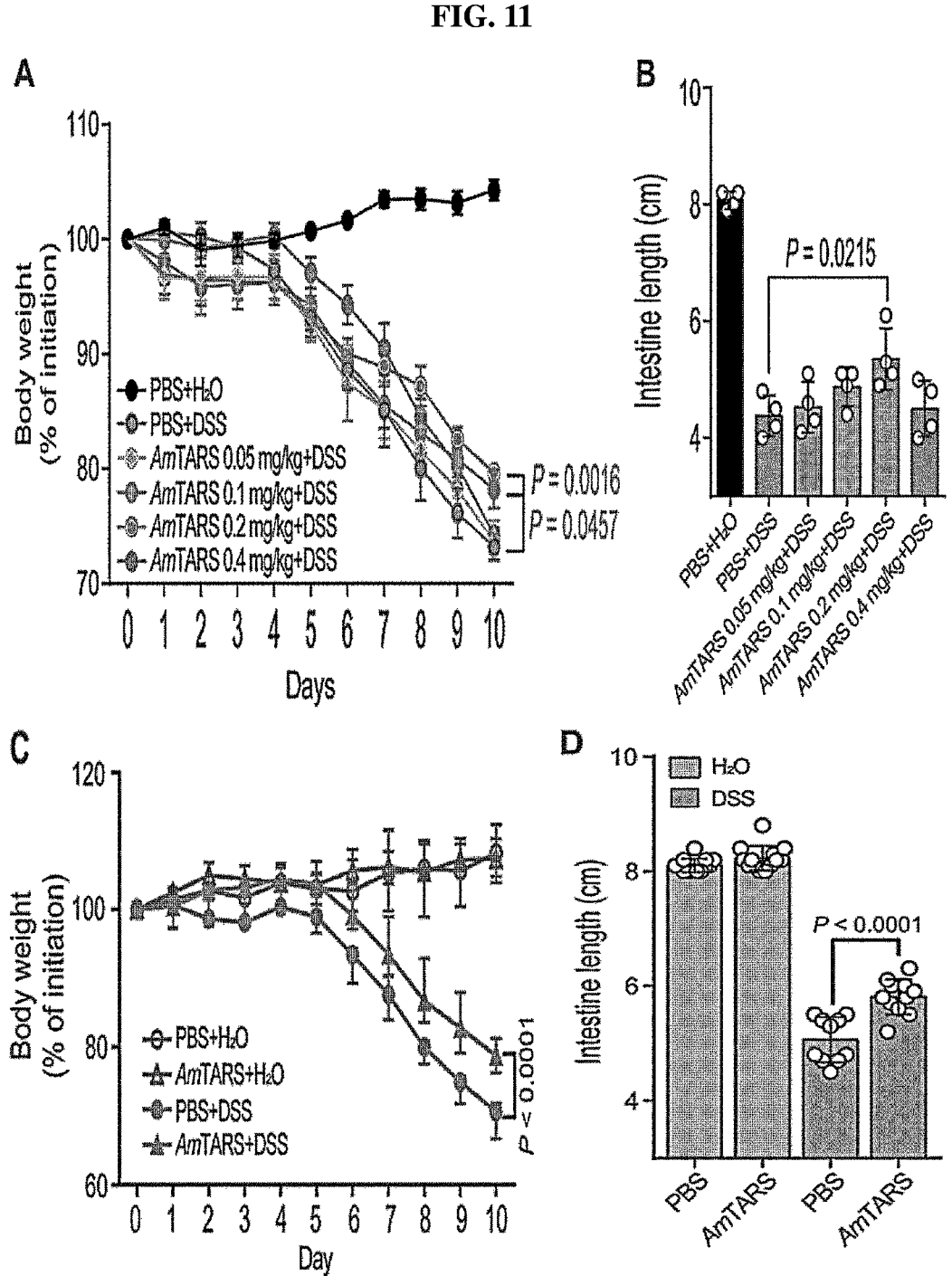

FIG. 11 shows that dose-dependent effects of AmTARS in DSS-induced colitis mice. (A and B) Daily changes in body weight (A) and intestinal colon length (B) in DSS-induced colitis mice treated with the indicated doses of AmTARS (n=4 per group). (C and D) Daily changes in body weight (C) and intestine colon length (D) in colitis mice treated with AmTARS (0.2 mg/kg) (n=10 per group). Data shown are representative of two (A and B) or three (C and D) independent experiments, each with similar results (mean±SEM). P-values were calculated by an unpaired, two-tailed Student's t-test.

Figure 12:
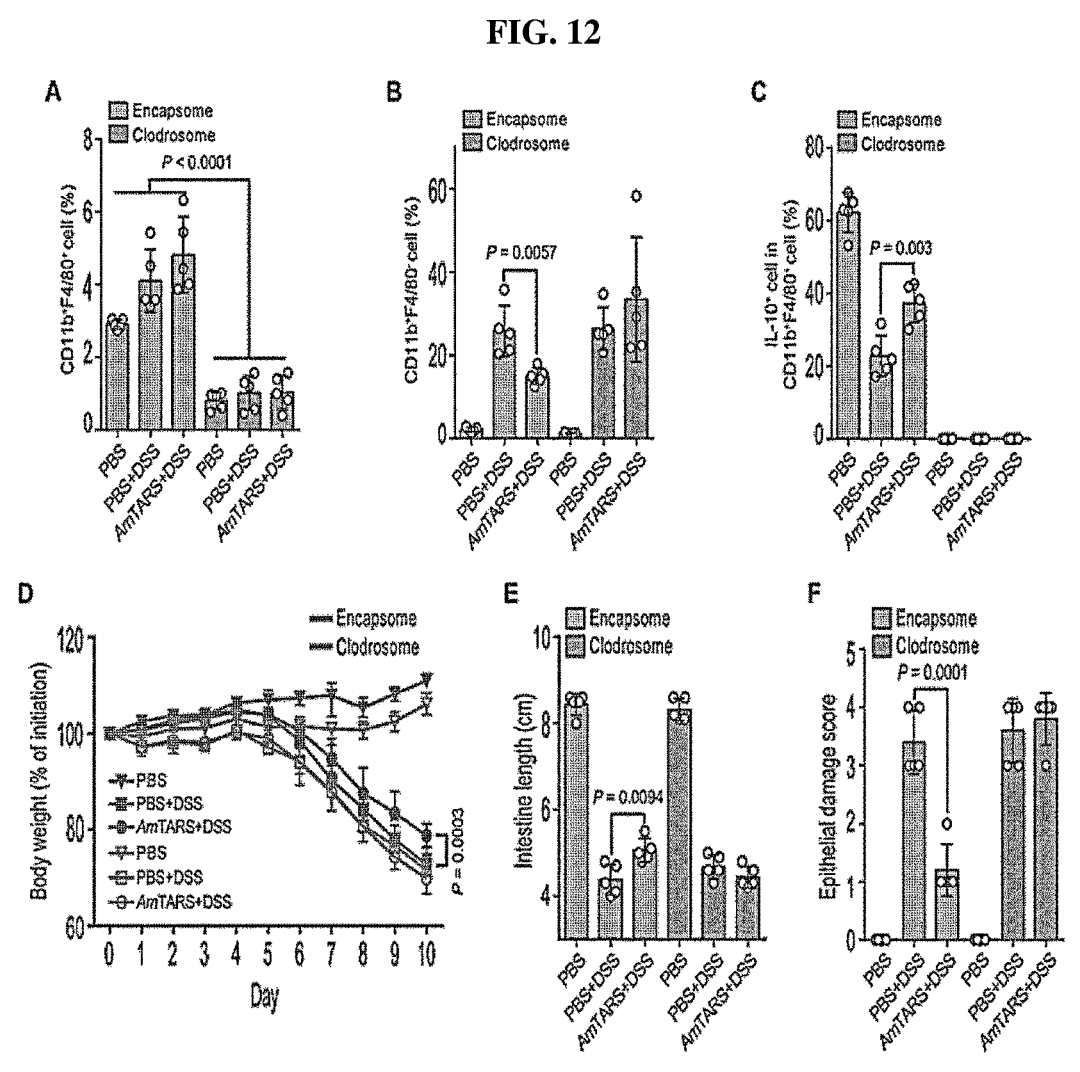

FIG. 12 shows that macrophage-dependent anti-inflammatory function of AmTARS. (A-F) DSS-induced colitis mice depleted of macrophages by treatment with Clodrosome received PBS or AmTARS (n=5 per group). Encapsome was used as the Clodrosome control. The percentage of CD11b+F4/80+ (macrophages) (A), CD11b+F4/80− (monocytes) (B), and CD11b+F4/80+IL-10+ (IL-10-secreting macrophages) (C) cells in the colon was measured by flow cytometry. Daily changes in body weight (D) and measurement of intestine colon length (E). Intestinal epithelial damage score from H&E staining (F). Data shown are representative of three independent experiments, each with similar results (mean±SEM). P-values were calculated by an unpaired, two-tailed Student's t-test.

Figure 13:
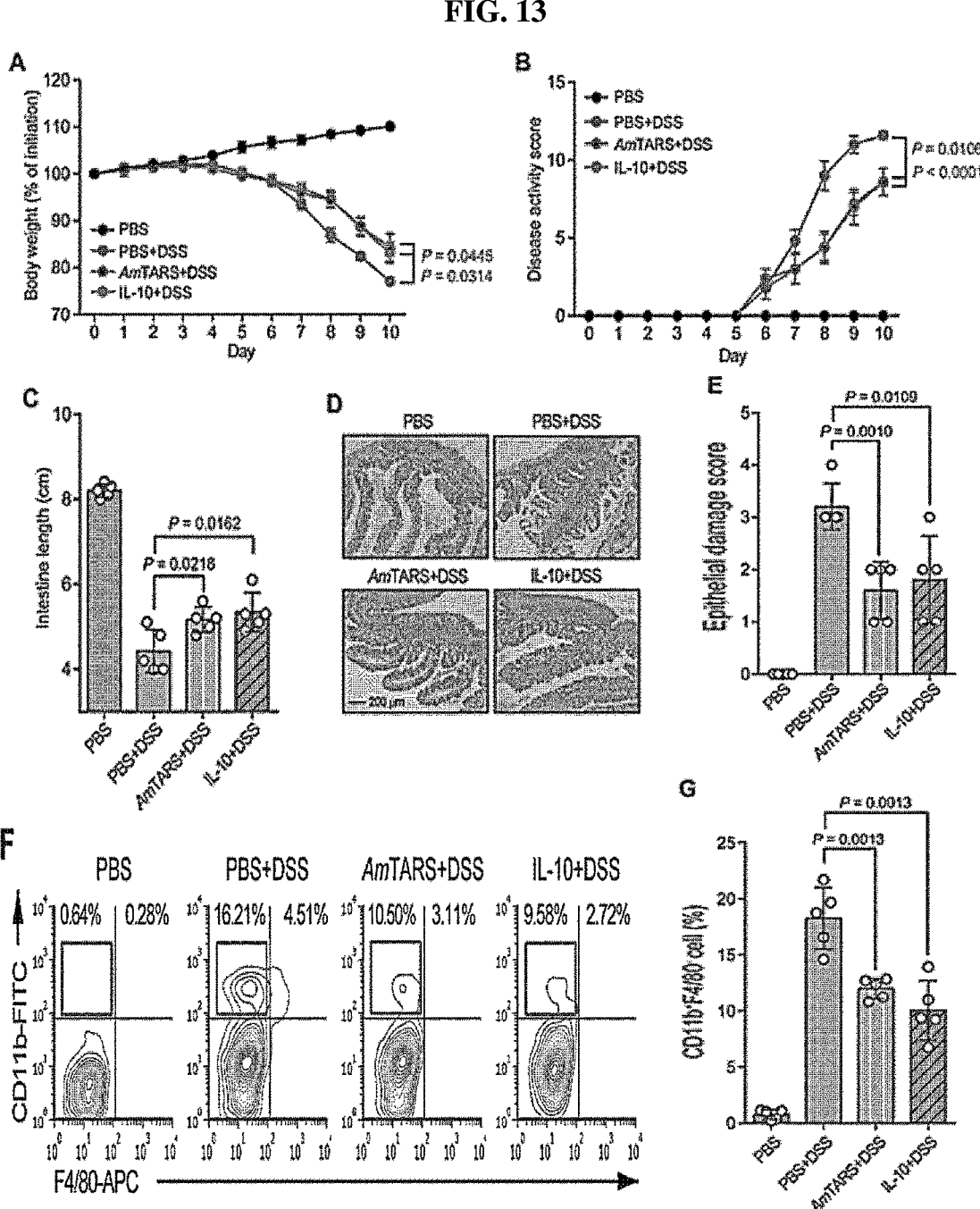

FIG. 13 shows that AmTARS improves physiological signs in DSS-induced colitis mice in a manner comparable with mIL-10. (A-G) Treatment of DSS-induced colitis mice (n=5 per group) with AmTARS (0.2 mg kg-1) and mIL-10 (0.02 mg kg-1). Daily changes in body weight (A), disease activity score (B), and colon length (C). Histology of the colon was analyzed by H&E staining (D), and intestinal epithelial damage was measured (E). Flow cytometry analysis of CD11b− or F4/80− positive cells (F). The percentage of CD11b+F4/80− cells in F is represented as bar graph (G). Data shown in (A-C), (E), and (G) are representative of two independent experiments, each with similar results (mean±SEM). P-values were calculated by an unpaired, two-tailed Student's t-test.

Figure 14:
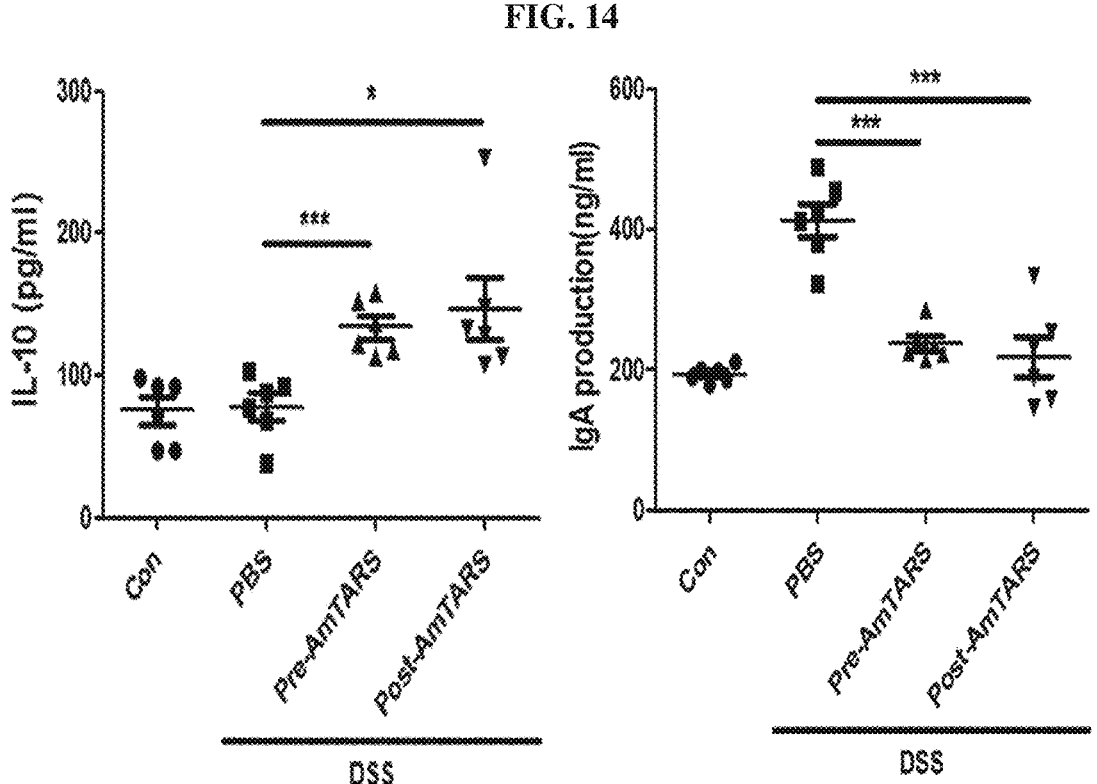

FIG. 14 shows the results of analyzing IL-10, IgA, and cell distribution changes according to AmTARS treatment in an inflammatory bowel disease mouse model.

Figure 15:
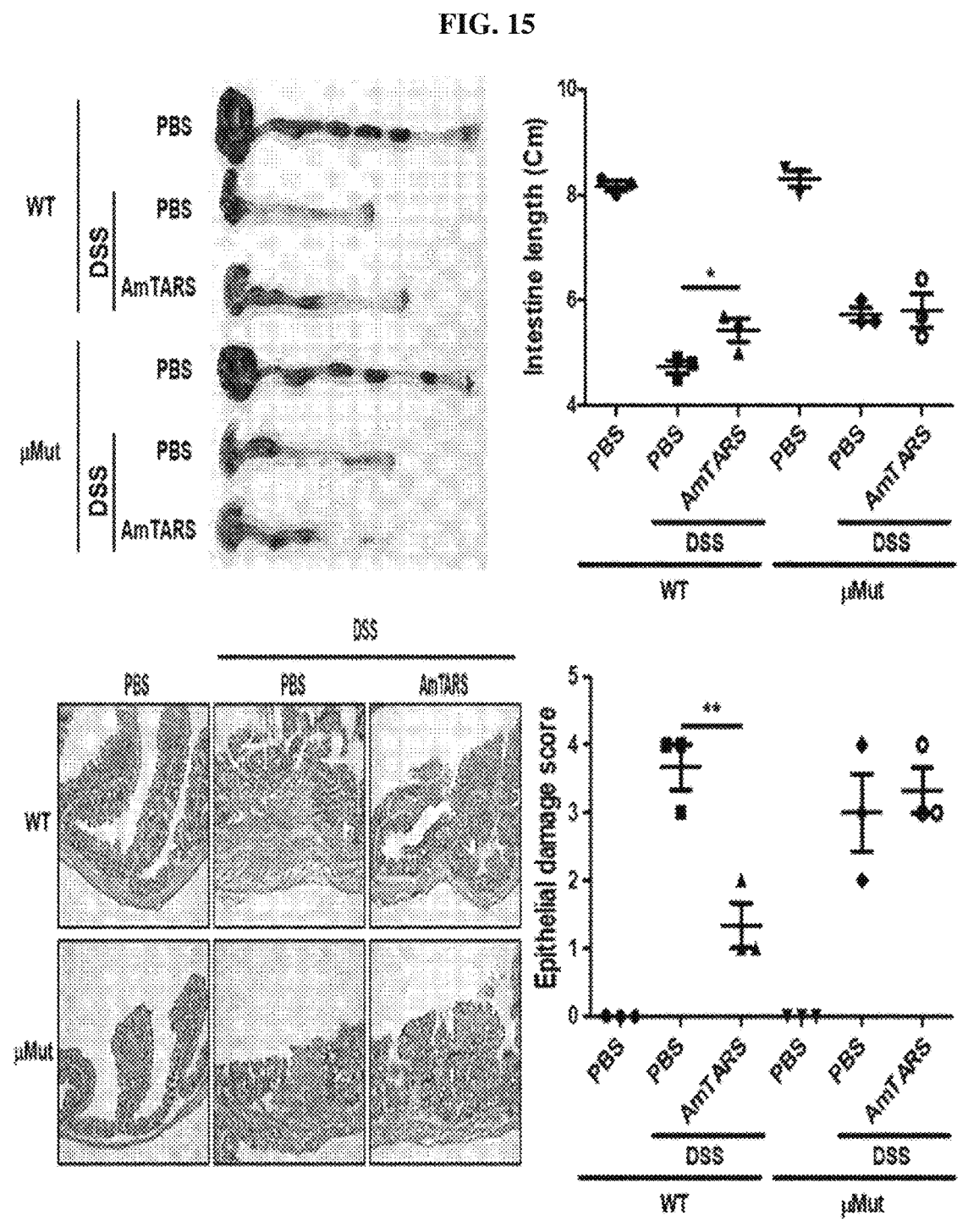

FIG. 15 shows the results of analyzing the intestine length and colon tissue damage according to AmTARS treatment in inflammatory bowel disease-induced B cell-deficient mice or a normal mouse model.

Figure 16:
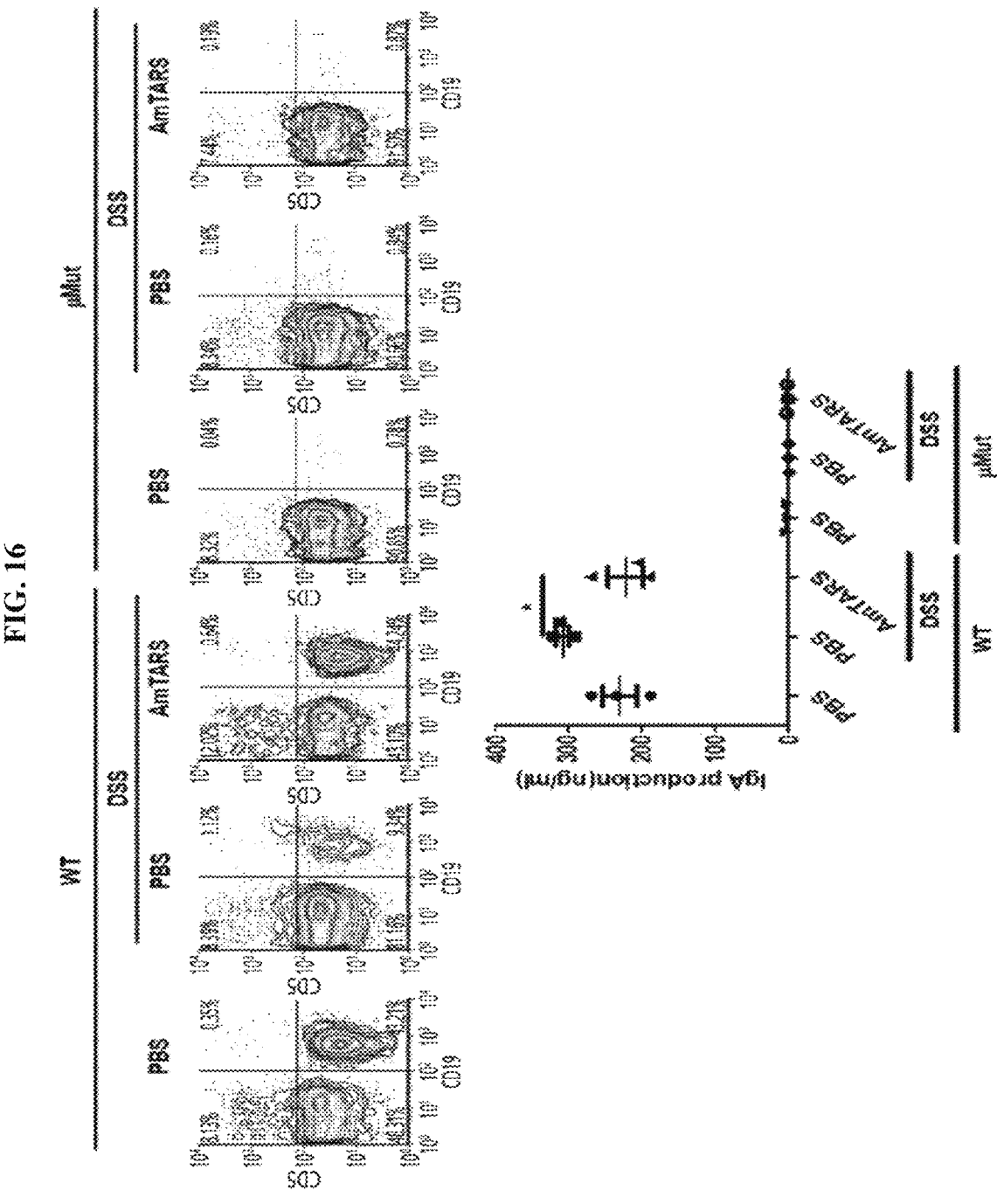

FIG. 16 shows the results of analyzing IgA and cell distribution changes according to AmTARS treatment in inflammatory bowel disease-induced B cell-deficient mice or a normal mouse model.

Figure 17:
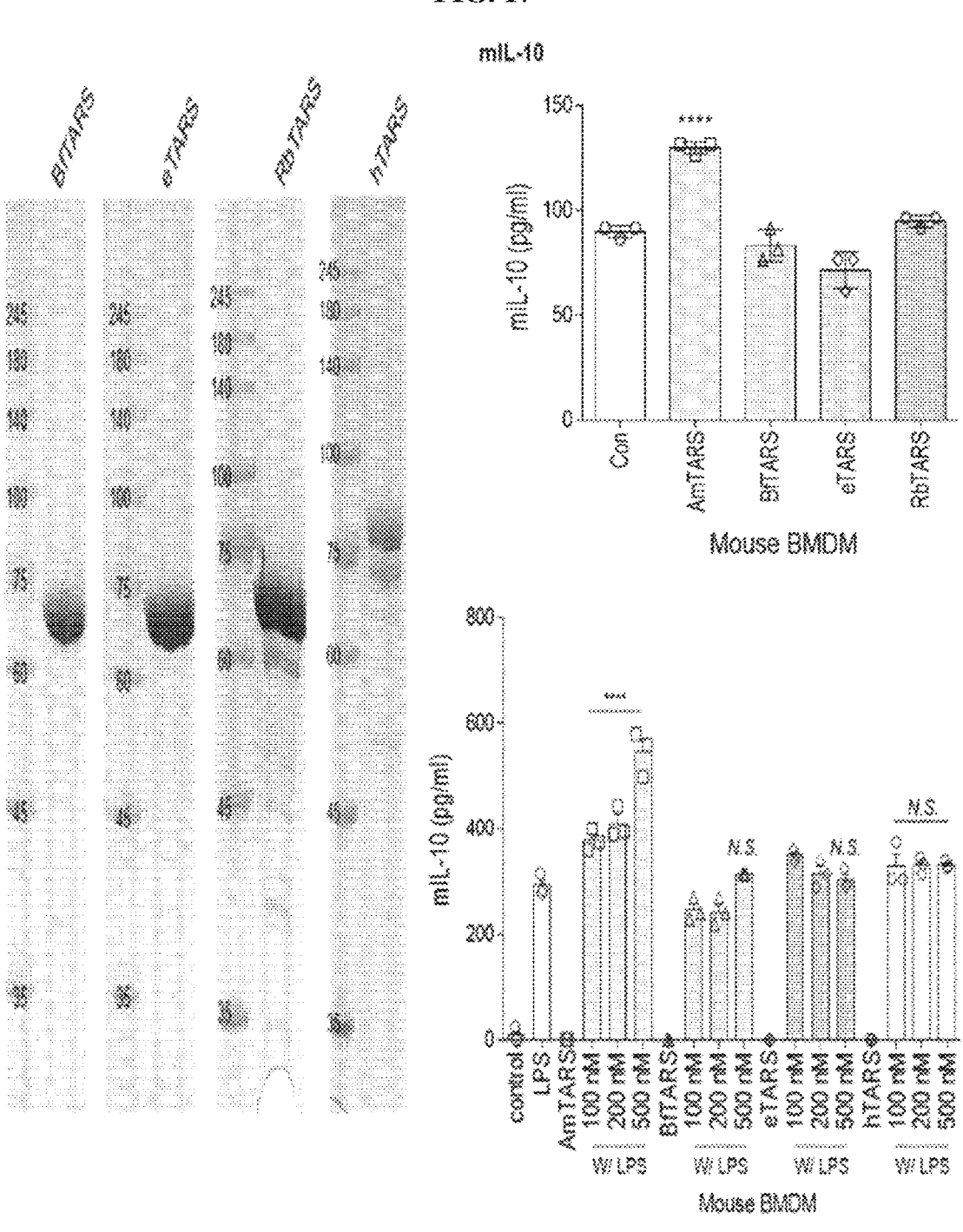

FIG. 17 shows the results of analyzing mouse cytokine expression in BMDM cells according to treatment with main TARS proteins derived from the microbiome and humans.

Figure 18:
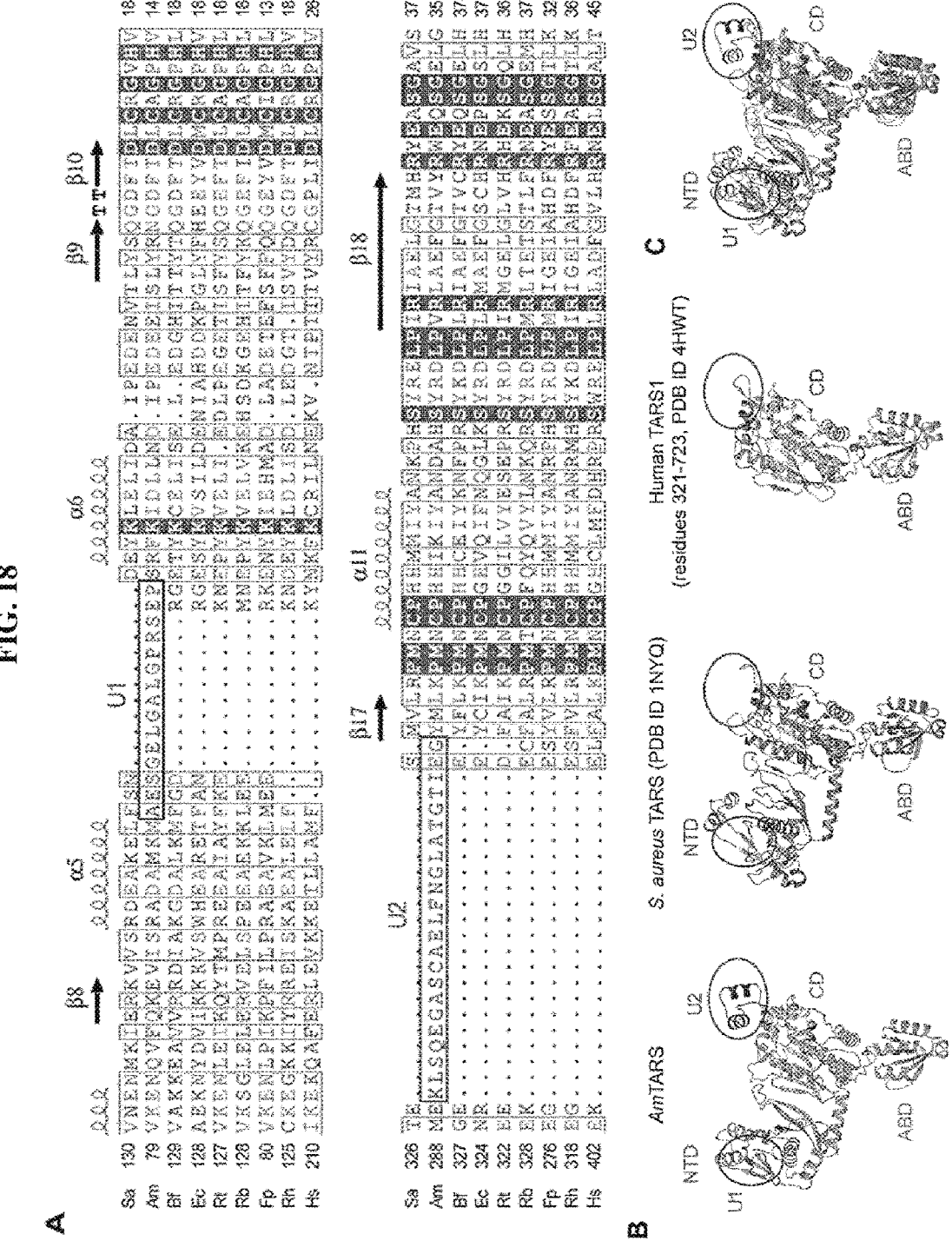

FIG. 18 shows that comparison of TARSs from different species. (A) Comparison of the amino acid sequences of TARSs from different species. The full-length amino acid sequence of *Akkermansia muciniphila* TARS (AmTARS) corresponds to SEQ ID NO: 1. The unique region U1 of AmTARS (residues 99-113 of SEQ ID NO: 1) corresponds to SEQ ID NO: 3, and the unique region U2 of AmTARS (residues 290-312 of SEQ ID NO: 1) corresponds to SEQ ID NO: 4. Secondary structures are based on the crystal structure of *S. aureus* (Sa) TARS (PDB 1NYQ). The unique regions U1 and U2 in AmTARS (Am) were assigned by structural-based sequence alignment with other TARSs from different species. (B) Structural comparison of AmTARS (green) with *S. aureus* TARS (PDB ID 1NYQ, orange) and human TARS1 (residues 321-723; PDB ID 4HWT, magenta). (C) Superimposition of the AmTARS structure with other TARS structures. The structure of AmTARS was modeled using Alphafold2. The U1 and U2 regions are highlighted by blue and red circles, respectively. Bf, *Bacteroides fragilis*; Ec, *Escherichia coli*; Rt, *Ruminococcus torques*; Rb, *Ruminococcus bromii*; Fp, *Faecalibacterium prausnitzii*; Rh, *Roseburia hominis*; Hs, *Homo sapiens*.

Figure 19:
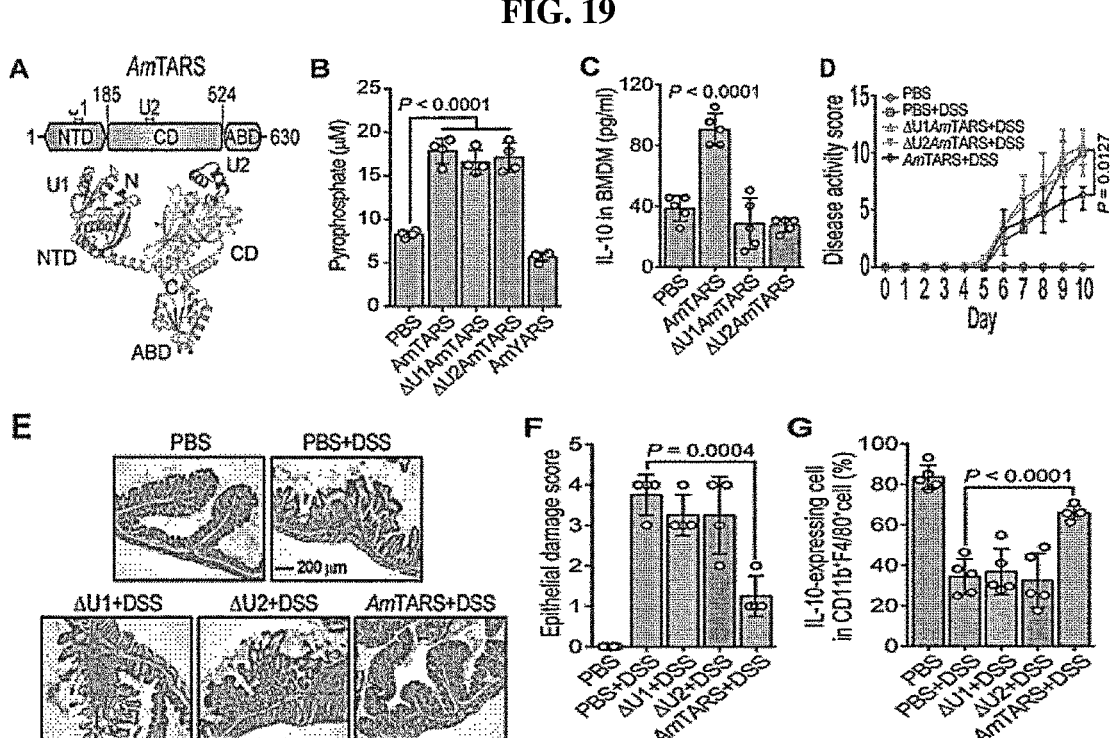

FIG. 19 shows that unique regions in AmTARS are essential for anti-inflammatory immune regulation. (A) A structural model of AmTARS based on the crystal structure of *S. aureus* TARS (PDB 1NYQ). The unique regions (U1 and U2) in AmTARS are indicated in red. (B) Aminoacylation activity assay of AmTARS and its unique region-deleted mutants. AmYARS was used as a negative control. (C) IL-10 production by BMDMs treated with AmTARS or unique region-deleted AmTARS mutants (ΔU1AmTARS and ΔU2AmTARS). (D-G) DSS-induced colitis mice treated with AmTARS or unique region-deleted AmTARS mutants (n=5 per group). Daily changes in the disease activity score (D). H&E staining of the proximal colon (E). Scoring of epithelial damage in E (F). Percentage of CD11b+F4/80+ IL-10+ cells within colon cells (G). Data shown in (B-D), (F), and (G) are representative of three independent experiments, each with similar results (mean±SEM). P-values were calculated by an unpaired two-tailed Student's t-test.

Figure 20:
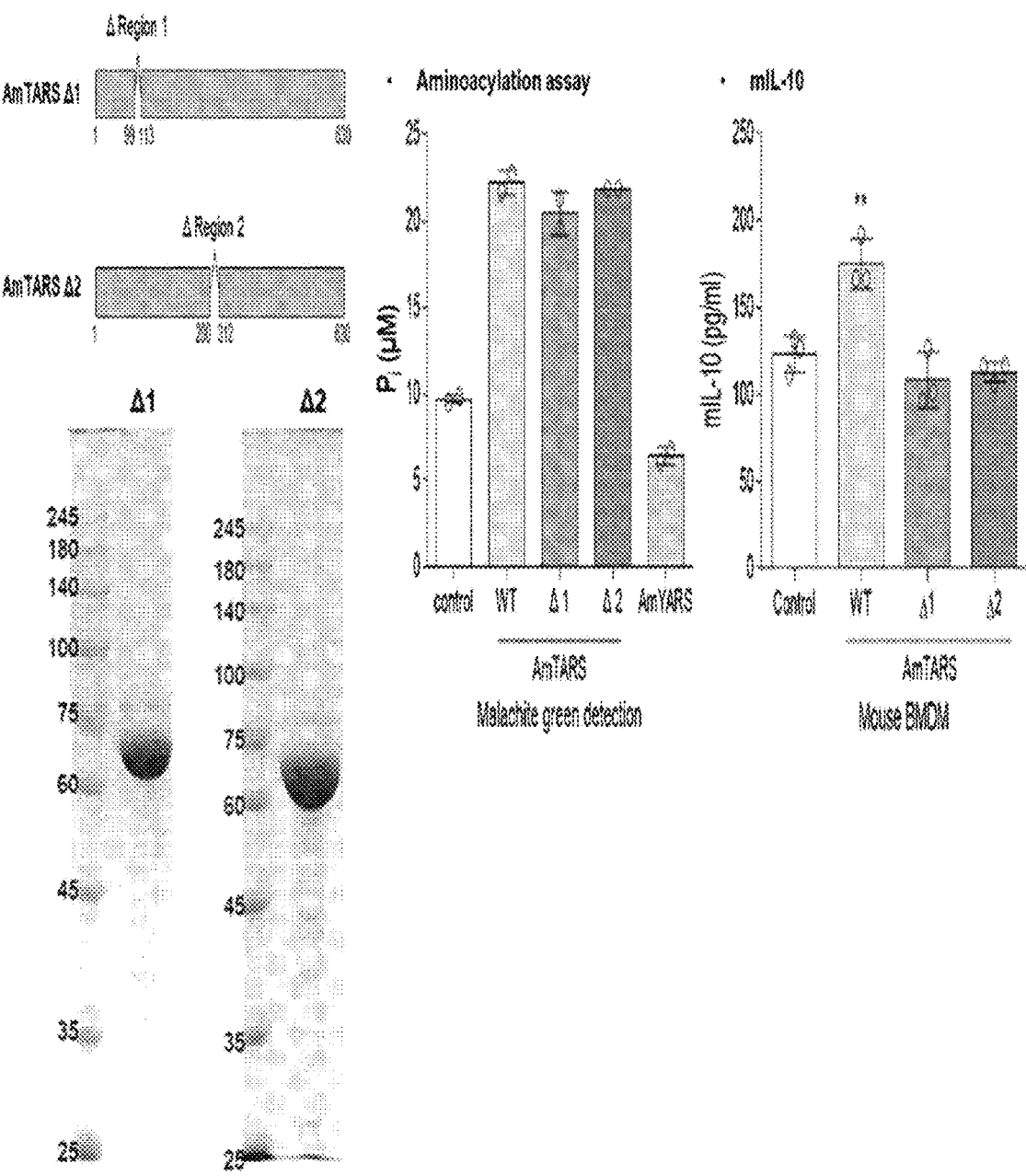

FIG. 20 shows enzymatic activity of proteins having deletions of AmTARS functional sites 1 and 2 and the results of analyzing IL-10 cytokine expression in BMDM cells treated with the proteins.

Figure 21:
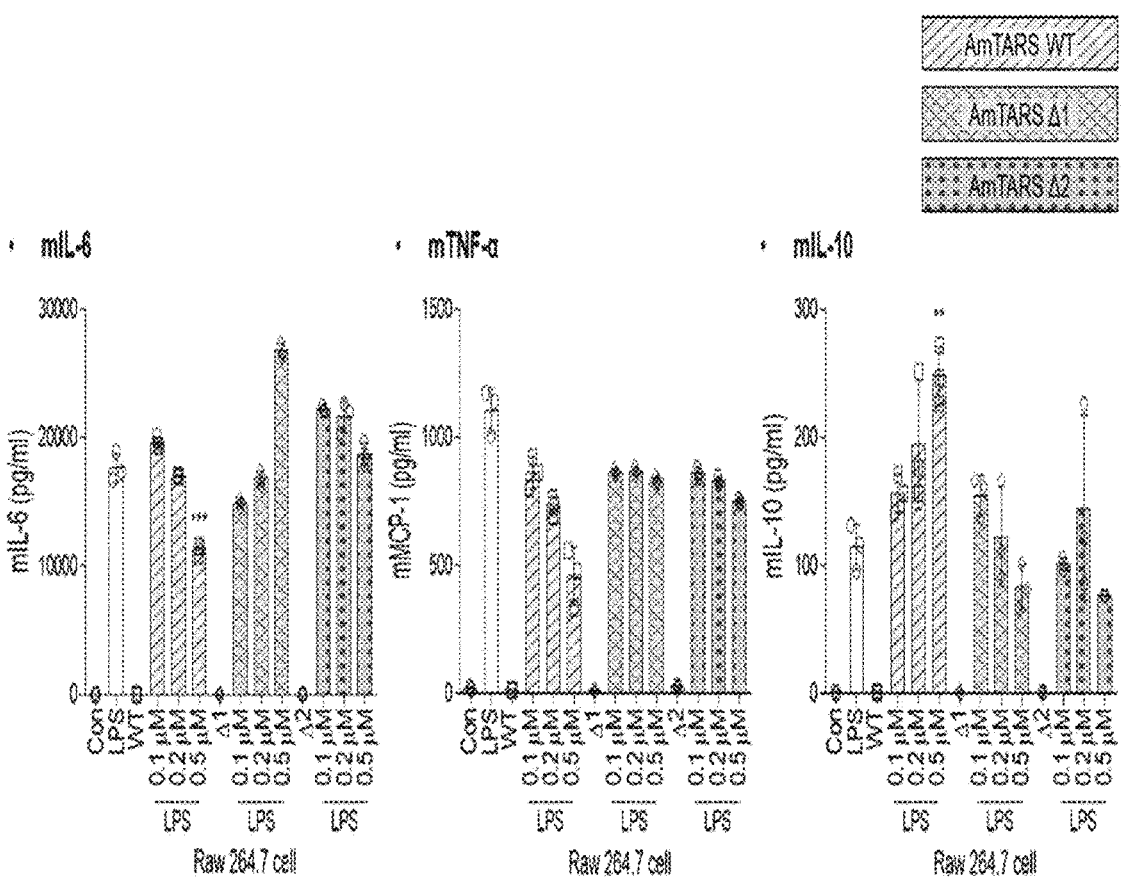

FIG. 21 shows the results of analyzing mouse cytokine expression in Raw264.7 cells treated with proteins having deletions of AmTARS functional sites 1 and 2 in an inflammatory environment.

Figure 22:
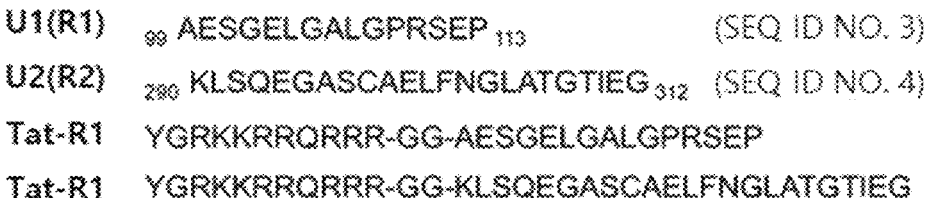
Figure 22:
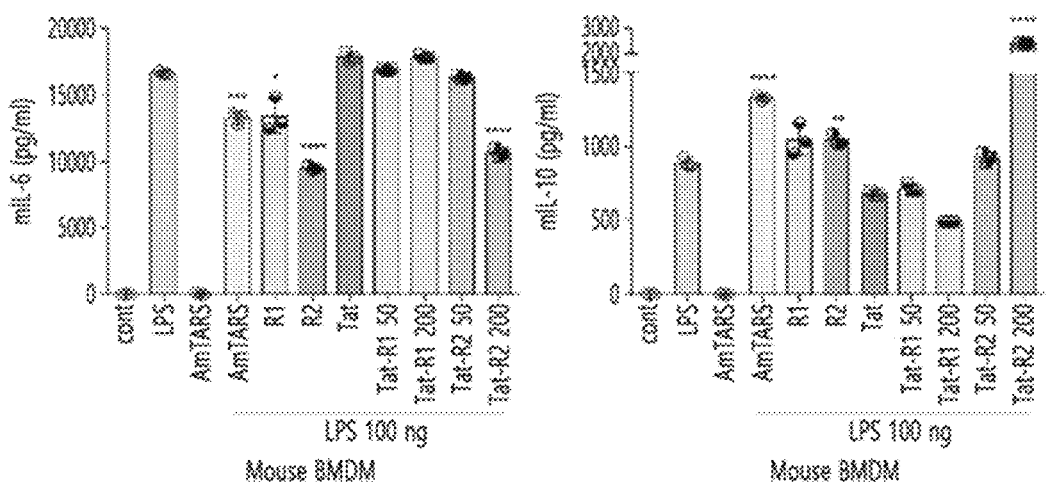
Figure 22:
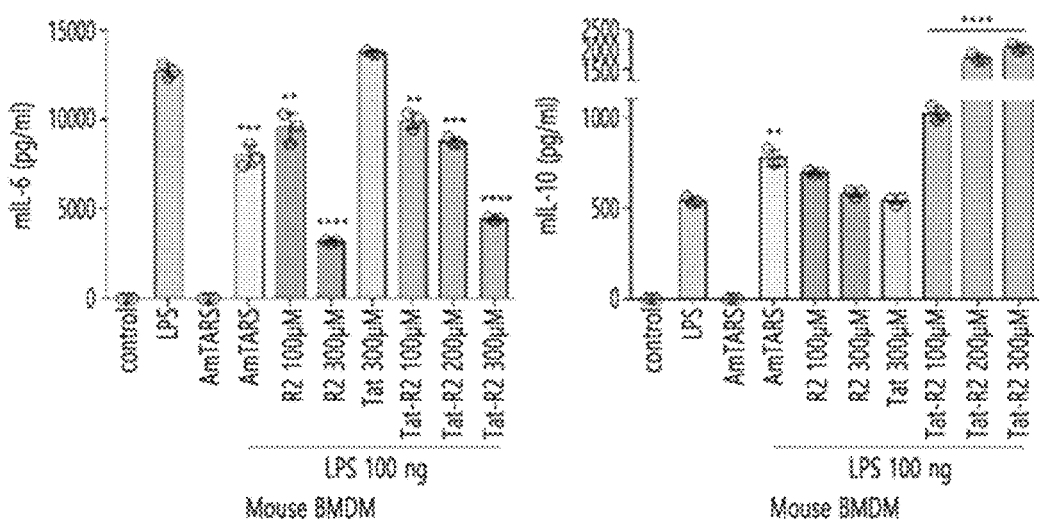

FIG. 22 shows the results of analyzing mouse cytokine expression in BMDM cells treated with AmTARS functional sites 1 and 2 peptides in an inflammatory environment. The functional site 1 peptide (U1 or R1) corresponds to the amino acid sequence of SEQ ID NO: 3 (residues 99-113 of the full-length AmTARS sequence, SEQ ID NO: 1). The functional site 2 peptide (U2 or R2) corresponds to the amino acid sequence of SEQ ID NO: 4 (residues 290-312 of SEQ ID NO: 1).

Figure 23:
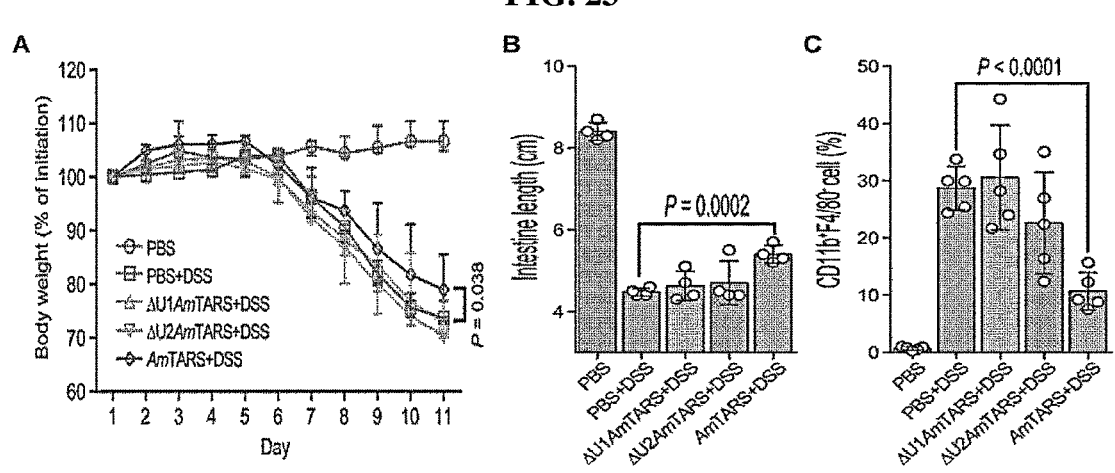

FIG. 23 shows that unique regions are essential for the anti-inflammatory immune function of AmTARS. (A-C) DSS-induced colitis mice were treated with AmTARS or unique region-deleted AmTARS mutants. Daily changes in body weight (n=5 per group) (A) and measurement of intestine colon length (n=4 per group) (B). The percentage of CD11b+F4/80− cells in the colon was measured by flow cytometry (n=5 per group) (C). Data shown are representative of three independent experiments, each with similar results (mean±SEM). P-values were calculated by an unpaired, two-tailed Student's t-test.

Figure 24:
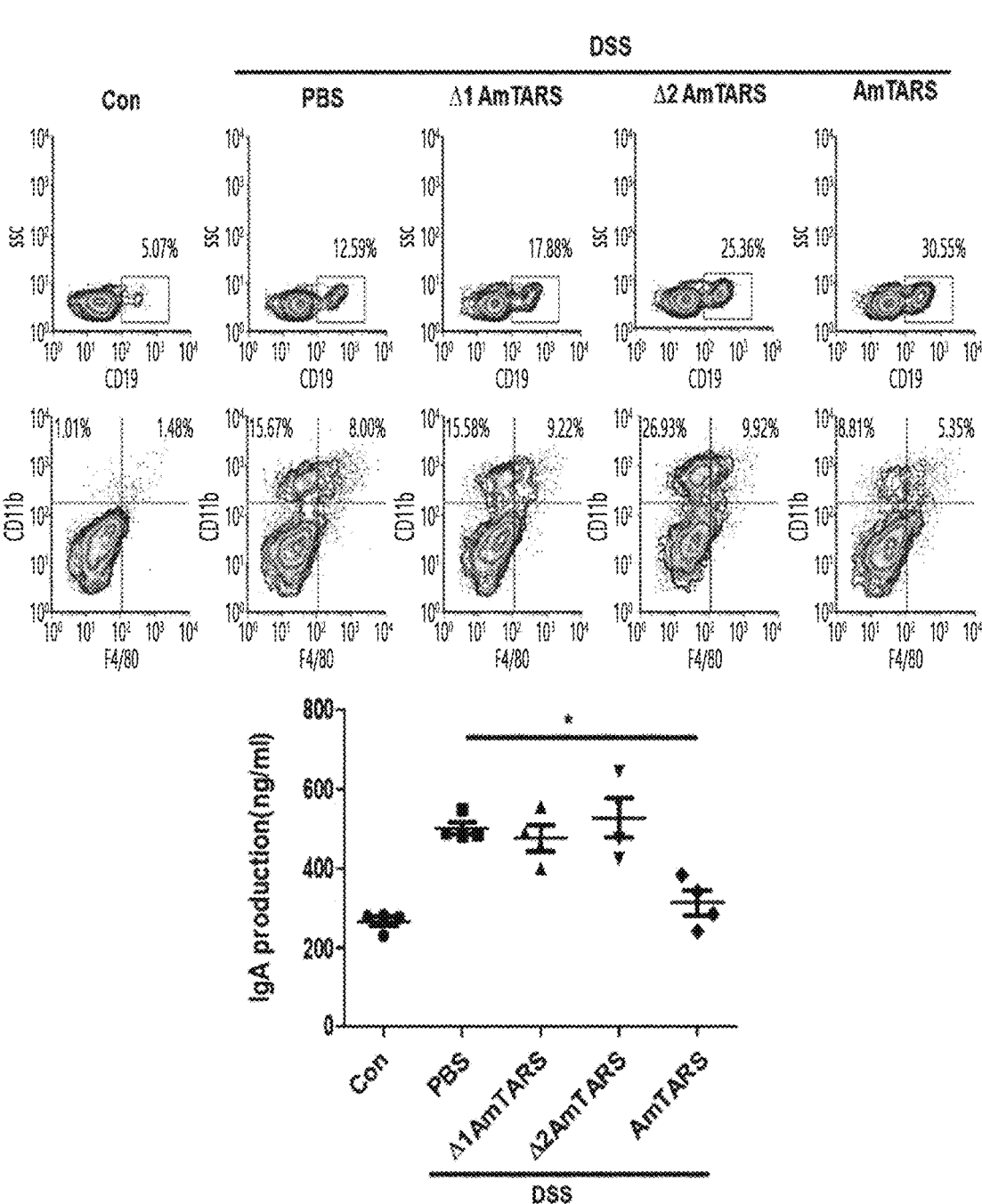

FIG. 24 shows the results of analyzing IgA and cell distribution changes according to the treatment with proteins having deletions of AmTARS functional sites 1 and 2 in an inflammatory bowel disease mouse model.

Figure 25:
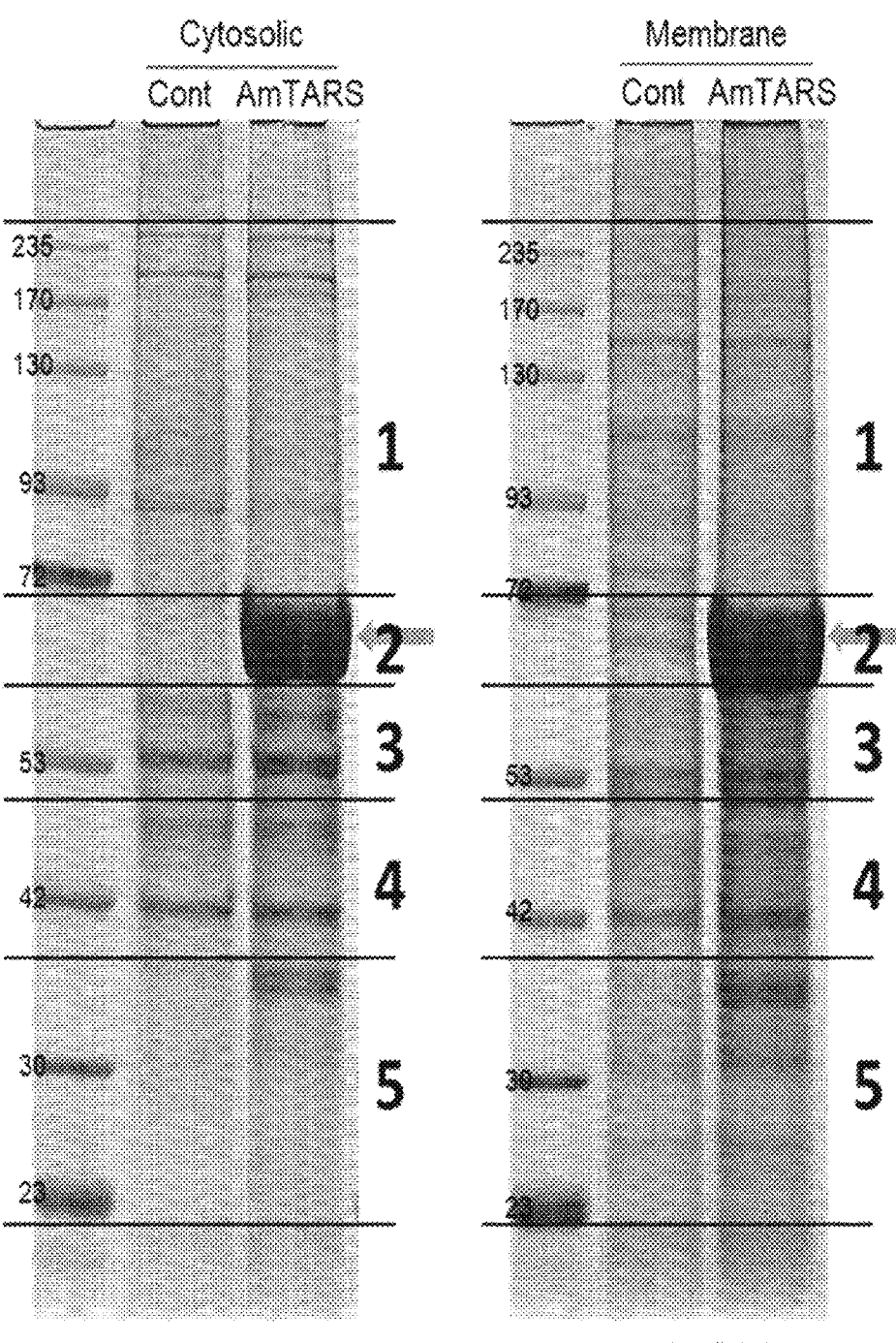

FIG. 25 shows the results of analyzing proteins interacting with AmTARS.

Figure 26:
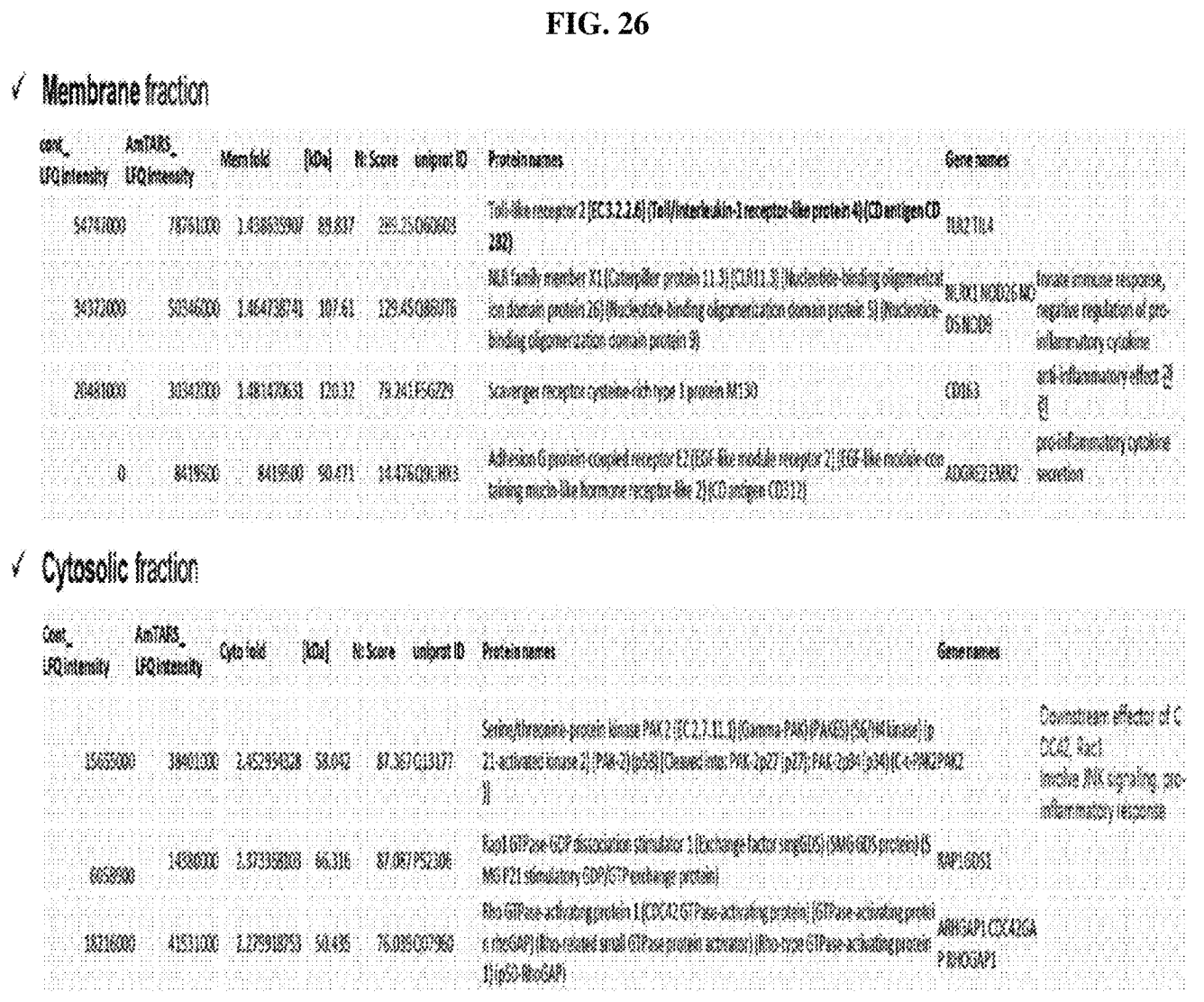

FIG. 26 shows the MS analysis results of proteins interacting with AmTARS.

Figure 27:
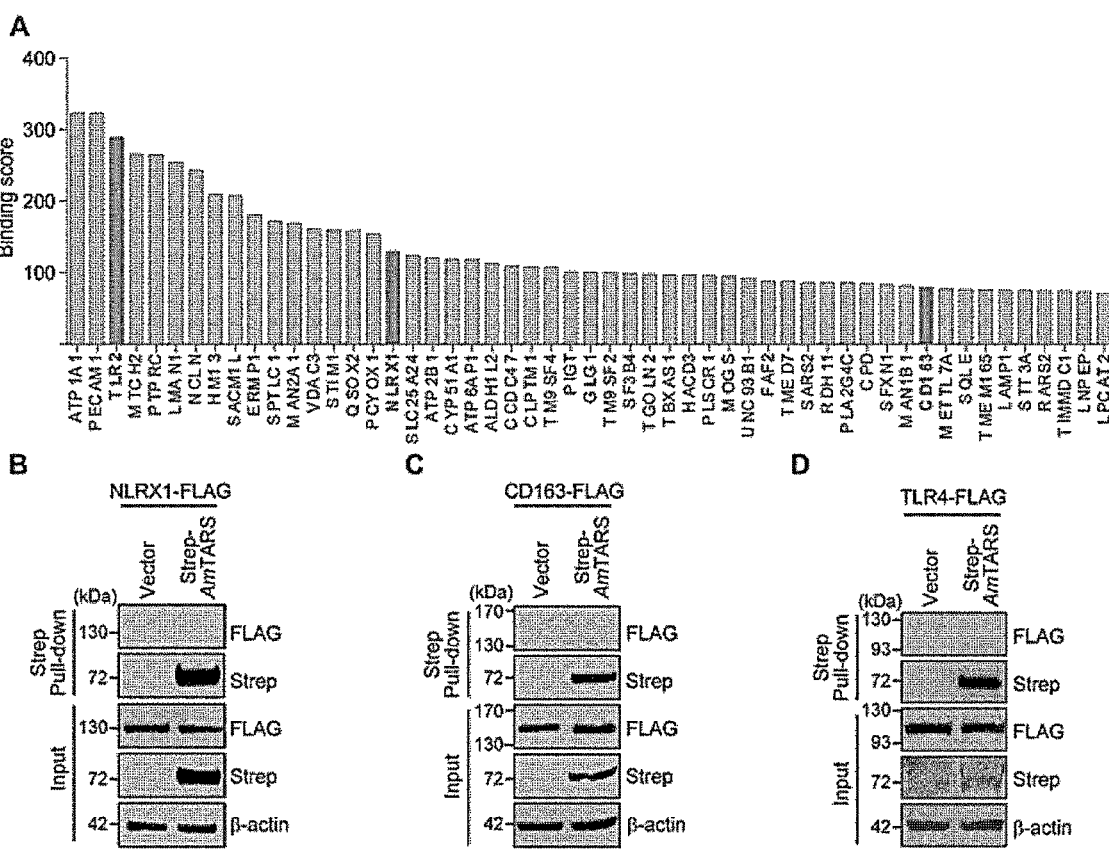

FIG. 27 shows that interactome analysis of AmTARS. (A) AmTARS-interacting candidates identified from membrane protein interactome analysis. Potential interactors (receptors) involved in innate immunity are indicated in red. (B-D) Pull-down of Strep-AmTARS co-expressed with NLRX1-FLAG (B), CD163-FLAG (C), and TLR4-FLAG (D) in HEK 293T cells. Data shown are representative of three independent experiments, each with similar results.

Figure 28:
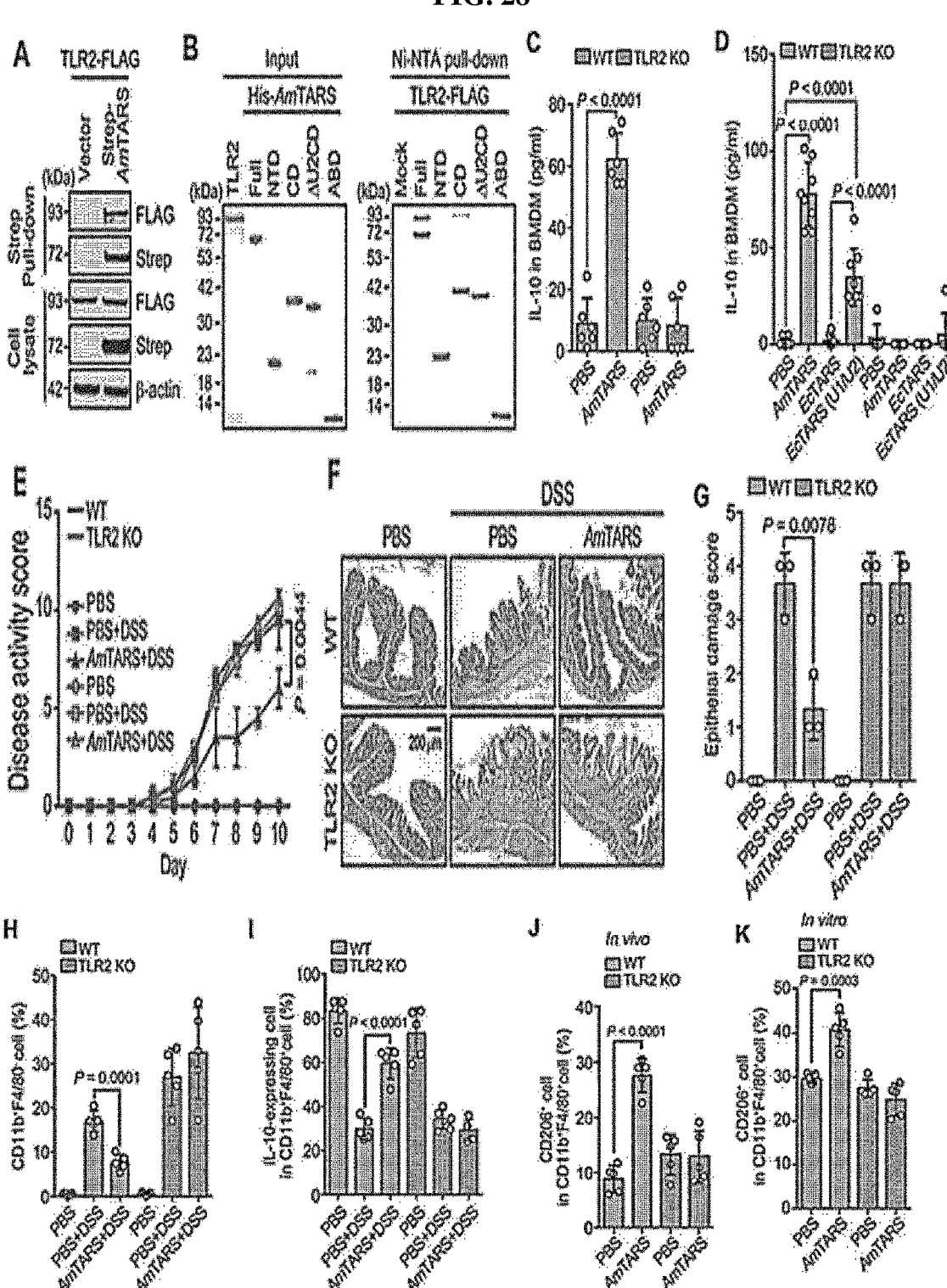

FIG. 28 shows that AmTARS is a TLR2-dependent anti-inflammatory immune mediator. (A and B) AmTARS interacts directly with TLR2. Pull-down assay using lysates of HEK 293T cells transfected with Strep-AmTARS and TLR2-FLAG (A). The proteins precipitated by an anti-Strep antibody were analyzed by western blotting. In vitro interaction assay using purified TLR2-FLAG and His-tagged AmTARS proteins (B). Purified TLR2-FLAG was mixed with purified His-tagged AmTARS protein. His-tagged protein was precipitated by Ni-NTA, eluted, and analyzed by SDS-PAGE. (C) TLR2-dependent anti-inflammatory function of AmTARS in BMDMs (n=6 per group). (D) The unique regions within AmTARS are essential for anti-inflammatory function in a TLR2-dependent manner (n=8 per wild-type group and n=6 per TLR2 KO group). BMDMs from WT or TLR2-KO mice were treated with the indicated proteins (C and D). (E-I) TLR2-dependent function of AmTARS in vivo. WT or TLR2-KO mice with DSS-induced colitis were injected with either PBS or AmTARS. Daily changes in disease activity scores (E). Intestinal epithelial damage, as analyzed by H&E staining (F), and damage scores (G) (n=3 per group). Percentage of infiltrated immune cells, gated on CD11b+F4/80− (monocytes) (H) and CD11b+F4/80+IL-10+ (IL-10-secreting macrophages) (I) (n=5 per group). (J and K) TLR2-dependent M2 macrophage polarization induced by AmTARS. WT or TLR2-KO mice were injected with either PBS or AmTARS (J). After 24 h, PECs were isolated, and the percentage of M2 macrophages (CD206+CD11b+F4/80+) was measured by flow cytometry. Percentage of M2 macrophages in BMDMs from WT or TLR2-KO mice treated for 24 h with either AmTARS or PBS (n=5 per group) (K). EcTARS, *E. coli* TARS; EcTARS (U1/U2), an engineered EcTARS incorporating the AmTARS U1 and U2 regions. Data shown in (A and B) are representative and repeated at least three times. Data shown in (C-E) and (G-K) are representative of three independent experiments, each with similar results (mean±SEM). P-values were calculated by an unpaired two-tailed Student's t-test.

Figure 29:
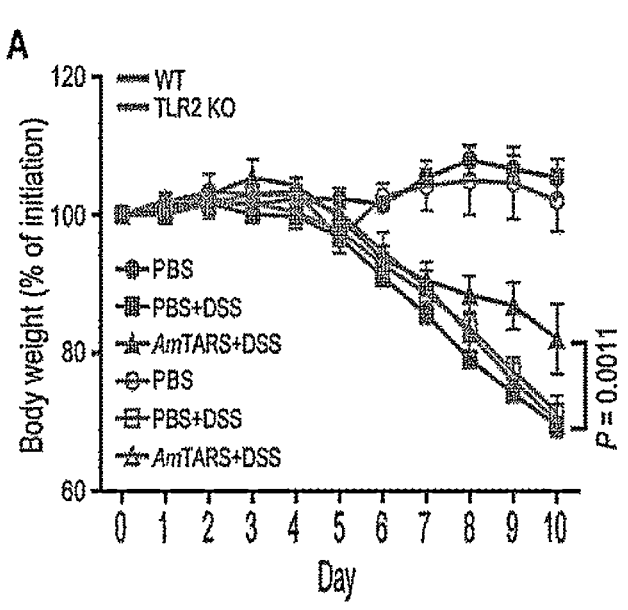
Figure 29:
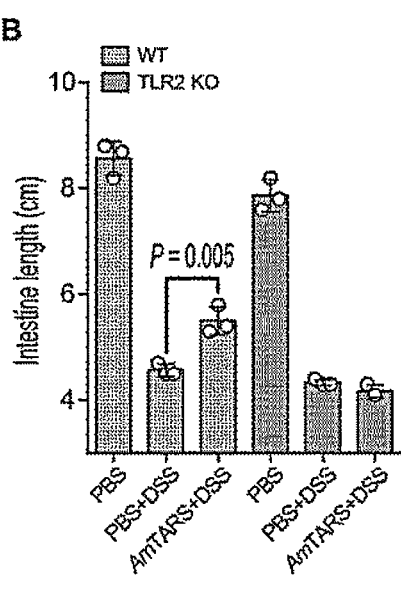

FIG. 29 shows that TLR2-dependent anti-inflammatory function of AmTARS. (A and B) DSS-induced colitis WT or TLR2-KO mice were treated with either AmTARS or PBS. Daily change in body weight (n=5 per group) (A) and measurement of intestine colon length (n=3 per group) (B). Data shown are representative of three independent experiments, each with similar results (mean±SEM). P-values were calculated by an unpaired, two-tailed Student's t-test.

Figure 30:
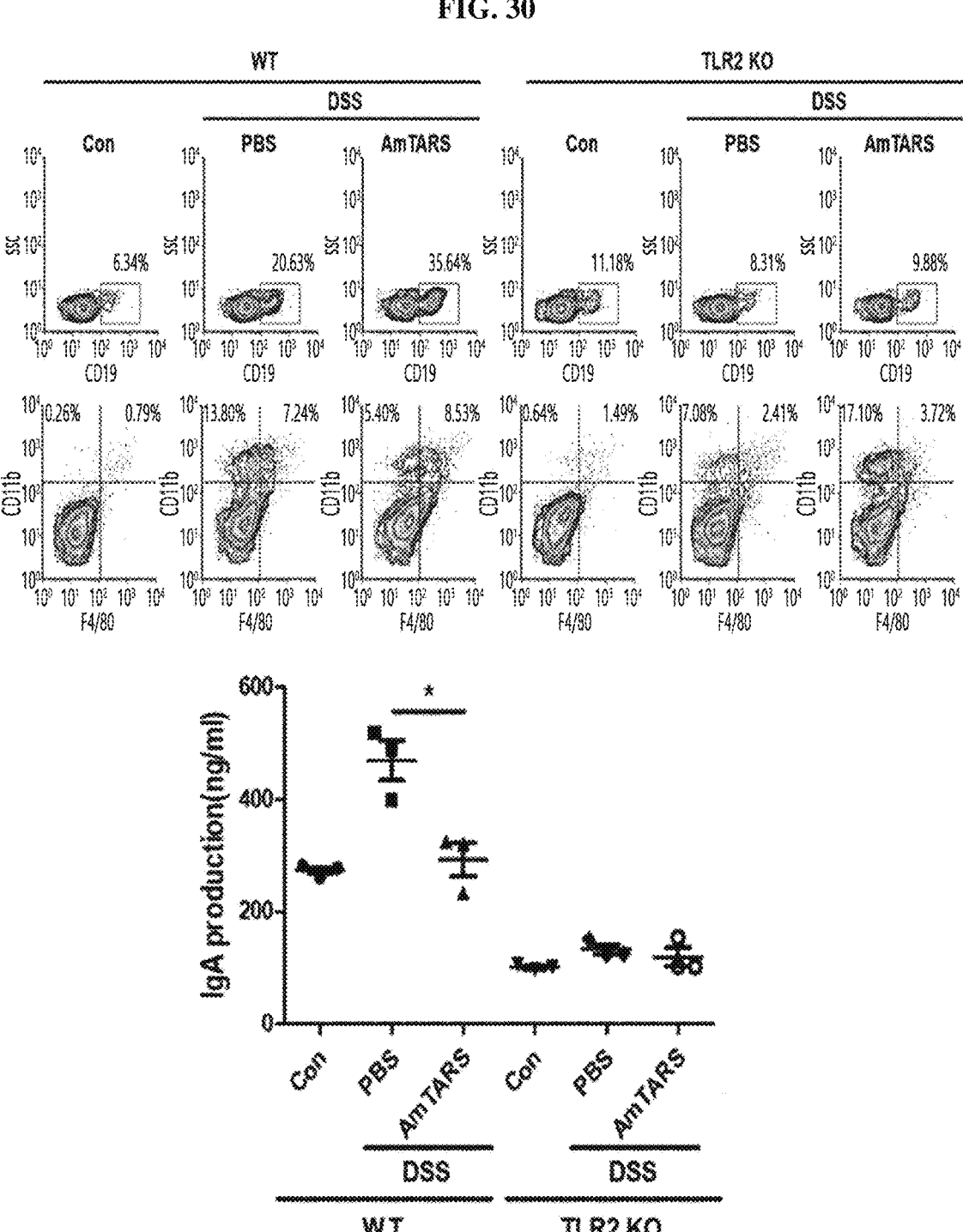

FIG. 30 shows the results of analyzing IgA and cell distribution changes according to AmTARS treatment in an inflammatory bowel disease-induced TLR2-deficient or normal mouse model.

Figure 31:
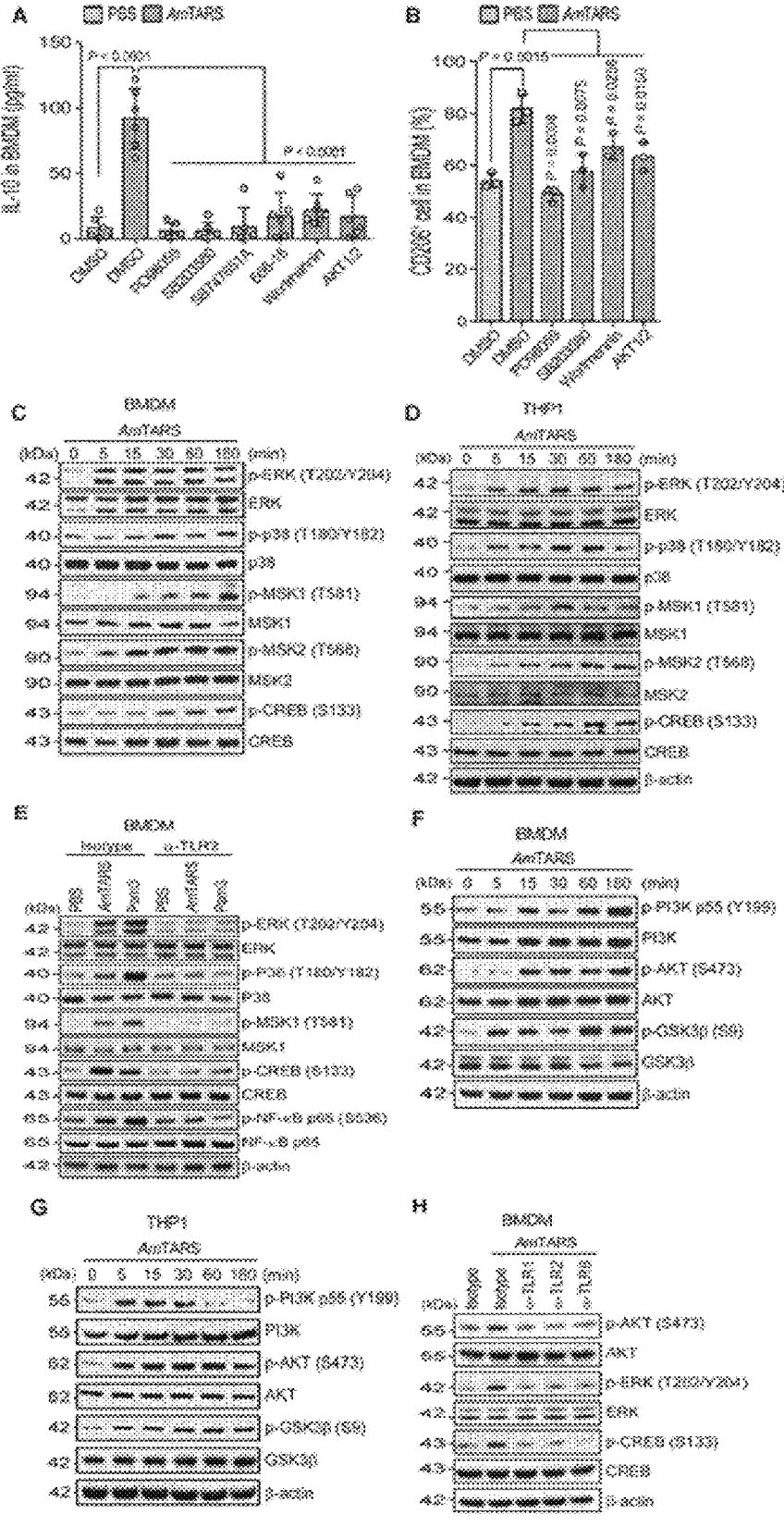

FIG. 31 shows that AmTARS efficiently promotes anti-inflammatory responses by activating CREB. (A and B) Analysis of key molecules that inhibit the MAPK and PI3K/AKT signaling pathways. IL-10 produced by BMDMs pre-treated with inhibitors of ERK (PD98059, 10μ), p38 (SB203580, 10μ), MSK1/2 (SB747651A, 10 μM), CREB (666-15, 1 μM), PI3K (Wortmannin, 10 μM), and AKT1/2 (AKT1/2, 10 μM) for 1 h before treatment with either PBS or AmTARS for 24 h (n=6 per group) (A). Flow cytometry analysis of M2 macrophages in BMDMs pre-treated for 1 h with the indicated kinase inhibitors, before treatment with either PBS or AmTARS for 24 h (n=3 per group) (B). (C and D) Western blot analysis of MAPK signaling molecules in lysates of BMDMs (C) or THP1 cells (D) treated for different times with 0.5 μM AmTARS. (E) Western blot analysis of lysates of BMDMs pre-treated with α-IgG (Isotype, 1 μg ml-1) or α-TLR2 (1 μg ml-1) for 1 h before treatment with PBS, AmTARS (0.5 μM), or Pam3 (0.5 μM) for 30 min. (F and G) Western blot analysis of PI3K/AKT signaling molecules in lysates of BMDMs (F) or THP1 cells (G) treated with 0.5 μM AmTARS. (H) AmTARS activates both TLR2/1- and TLR2/6-mediated signaling. Activation of AKT, ERK, and CREB was measured by western blot analysis of lysates of THP1 cells pre-treated with α-IgG, α-TLR1, α-TLR2, or α-TLR6 (1 μg ml-1) for 1 h before treatment for 30 min with PBS or AmTARS (0.5 UM). Data shown in (A and B) are representative of three independent experiments, each with similar results (mean±SEM). P-values were calculated using an unpaired two-tailed Student's t-test. Data shown in (C-H) are representative and repeated at least three times.

Figure 32:
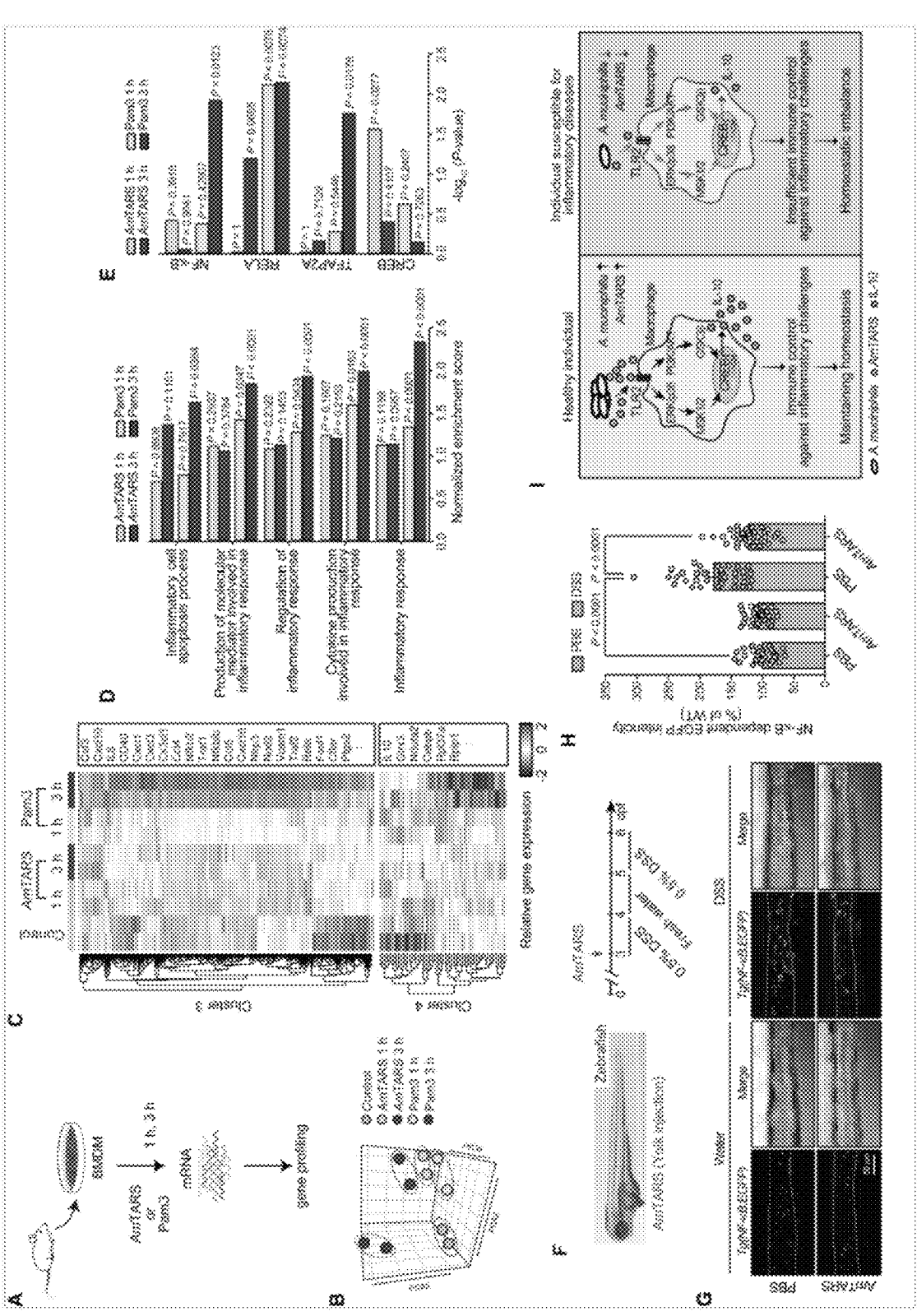

FIG. 32 shows that AmTARS is a steady-state, immune homeostatic mediator. (A-E) Global gene expression analysis. Total mRNA from BMDMs treated with either AmTARS (0.5 μM) or Pam3 (10 ng ml-1) for 1 or 3 h was isolated and analyzed by RNA sequencing (A). Principle components analysis (PCA) of the gene expression profiles for each sample (B). Hierarchical clustering of gene expression profiles from each sample identified cluster 3 and 4 (C). Gene set enrichment analysis (GSEA) of clusters 3 and 4 with respect to terms related to inflammation (D). GSEA was performed for up-regulated genes using Enrichr to identify terms associated with transcription factors (E). (F) Overview of the experimental procedures for zebrafish. The yolk of Tg (NFκB:EGFP) transgenic zebrafish larvae (3 dpf) was injected with PBS or AmTARS. Injected larvae were treated at 3 and 5 dpf with 0.5% DSS for 24 h, with a washing period with fresh water for 24 h in between. Sample collection and analysis of Tg (NFκB:EGFP)-based EGFP intensity were conducted at 6 dpf. (G) Representative confocal images showing NF-κB signaling in the mid-distal intestines of PBS- or AmTARS-injected larvae with or without DSS treatment. White dashed lines denote the boundaries of the intestines (based on merged DIC bright field images). (H) Bar graph comparing the fluorescence intensity of the mid-distal intestines of PBS- or AmTARS-injected larvae treated (or not) with DSS (n=32 per PBS group and n=35 per DSS group). (I) Schematic model of the role of AmTARS in maintaining immune homeostasis via TLR2-mediated anti-inflammatory signaling pathways. Data shown in (A-C) are representative and repeated twice. Data shown in (H) are representative of three independent experiments, each similar results (mean±SEM). P-values were calculated by unpaired and two-tailed Student's t-test.

Figure 33:
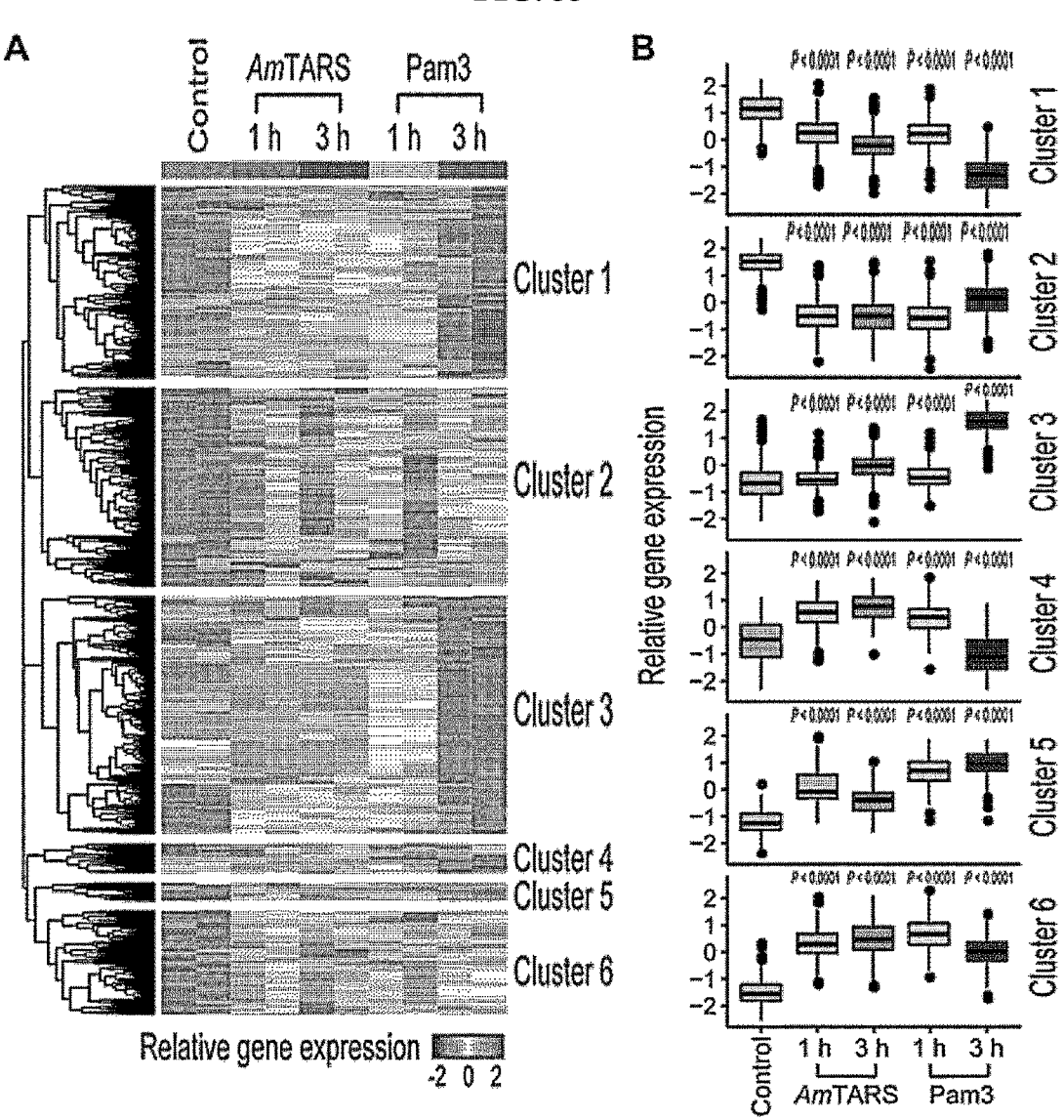

FIG. 33 shows that AmTARS regulated gene expression differs from that of the typical TLR2 agonist Pam3CSK4. (A) Hierarchical clustering of gene expression profiles in BMDMs treated with 0.5 μM AmTARS or 10 ng ml-1 Pam3 for 1 or 3 h (n=2 per group). (B) The genes corresponding to each cluster are summarized in a boxplot, along with relative gene expression. Data are representative and repeated twice. The P-values were calculated using the Wilcoxon signed-rank test (control vs. each condition) (B).

Figure 34:
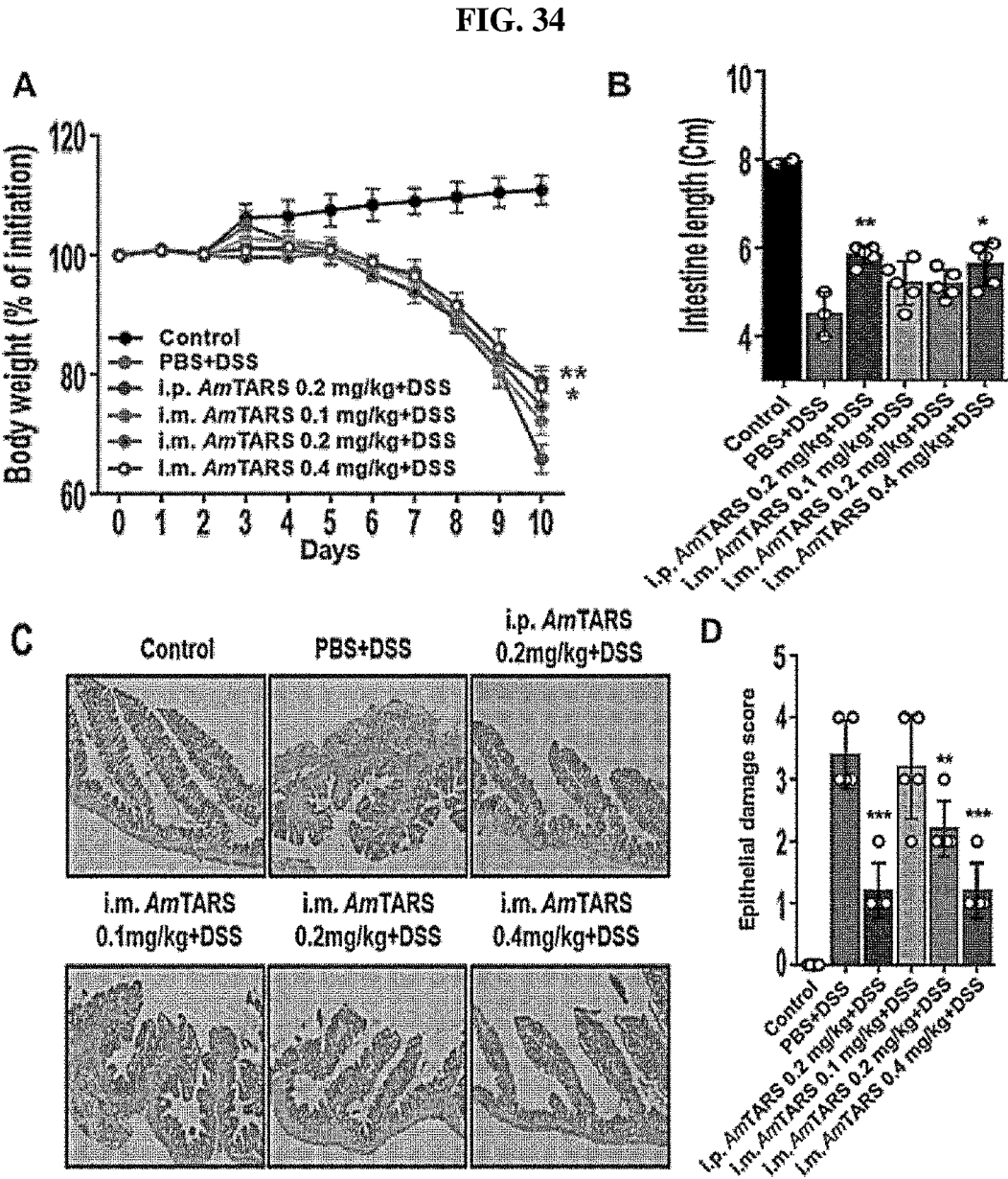

FIG. 34 shows that intramuscular injection of AmTARS also improves physiological signs in DSS-induced colitis mice. (A-D) Normal or DSS-induced colitis mice injected intraperitoneally (i.p.) and intramuscularly (i.m) with PBS or AmTARS. Daily changes in Body weight (A) intestine length (B). Representative hematoxylin and eosin staining (H&E) of proximal regions of the colon (C), and epithelial damage scores (n=5 per group) (D).

BEST MODE FOR CARRYING OUT THE INVENTION

The present invention will be specifically described as follows. Each description and exemplary embodiment disclosed herein may also be applied to other descriptions and exemplary embodiments. That is, all combinations of various elements disclosed herein fall within the scope of the present invention. Furthermore, the scope of the present invention is not limited by the specific description below.

In accordance with an aspect of the present invention, there is provided a pharmaceutical composition for prevention or treatment of an inflammatory disease, the pharmaceutical composition containing *Akkermansia muciniphila*-derived threonyl-tRNA synthetase (TARS) or a fragment thereof as an active ingredient.

As used herein, the term "threonyl-tRNA synthetase (TARS)" is one of aminoacyl-tRNA synthetases (AARSs), enzymes that attach amino acids to transport RNA (tRNA) in the initial stage of protein synthesis, and some of human-derived AARS proteins are known to be secreted from cells to perform various functions. Typically, it is known that in a specific environment, human tyrosyl-tRNA synthetase (YARS) is secreted from cells to perform a function as a cytokine and human lysyl-tRNA synthetase (KARS) stimulates immune cells to promote the inflammatory response. Particularly, it has been reported that human threonyl-tRNA synthetase (TARS), when secreted from cells, induces angiogenesis via an inflammatory signal and, in pancreatic cancer cells, increases the synthesis of mucin 1 (MUC1), one of the major proteins of mucin containing a large amount of threonine. Additionally, TARS has been reported as a key component of vertebrate-specific protein synthesis initiation complexes needed for protein synthesis of genes necessary for development of blood vessels, the nervous system, and the like during the evolution from invertebrates to vertebrates.

In the present invention, the TARS may be derived from human gut bacteria, specifically *Akkermansia* sp., and more specifically *Akkermansia muciniphila*, but is not limited thereto. The TARS may include, for example, the amino acid sequence of SEQ ID NO: 1, but is not limited thereto. The TARS comprises a protein comprising the amino acid sequence of SEQ ID NO: 1, a protein having the amino acid sequence of SEQ ID NO: 1, and a protein consisting of the amino acid sequence of SEQ ID NO: 1.

In the present invention, SEQ ID NO: 1 means an amino acid sequence having TARS activity. Specifically, SEQ ID NO: 1 may be a sequence of a protein having have TARS activity encoded by a gene encoding TARS. According to an aspect of the present invention, the protein may be derived from specifically, *Akkermansia* sp., and more specifically *Akkermansia muciniphila*, but is not limited thereto, and any sequence that has the same activity as in the amino acid may be included without limitation. The amino acid sequence of SEQ ID NO: 1 may be obtained from GenBank, a known database (GenBank: ACD05550.1). The TARS may be used interchangeably with *Akkermansia muciniphila*-derived TARS (AmTARS).

Although the protein having TARS activity in the present invention is defined as a protein including the amino acid sequence of SEQ ID NO: 1, the addition of a meaningless sequence upstream or downstream of the nucleotide sequence of SEQ ID NO: 1, a mutation that may occur naturally, or a silent mutation thereof is not excluded. It is obvious to a person skilled in the art that any protein that has an activity identical or corresponding to that of the protein including the amino acid sequence of SEQ ID NO: 1 corresponds to the protein having TARS activity of the present invention.

Specifically, the protein having TARS activity of the present invention may be a protein consisting of the amino acid sequence of SEQ ID NO: 1 or an amino acid sequence having at least 70%, 80%, 85%, 90%, 95%, 96%, 97%, 98%, or 99% homology or identity with the amino acid sequence of SEQ ID NO: 1. In addition, it is obvious that any protein that consists of an amino acid sequence with a deletion, a modification, a substitution, or an addition in a part thereof may also fall within the scope of the protein of the present invention as long as the amino acid sequence has such a homology or identity and shows efficacy corresponding to that of the above protein.

That is, although described as "protein or polypeptide consisting of an amino acid sequence set forth in a particular sequence number" herein, any protein that consists of an amino acid sequence having a deletion, a modification, a substitution, or an addition in a part thereof may also be used in the present invention as long as the peptide has an activity identical or corresponding to that of the polypeptide consisting of the amino acid sequence of the corresponding sequence number. For example, it is obvious that any polypeptide that has an activity identical or corresponding to that of the "polypeptide consisting of the amino acid sequence of SEQ ID NO: 1" may also fall within the "polypeptide consisting of the amino acid sequence of SEQ ID NO: 1".

As used herein, the term "homology" or "identity" refers to a percentage of identity between two polynucleotide or polypeptide moieties. The homology between sequences from one moiety to another moiety may be determined by a known technique in the art. For example, the homology between two moieties may be determined by directly aligning sequence information between two polynucleotide molecules or two polypeptide molecules by using an easily accessible computer program capable of aligning sequence information. Additionally, the homology between polynucleotides may be determined by hybridizing the polynucleotides under conditions in which a stable double strand is formed between homologous regions and then decomposing the hybridized polynucleotides via a single-strand-specific nuclease to deciding the size of the decomposed fragments.

In the present invention, the gene encoding TARS may be derived from bacteria, specifically *Akkermansia* sp., and more specifically, *Akkermansia muciniphila*, but any *Akkermansia* sp. microbe that can express the gene encoding TARS may not be particularly limited. The gene encoding TARS may include a nucleotide sequence encoding the amino acid sequences of SEQ ID NO: 1, and more specifically, the nucleotide sequence of SEQ ID NO: 2, but is not limited thereto. The nucleotide sequence of SEQ ID NO: 2 may be obtained from GenBank, a known database (GenBank: CP001071.1).

As used herein, the term "polynucleotide" refers to a nucleotide polymer composed of nucleotide monomers covalently bonded in a chain, and examples thereof are a DNA or RNA strand having a predetermined length or longer. More specifically, the term refers to a polynucleotide fragment encoding the variant.

Specifically, in the polynucleotide of the present invention, various modifications may be made in a coding region within the range in which the amino acid sequence of the polypeptide is not changed, due to codon degeneracy or in consideration of the codons preferred by an organism in which the polypeptide is to be expressed. Specifically, any polynucleotide that encodes TARS of the present invention may be included without limitation.

In addition, any probe that can be prepared from a known gene sequence, for example, any sequence that can hybridize with a complementary sequence to a part or the entirety of the nucleotide sequence under stringent conditions to encode the protein having TARS activity of the present invention may be included without limitation. The term "stringent condition" refers to a condition that enables specific hybridization between polynucleotides. Such conditions are well known in the art. For example, the conditions may include conditions under which genes having high homology or identity, such as, genes having at least 40%, specifically at least 90%, more specifically at least 95%, still more specifically at least 97%, and still more specifically at least 99% homology or identity hybridize with each other but genes having lower homology or identity do not hybridize with each other; or typical washing conditions for southern hybridization, i.e., washing is conducted one time, specifically, two or three times at a salt concentration and temperature corresponding to 60° C., 1×SSC, and 0.1% SDS, specifically 60° C., 0.1×SSC, and 0.1% SDS, and more specifically 68° C., 0.1×SSC, and 0.1% SDS.

Hybridization requires that two nucleic acids have complementary sequences, although mismatches between nucleotides may be possible depending on hybridization stringency. The term "complementary" is used to describe the relationship between nucleotide bases that can hybridize with each another. For example, as for DNA, adenosine is complementary to thymine, and cytosine is complementary to guanine. Therefore, the present invention may include not only substantially similar nucleic acid sequences but also isolated nucleic acid fragments complementary to the entire sequence.

Specifically, polynucleotides having homology or identity can be detected using hybridization conditions including a hybridization step at a Tm value of 55° C. under the above-described conditions. In addition, the Tm value may be 60° C., 63° C., or 65° C., but is not limited thereto, and may be appropriately controlled by a person skilled in the art according to the purpose.

The appropriate stringency for hybridizing polynucleotides depends on the length of the polynucleotides and the degree of complementarity thereof, and variables thereof are well known in the art.

As for the amino acid or nucleotide sequence in the present invention, the term "fragment" refers to a part of a parent sequence. For example, the fragment may be a polypeptide in the form in which one or more amino acids are removed from the C or N terminus of the parent sequence.

In the present application, "fragment" of an enzyme may refer to "functional fragment". The "functional fragment" may also be referred to as an active ingredient, and means a polypeptide that is a part of a parent enzyme and has enzymatic activity of the parent enzyme. For example, the functional fragment of the enzyme may include a catalytic site of the enzyme.

The fragment of the enzyme may include a part of the full length of the parent enzyme. For example, the fragment of the enzyme may include amino acids of at least about 20%, 30%, 40%, 50%, 60%, 70%, 80%, 90%, 95%, 98%, or 99%, or less than 100% of the full length of the parent enzyme, but is not limited thereto.

In the present invention, the fragment of TARS may mean the amino acid sequence of the above-described *Akkermansia muciniphila*-derived TARS or a part of the polynucleotide sequence encoding the same, and any sequence that is derived from *Akkermansia muciniphila*-derived TARS or a part of the polynucleotide sequence encoding the same may be included without limitation.

Specifically, the fragment of TARS may be derived from the amino acid sequence of SEQ ID NO: 1 or the nucleotide sequence of SEQ ID NO: 2, and more specifically, may include at least one amino acid sequence selected from SEQ ID NO: 3, which is the sequence corresponding to 99th to 113rd amino acids of SEQ ID NO: 1, and SEQ ID NO: 4, which is the sequence corresponding to 290th to 312nd amino acids of SEQ ID NO: 1. Alternatively, polynucleotide sequences encoding a fragment of TARS may include at least one polynucleotide sequence selected from SEQ ID NO: 5, which is the sequence corresponding to the 295th to 339th nucleotides of SEQ ID NO: 2, and SEQ ID NO: 6, which is the sequence corresponding to the 868th to 936th nucleotides of SEQ ID NO: 2.

Specifically, TARS or a fragment thereof of the present invention may be a peptide consisting of 14 to 630 consecutive amino acids in the amino acid sequence of SEQ ID NO: 1, including SEQ ID NO: 3 and/or SEQ ID NO: 4. As one example, the peptide may be a peptide including the amino acid sequence of SEQ ID NO: 3 or 4. As another example, the TARS of the subject application or a fragment thereof comprises the amino acid sequences of SEQ ID NOs: 3 and 4, and may comprise the structural sequence of a TARS derived from other microorganisms. If the structural sequence of a TARS is derived from a microorganism, the sequence thereof is not particularly limited. Further, any structural sequence of the TARS of a microorganism known in the art may be included in the scope of the subject application. For example, the TARS of the subject application or a fragment thereof may comprise the amino acid sequence of SEQ ID NOs: 3 and/or 4, and may comprise the structural sequence of the TARS derived from *E. coli*, but is not limited thereto.

As used herein, the term "corresponding to" refers to an amino acid residue at a position recited in a polypeptide, or an amino acid residue similar, identical, or homologous to a residue recited in a polypeptide. Identifying an amino acid at a corresponding position may be determining a particular amino acid of a sequence referring to a particular sequence. As used herein, the term "corresponding region" generally refers to a similar or corresponding site in a related protein or reference protein.

For example, any amino acid sequence is aligned with SEQ ID NO: 1, and based on this, each amino acid residue of the amino acid sequence may be numbered with reference to an amino acid residue numerical position corresponding to an amino acid residue of SEQ ID NO: 1. For example, a sequence alignment algorithm as described in the present invention may identify the position of an amino acid or a position of occurrence of a modification, such as a substitution, an insertion, or a deletion, compared with a query sequence (also referred to as a "reference sequence").

For such alignment, for example, the Needleman-Wunsch algorithm (Needleman and Wunsch, 1970, *J. Mol. Biol.* 48:443-453) or Needle program of the EMBOSS package (EMBOSS: The European Molecular Biology Open Software Suite, Rice et al., 2000, *Trends Genet.* 16:276-277) may be used, but without limitation thereto, a sequence alignment program, a pairwise sequence comparison algorithm, or the like, which are known in the art, may be used as appropriate.

TARS or a fragment thereof of the present invention exhibits an anti-inflammatory effect and can be used for prevention or treatment of an inflammatory disease.

As used herein, the term "inflammatory disease" collectively refers to a disease having inflammation as a major lesion.

Examples of the inflammatory disease may include inflammatory bowel disease (IBD), edema, dermatitis, conjunctivitis, periodontitis, rhinitis, otitis media, pharyngitis, tonsillitis, pneumonia, gout, sacrificial spondylitis, gastritis, psoriatic arthritis, osteoarthritis, periarthritis, tendinitis, tenosynovitis, myositis, hepatitis, lymphangeitis, felon, urinary tract infection, peritonitis, cystitis, nephritis, respiratory disease, and sepsis, and specifically, may be inflammatory bowel disease, and more specifically, may be at least one selected from the group consisting of colitis, ulcerative colitis, Crohn's disease, and Behçet's enteritis, but is not limited thereto.

The inflammatory disease of the present invention may include an immune disease, a metabolic disease, and an infectious disease, which are accompanied by inflammation.

Examples of the "immune disease accompanied by inflammation" are autoimmune disease, transplant rejection, graft-versus-host disease, and the like. Specifically, examples of the autoimmune disease may include atopy, allergy, rheumatoid arthritis, Hashimoto's thyroiditis, multiple sclerosis, endometriosis, psoriasis, asthma, hypothyroidism, hyperthyroidism, Behçet's disease, myasthenia gravis, Meniere's syndrome, Guillain-Barre syndrome, Sjogren's syndrome, vitiligo, systemic scleroderma, and the like, and specifically may be inflammatory bowel disease, and more specifically may be at least one selected from the group consisting of atopy, allergy, rheumatoid arthritis, Hashimoto's thyroiditis, multiple sclerosis, endometriosis, psoriasis, hypothyroidism, hyperthyroidism, and asthma, but is not limited thereto.

Search results have been recently reported that a metabolic disease is caused by increased expression of inflammatory factors, and thus the metabolic disease may be caused by inflammation or accompanied by inflammation. Examples of the "metabolic disease accompanied by inflammation" may include obesity, diabetes, insulin resistance, abnormal lipid metabolism, hypertriglyceridemia, increased free fatty acids, reduced high-density cholesterol, hypertension, and various complications resulting therefrom, and the like, and specifically may be at least one selected from the group consisting of obesity and diabetes, but is not limited thereto.

The "infectious disease accompanied by inflammation" refers to an inflammatory disease caused by the spread or invasion of a disease-causing pathogen, such as virus, bacterium, fungus, and parasite, to animals or humans. The inflammatory disease is as described above.

In the present invention, the TARS or a fragment thereof can increase the secretion of IL-10.

In addition, the TARS or a fragment thereof can reduce the secretion of IL-6 and/or TNF-$\alpha$.

In an embodiment of the present invention, when bone marrow-derived macrophages (BMDM) as mouse-derived immune cells and human macrophages THP1 as human-derived immune cells were treated with TARS in a non-inflammatory or inflammatory environment, the inflammatory cytokines IL-6 and TNF-$\alpha$ were not or less secreted, while the inflammatory cytokine IL-10 was increasingly secreted in a dose-dependent manner based on AmTARS (FIGS. 2 to 6).

These results confirmed that TARS induced an inflammatory disease alleviating effect by increasing the secretion of IL-10 and reducing the secretion of IL-6 and/or TNF-$\alpha$.

The above-described effect of increasing IL-10 secretion and reducing the secretion of IL-6 and/or TNF-$\alpha$ may be exerted specifically by *Akkermansia muciniphila*-derived TARS.

In an embodiment of the present invention, to determine whether TARS from other bacteria in the human microbiome and TARS secreted from human cells perform similar functions to *Akkermansia muciniphila*-derived TARS, TARSs (respectively, BfTARS, eTARS, RbTARS, and hTARS) derived from *Bacteroides fragilis, Escherichia coli*, and *Ruminococcus bromii*, which are strains in the human microbiome, and *Homo sapiens* were purified and applied to BMDM in a non-inflammatory or inflammatory environment, and as a result, the secretion of the inflammatory cytokine IL-10 was specific to *Akkermansia muciniphila*-derived TARS (FIG. 17), and IL-10 was increased in a protein concentration-dependent manner in *Akkermansia muciniphila*-derived TARS treatment groups while the secretion of IL-10 was not significantly increased compared with the LPS treatment control in the other species-derived TARSs (BfTARS, eTARS, and hTARS) (FIG. 17).

In addition, the above-described anti-inflammatory effect of TARS may be exerted from a fragment of TARS.

In an embodiment of the present invention, as a result of investigating the immune cytokine secretion by treatment with TARS, functional site 1 (R1, SEQ ID NO: 3), functional site 2 (R2, SEQ ID NO: 4), and Tat-function site 1 (Tat-R1) and Tat-function site 2 (Tat-R2) obtained by adding, to the functional sites, Tat tag, which is a tag for favorable delivery into cells, TARS, R2, and Tat-R2 reduced the secretion of IL-6 and increased the secretion of IL-10 in the created inflammatory environment (FIG. 22).

When the concentrations of functional site 2 were 100 µM, 200 µM, 300 µM in the same conditions, the secretion of IL-6 was reduced and the secretion of IL-10 was increased by all of R2 100 µM and 300 µM and Tat-R2 100 µM, 200 µM, and 300 µM.

Of these, the secretion of IL-10 was increased by 2-fold in the Tat-R2 treatment groups compared with TARS.

These results confirmed that the TARS-specific regulation of immune cytokine secretion was exerted by a fragment of TARS.

In the present invention, the TARS or a fragment thereof can inhibit inflammatory responses and increase inflammatory cytokine production by regulating the phosphorylation of intracellular signal transducers.

In an embodiment of the present invention, the signal transducers affected by TARS treatment were p38, c-Jun N-terminal kinase (JNK), and nuclear factor kappa-light-chain-enhancer of activated B cells (NF-kB), while extracellular signal-regulated kinase (ERK) was not affected thereby. JNK was affected through the regulation of phosphorylation from 30 min after TARS treatment, and p38 and NF-kB showed distinctive differences in the level of phosphorylation compared with a control from 2 h after TARS treatment (FIG. 7).

In the present invention, the TARS or a fragment thereof can affect the regulation of metabolic disease-associated intracellular signaling.

In an embodiment of the present invention, the treatment of mouse adipocyte 3T3-L1 with insulin resulted in the phosphorylation of protein kinase B (AKT), and the treatment with insulin and PMA reduced the phosphorylation compared with the treatment with insulin alone. However, the treatment with ARS after the treatment with insulin and PMA again increased the phosphorylation (FIG. 8).

In addition, when insulin resistance was induced by TNF-$\alpha$ treatment, the phosphorylation of AKT was reduced by even the treatment with insulin, and the phosphorylation was increased by the further treatment with TARS. In the same experiment, glycogen synthase kinase (GSK)-3$\beta$, a downstream signal transducer of AKT, was phosphorylated and inhibited, and S6 kinase (S6K), affected by mammalian target of rapamycin (mTOR) complex 1 (mTORC1), was phosphorylated and activated (FIG. 9).

In the present invention, the TARS or a fragment thereof can increase B cells. In an embodiment of the present invention, as a result of administering TARS to an inflammatory bowel disease mouse model, the secretion of the cytokine IL-10 in the plasma was increased and the amount of IgA increased due to an inflammation response was reduced. Additionally, the distribution of B cells that have been reported to play an important role in alleviating inflammatory bowel disease, was significantly increased by TARS administration (FIG. 14).

However, a B cell-deficient inflammatory bowel disease mouse model, unlike normal mice with no deficiency of B cells, did not show a reduction in the intestine length and an alleviation of the colon tissue damage, an increase in B cells by TARS, and the expression of IgA secreted from B cells (FIGS. 15 and 16).

These results confirmed that TARS increased the distribution of B cells in the colon to induce an inflammatory bowel disease alleviation effect.

In addition, the anti-inflammatory function of the TARS or a fragment thereof was exerted through the interaction with Toll-like receptor 2 (TLR2) (FIGS. 25 to 30).

In the present invention, the TARS or a fragment thereof can increase macrophages.

In addition, the TARS and the fragment thereof can promote the differentiation of macrophages into M2 microphages.

In an embodiment of the present invention, TARS bound to macrophages but did not bind to the other cells including B cells, and on the basis of this, as a result of, on the basis of the results, determining whether the anti-inflammatory efficacy of TARS was exhibited via macrophages in a macrophage-deficient inflammatory bowel disease mouse model, the distribution of B cells in the colon was not increased by TARS in the macrophage-deficient mice, and the proportion of M2 macrophages, anti-inflammatory macrophages, reduced by an inflammatory response, was increased by TARS.

In another embodiment of the present invention, the proportion of macrophage differentiating into anti-inflammatory macrophages was significantly increased by TARS.

These results confirmed that TARS promoted the differentiation of M2 macrophages, anti-inflammatory macrophages, to result in IL-10 secretion, which was then used as a signal to increase the distribution of B cells, thereby systemically inducing the anti-inflammatory function.

The present invention has significance for first confirming that among AARS of *Akkermansia muciniphila* strains, especially TARS has an effect of preventing, alleviating, or treating various inflammatory diseases.

In particular, TARSs derived from *Bacteroides fragilis, Escherichia coli*, and *Ruminococcus bromii*, which are strains in the human microbiome, and *Homo sapiens* are proteins having the same function as *Akkermansia muciniphila*-derived TARS, but exhibited a different effect on the secretion of inflammatory or anti-inflammatory cytokines from *Akkermansia muciniphila*-derived TARS, and therefore *Akkermansia muciniphila*-derived TARS according to the present invention had a significant effect on the prevention, alleviation, or treatment of inflammatory diseases.

As used herein, the term "prevention" refers to all actions that inhibit or delay the outbreak of an inflammatory disease by administration of the composition of the present invention, and the term "treatment" refers to all actions that alleviates or favorably change the symptoms of an inflammatory disease by administration of the composition.

The pharmaceutical composition containing *Akkermansia muciniphila*-derived TARS or a fragment thereof of the present invention may further contain an appropriate carrier, excipient, or diluent that is commonly used in the preparation of a pharmaceutical composition. The content of *Akkermansia muciniphila*-derived TARS or a fragment thereof contained in the composition may include, but is not particularly limited to, 0.0001 wt % to 10 wt %, and preferably 0.001 wt % to 1 wt %, relative to the total weight of the composition.

The pharmaceutical composition may have any one formulation selected from the group consisting of a tablet, pills, a powder, granules, a capsule, an oral liquid preparation, a syrup, a sterile aqueous solution, a non-aqueous solvent, a suspension, an emulsion, a lyophilized preparation, and a suppository, or may have several oral or parenteral formulations. The composition, when formulated as a preparation, may be formulated using a diluent or an excipient, such as a filler, an extender, a binder, a wetting agent, a disintegrant, or a surfactant, which are commonly used. Exemplary solid preparations for oral administration include a tablet, pills, a powder, granules, a capsule, and the like, and such solid preparations may be prepared by mixing at least one compound with at least one excipient, for example, starch, sucrose, or lactose, gelatin, or the like. Lubricants, such as magnesium stearate and talc, may also be used in addition to simple excipients. Exemplary liquid preparations for oral administration correspond to a suspension, an oral liquid preparation, an emulsion, a syrup, and the like, and may contain simple diluents that are frequently used, such as water and liquid paraffin, as well as several excipients, such as a wetting agent, a sweetener, an aroma, and a preservative. Exemplary preparations for parenteral administration include a sterile aqueous solution, a non-aqueous solvent, a suspension, an emulsion, a lyophilized preparation, and a suppository. Examples of the non-aqueous solvent and suspension may include propylene glycol, polyethylene glycol, a vegetable oil such as olive oil, an injectable ester such as ethylolate, and the like. Exemplary base materials for the suppository may include Witepsol, Macrogol, TWEEN 61 (Polysorbate 61), cocoa butter, laurin butter, glycerogelatin, and the like.

The composition of the present invention may be administered at a pharmaceutically effective amount.

As used herein, the term "pharmaceutically effective amount" refers to an amount sufficient to treat a disease at a reasonable benefit/risk ratio applicable to medical treatment, and the level of the effective dose may be determined depending on the subject's type, the disease severity, the subject's age and sex, the type of the disease, the activity of the drug, sensitivity to the drug, the time of administration, the route of administration, excretion rate, the duration of treatment, factors including drugs used in combination with the composition, and other factors well known in the medical field. The composition of the present invention may be administered as an individual therapeutic agent or in combination with other therapeutic agents, and may be sequentially or simultaneously administered together with a conventional therapeutic agent. In addition, the composition may be administered once or multiple times. It is important to administer the composition at an amount to obtain the maximum effect with a minimum amount and without side effects considering all of the above factors, and such an amount may be easily determined by a person skilled in the art. A preferable dose of the composition of the present invention varies depending on the condition and body weight of a patient, severity of the disease, the dosage form of the drug, and the route and period of administration; however, for a preferred effect, the *Akkermansia muciniphila*-derived TARS or fragment thereof of the present invention may be administered daily in an amount of 0.0001 µg/kg to 100 µg/kg, and preferably 0.001 µg/kg to 100 µg/kg. The administration may be carried out once or several times in divided doses a day. The composition may be administered to various mammals, such as rats, livestock, and humans, through various routes, and the manner of administration is included without limitation as long as the manner is commonly used in the art, and for example, the composition may be administered orally, rectally, or by intravenous, intramuscular, subcutaneous, intrauterine dura, or intracerebroventricular injection.

The pharmaceutical composition of the present invention may be used in the form of veterinary medicines as well as pharmaceuticals applied to humans.

In accordance with another aspect of the present invention, there is provided a method for preventing or treating an inflammatory disease, the method including administering to a subject a composition including *Akkermansia muciniphila*-derived TARS or a fragment thereof as an active ingredient.

The terms used herein are as described above.

The term "subject" used herein refers to a mammal, including a human, that has an inflammatory disease or requires prevention or treatment of an inflammatory disease, and the administration of the pharmaceutical composition of the present invention to a subject suspected of having the inflammatory disease can efficiently treat the subject.

As used herein, the term "administration" refers to an introduction of the pharmaceutical composition of the present invention into a subject suspected of having an inflammatory disease by any suitable method, and the pharmaceutical composition may be administered through various oral or parenteral routes as long as the pharmaceutical composition can reach a target tissue.

The pharmaceutical composition of the present invention may be administered at a pharmaceutically effective amount, and the pharmaceutically effective amount is as described above.

The pharmaceutical composition of the present invention may be applied to any subject without particular limitation as long as the pharmaceutical composition has a purpose of preventing or treating an inflammatory disease of the subject. For example, the pharmaceutical composition may be applied to non-human animals, such as monkeys, dogs, cats, rabbits, marmots, rats, mice, cows, sheep, pigs, and goats, birds, fishes, and the like, and the pharmaceutical composition may be administered through parenteral, subcutaneous, intraperitoneal, intrapulmonary, and intranasal routes, and for topical treatment, if necessary, the pharmaceutical composition may be administered by any suitable method including intralesional administration. A preferable dose of the pharmaceutical composition of the present invention may vary depending on condition and body weight of a subject, severity of the disease, the dosage form of the drug, and the manner and period of administration, but may be appropriately selected by a person skilled in the art. For example, the pharmaceutical composition may be administered by oral, rectal, intravenous, intramuscular, subcutaneous, intrauterine dura, or intracerebrovascular injection, but is not limited thereto.

In accordance with still another aspect of the present invention, there is provided a composition for differentiation or proliferation of B cells, the composition containing *Akkermansia muciniphila*-derived TARS or a fragment thereof as an active ingredient.

The terms used herein are as described above.

The composition for differentiation or proliferation of B cells is an inducer for differentiation or proliferation of B cells and may further contain a substance known in the art in addition to the *Akkermansia muciniphila*-derived TARS or a fragment thereof, but is not limited thereto.

The effect of the TARS or a fragment thereof for the differentiation and proliferation of B cells is as described above.

In accordance with still another aspect of the present invention, there is provided a composition for differentiation or proliferation of M2 macrophages, the composition containing *Akkermansia muciniphila*-derived TARS or a fragment thereof as an active ingredient.

The terms used herein are as described above.

The composition for differentiation or proliferation of M2 macrophages is an inducer for differentiation or proliferation of M2 macrophages and may further contain a substance known in the art in addition to the *Akkermansia muciniphila*-derived TARS or fragment thereof, but is not limited thereto.

The effect of the TARS or fragment thereof for the differentiation and proliferation of M2 macrophages is as described above.

In accordance with still another aspect of the present invention, there is provided a food composition for prevention or alleviation of an inflammatory disease, the food composition containing *Akkermansia muciniphila*-derived TARS or a fragment thereof as an active ingredient.

The terms used herein are as described above.

As used herein, the "alleviation" refers to any action that alleviates or advantageously changes symptoms of a subject having or suspected of having an inflammatory disease by using the composition.

As a food-acceptable salt that may be contained in the food composition of the present invention, an acid addition salt formed by a food-acceptable free acid or a metal salt formed by a base is useful. As one example, an inorganic acid and an organic acid may be used as the free acid. Examples of the inorganic acid may include hydrochloric acid, sulfuric acid, bromic acid, sulfurous acid, or phosphoric acid, and examples of the organic acid may include citric acid, acetic acid, maleic acid, fumaric acid, gluconic acid, methanesulfonic acid, and the like. Examples of the metal salt may include an alkali metal salt or an alkaline earth metal salt, such as a sodium, potassium, or calcium salt. However, the present invention is not limited thereto.

The food composition of the present invention includes forms of pills, a powder, granules, an infusion, a tablet, a capsule, a liquid preparation, or the like, and exemplary foods that may include the composition may be various kinds of foods, for example, beverages, gums, teas, vitamin complexes, and health supplement foods.

As for ingredients that may be contained in the food composition of the present invention, the other ingredients other than the active ingredient as an essential ingredient are not particularly limited, and various herbal extracts, food supplements, or natural carbohydrates may be contained as additional ingredients, like in common foods. The content of the active ingredient in the food composition may be appropriately determined according to the purpose of use (prevention, alleviation, or therapeutic treatment). The content of the active ingredient contained in the composition is, but not particularly limited to, 0.0001 wt % to 10 wt %, and preferably 0.001 wt % to 1 wt %, relative to the total weight of the composition.

Examples of the food supplement additives include food supplement additives that are commonly used in the art, for example, flavours, savoury flavours, colorings, fillers, stabilizers, and the like.

Examples of the natural carbohydrates may include ordinary sugars, for example, monosaccharides, such as glucose and fructose; disaccharides, such as maltose and sucrose, and polysaccharides, such as dextrin and cyclodextrin; and sugar alcohols, such as xylitol, sorbitol, and erythritol. In addition to the above-described ingredients, natural flavours (e.g., rebaudioside A, glycyrrhizin, etc.) and synthetic flavours (saccharin, aspartame, etc.) may be advantageously used as the aroma.

Additionally, the food composition of the present invention may contain several types of nutrients, vitamins, minerals (electrolytes), savory flavors such as synthetic savory flavors and natural savory flavors, colorings, fillers (cheese, chocolate, etc.), pectic acid and salts thereof, alginic acid and salts thereof, organic acids, protective colloid thickeners, pH adjusters, stabilizers, preservatives, glycerin, alcohol, carbonating agents used for carbonated drinks, and the like. Additionally, the food composition of the present invention may contain fruit flesh for manufacturing natural fruit juice, fruit juice drinks, and vegetable drinks. These ingredients may be used either alone or in combination.

In the present invention, examples of the health supplement food may include a health functional food, a health food, and the like.

The functional food, being the same term as food for special health use (FoSHU), refers to a food with high medicinal and medical effects to efficiently exhibit a bioregulatory function in addition to a function of nutrient supply. The term "functional" refers to controlling nutrients for the structure or functions of the human body or providing beneficial effects to health purposes, such as physiological effects.

The food containing the food composition of the present invention may be manufactured by a method that is commonly used in the art, and in the manufacturing of the food, raw materials and ingredients that are commonly added in the art may be added. In addition, a formulation of the food is not limited, as long as the formulation is accepted as a food. The food composition of the present invention may be prepared as a variety of formulations, and since a food is used as raw materials, unlike general drugs, the food composition lacks side effects that may occur when a drug is taken for a long period, and may have excellent portability.

In accordance with another aspect of the present invention, there is provided a quasi-drug for prevention or alleviation of an inflammatory disease, the quasi-drug containing *Akkermansia muciniphila*-derived TARS or a fragment thereof as an active ingredient.

The terms used herein are as described above.

As used herein, the term "quasi-drug" refers to an article that is not an instrument, machine, or device, among the articles used for diagnosing, curing, relieving, treating, preventing, or alleviating diseases of humans or animals, and an article that is not an instrument, machine, or device, among the articles used for giving pharmaceutical influences on structures and functions of humans or animals, and also encompasses an externally-applied preparation for skin and a personal hygiene product.

When the *Akkermansia muciniphila*-derived TARS or fragment thereof of the present invention is added to a quasi-drug composition for prevention or alleviation of an inflammatory disease, the *Akkermansia muciniphila*-derived TARS or fragment thereof is added as it is or may be used together with other quasi-drug ingredients, or may be appropriately used according to a conventional method. The amount of the active ingredient mixed may be appropriately determined according to the purpose of use.

The externally-applied preparation for skin is not particularly limited, but may be preferably prepared and used in the form of an ointment, a lotion, a spray, a patch, a cream, a powder, a dispersion, a gelling agent, or a gel. Examples of the personal hygiene product may preferably include soaps, cosmetics, wet tissues, toilet paper rolls, shampoos, skin creams, facial creams, toothpastes, lipsticks, make-ups, foundations, blushers, mascaras, eye shadows, sunscreen lotions, haircare products, air-freshener gels, or facial cleansing gels, but are not limited thereto. In addition, other examples of the quasi-drug composition of the present invention may include disinfectants, shower foams, mouthwash products, wet tissues, detergents, handwashes, humidifier fillers, masks, ointments, or filters.

In accordance with another aspect of the present invention, there is provided a feed composition for prevention or alleviation of an inflammatory disease, the feed composition containing *Akkermansia muciniphila*-derived TARS or a fragment thereof as an active ingredient.

The terms used herein are as described above.

As used herein, the term "feed composition" may refer to any natural or artificial diet, single meal, or an ingredient of the single meal for animals to eat, ingest, and digest or suitable for this purpose, and the feed composition may be prepared in various forms known in the art.

The type of feed is not particularly limited, and any feed commonly used in the art may be used. Non-limiting examples of the feed may include: vegetable feeds, such as grains, nuts, food byproducts, algae, fibers, pharmaceutical byproducts, fats and oils, starches, barks, or grain byproducts; and animal feeds, such as proteins, inorganic substances, fats and oils, minerals, single-cell proteins, animal planktons, or foods. These may be used alone or in a mixture of two or more thereof. The animals have a concept encompassing livestock and pets.

The feed composition of the present invention may further contain binders, lubricating agents, preservatives, and the like added for prevention of quality deterioration thereof; and amino acids, vitamins, enzymes, probiotics, flavors, non-protein nitrogen compounds, silicates, buffers, colorings, extracts, oligosaccharides, and the like for efficiency improvement, as well as other feed mixtures and the like, but is not limited thereto.

MODE FOR CARRYING OUT THE INVENTION

Hereinafter, the present invention will be described in more detail through the following exemplary embodiments. However, the exemplary embodiments according to the present invention may be modified in many different forms, and the scope of the present invention shall not be construed as being limited to the exemplary embodiments described below. The exemplary embodiments of the present invention are provided to illustrate the present invention more completely to those skilled in the art.

Example 1: Secretory Proteins, Vesicle Isolation, and Proteome Analysis of *Akkermansia muciniphila*

*Akkermansia muciniphila* was inoculated in basal tryptone threonine medium (BTTM), and then cultured for one day with anaerobic conditions maintained. 1 L of bacterial culture was collected, sequentially centrifuged three times (500×g, 5000×g, and 15000×g, 30 min for each), and then filtered through a 0.22 μm filter to remove bacteria and thereby obtain only the supernatant. A QuixStand system with a 10 kDa cut-off filter was used to concentrate the supernatant, and the supernatant after concentration to 100 mL was again centrifuged at 15000×g for 30 min and filtered through a 0.22 μm filter. Finally, the supernatant was centrifuged at ultra-high speed (200000×g) for 2 h to obtain pellets including vesicles.

Figure 1:
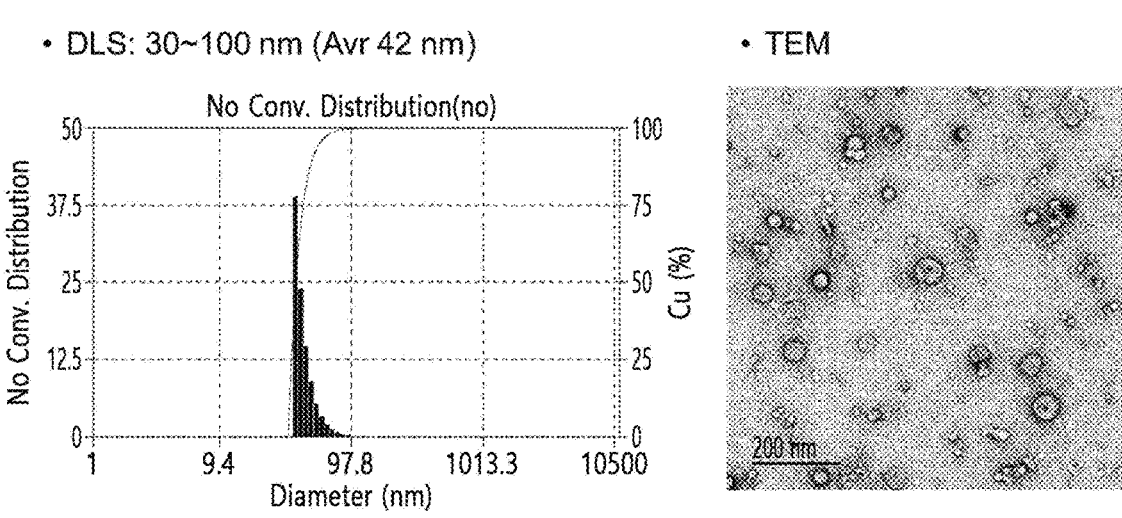
FIG. 1 shows the results of isolating *Akkermansia muciniphila*-derived vesicles.
Figure 3:
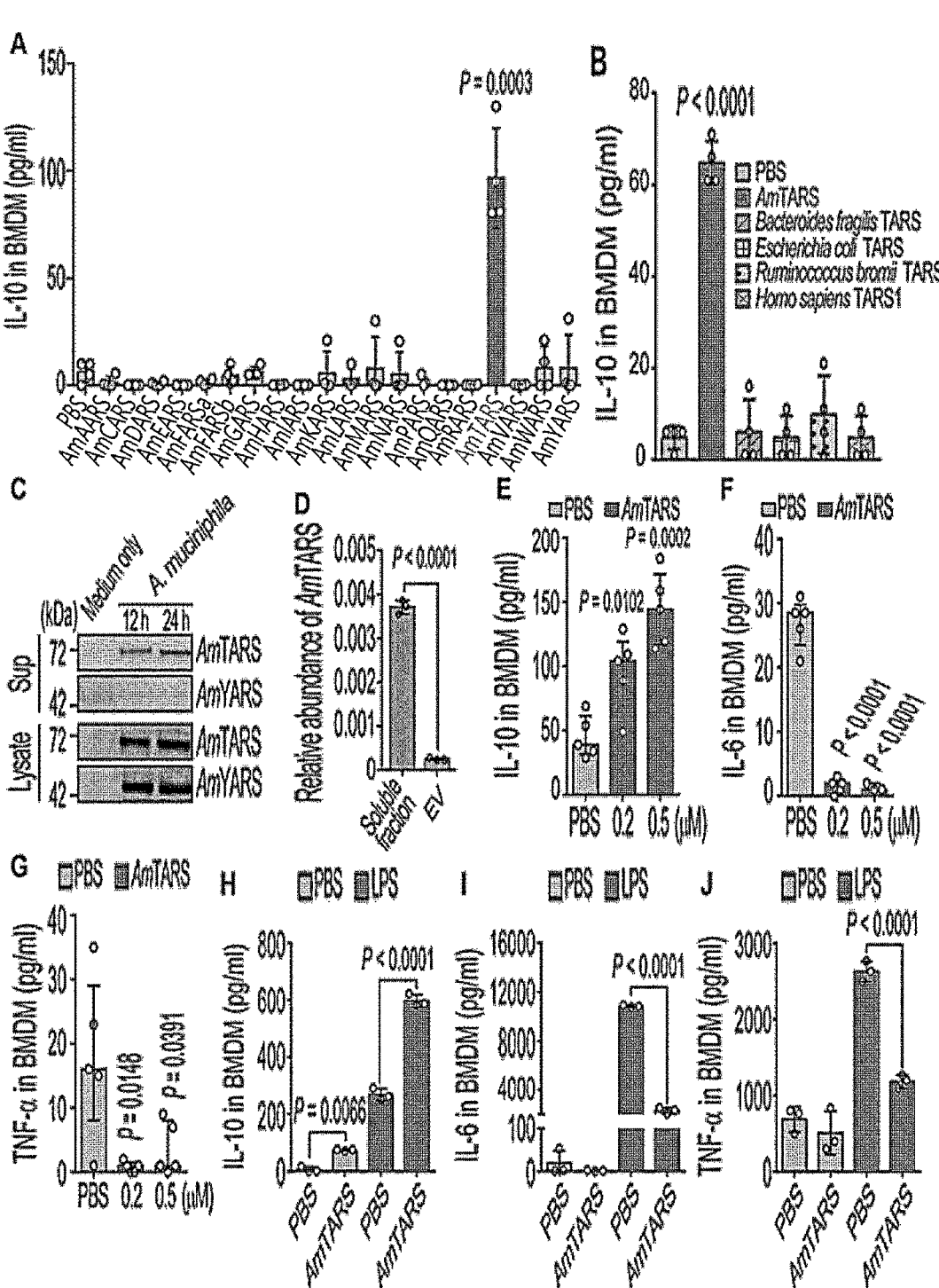
FIG. 3 shows that *A. muciniphila* extracellularly secretes AmTARS to exert anti-inflammatory immune regulation. (A and B) IL-10 in BMDM culture supernatants treated with 0.5 µM purified *A. muciniphila* aminoacyl-tRNA synthetases (AmARSs) (n=5 per group) (A) or 0.5 µM purified threonyltRNA synthetases (TARS) of indicated species (n=4 per group) (B). (C) Western blot analysis of AmTARS secreted into the culture supernatant of *A. muciniphila* under normal conditions. AmYARS was analyzed as a control. (D) Relative abundance of AmTARS in soluble fractions and in EVs purified from culture supernatants. (E-J) Levels of IL-10, IL-6, and TNF-α in BMDMs treated with 0.5 µM AmTARS under normal conditions (n=5 per group) (E-G) or with 0.5 µM AmTARS under LPS-induced inflammatory conditions (n=3 per group) (H-J). PBS, phosphate-buffered saline; AmAARS, alanyl-tRNA synthetase; AmCARS, cysteinyl-tRNA synthetase; AmDARS, aspartyl-tRNA synthetase; AmEARS, glutamyl-tRNA synthetase; AmFARSa, phenyl-alanyl-RNA synthetase alpha subunit; AmFARSb, phenyl-

As a result of investigating the size of the vesicles in the pellets by dynamic light scattering (DLS), the vesicles were particles with a size of 30-100 nm (average 42 nm) and had a spherical shape through transmission electron microscopy (TEM) analysis (FIG. 1).

Thereafter, the obtained pellets were lysed using a lysis buffer (containing 50 mM Tris-HCl (pH 7.5), 100 mM NaCl, 1% NP-40, 1 mM EDTA, 0.25% Na-deoxycholate, and a protease inhibitor cocktail). The lysate and supernatant were separately centrifuged at 13,000 rpm for 15 min, and then 20 μg for each was subjected to protein quantification, followed by sodium dodecyl sulfate-polyacrylamide gel electrophoresis (SDS-PAGE). The proteins separated on SDS-PAGE were transferred onto polyvinylidene difluoride (PVDF) membranes, and incubated with a solution of 1×TBST (137 mM NaCl, 50 mM Tris-HCl, 0.1% TWEEN 20 (Polysorbate 20)) and 4% BSA for 1 h and 30 min.

Rabbit polyclonal antibodies were prepared as antibodies against threonyl-tRNA synthetase (TARS), tyrosyl-tRNA synthetase (YARS), and prolyl-tRNA synthetase (PARS), which are *Akkermansia muciniphila*-derived aminoacyl-tRNA synthetases (AARSs), and glyceraldehyde 3-phosphate dehydrogenase (GAPDH). Two rabbits for each antigen were inoculated three times with high-purity AmTARS, AmYARS, AmPARS, and AmGAPDH as antigens. After the inoculation, individuals having antigen-specific antibodies in sera were selected through ELISA, and the secured sera were affinity-purified to obtain polyclonal antibodies.

Each antibody was diluted in 1×TBST and 4% BSA according to the concentration of use, and then incubated on the membrane at 4° C. overnight. Thereafter, the patterns of constituent proteins were analyzed through Coomassie brilliant blue (CBB) staining. Each sample was divided into three and analyzed by liquid chromatography-tandem mass spectrometry (LC-MS/MS) to thereby identify proteins including AARSs.

In the pellets containing vesicles, AmTARS (*Akkermansia muciniphila*-derived) was the most abundant among the *Akkermansia muciniphila*-derived AARSs, and AmYARS (*Akkermansia muciniphila*-derived YARS) and AmPARS (*Akkermansia muciniphila*-derived PARS) were present in relatively small amounts.

In this example, all His-tagged proteins were purified in vitro using *Escherichia coli* (*E. coli*). First, pET21a-AmTARS was introduced to cells through heat shock, and then cells containing genes were selected using the antibiotic ampicillin and cultured in liquid. The cultured cells were obtained using centrifugation, and then suspended using a solution of 50 mM Tris-HCl (pH 8.0), 300 mM NaCl, and 10 mM imidazole. The cells were lysed using sonication treatment, and then the supernatant was obtained by using high-speed centrifugation. The AmTARS-His protein was purified using Ni-NTA agarose affinity chromatography. The obtained protein was intensively dialyzed with a solution of 1×PBS (pH 7.4, 137 mM NaCl, 2.7 mM KCl, 10 mM $Na_2HPO_4$, and $2K_2HPO_4$), and then subjected to lipopolysaccharide (LPS) removal using TX-114 on the basis of the paper by Y Aida et al. (1990) to remove LPS from bacteria, thereby obtaining a high-purity protein. AmTARSΔ1, AmTARSΔ2, AmYARS, AmPARS, AmGAPDH, BfTARS, eTARS, RbTARS, and hTARS proteins were also obtained in the same manner.

As for Strep-tagged protein, HEK293T cells as mammalian cells were used, and 50-100 sheets of 150 mm culture dishes were cultured through several cell passages. For transduction of pEXPR-IBA105-AmTARS into the cells, polyethylenimine (PEI) was used. When the cells were cultured 24 h after the introduction, the cells were obtained using centrifugation. The cells were suspended in the solution of 100 mM Tris-HCl (pH 8.0), 150 mM NaCl, 5 mM EDTA, 1× protease inhibitor (GenDEPOT), and 1× phosphatase inhibitor (GenDEPOT), and then incubated at 4° C. for 30 min by using a rotator. A supernatant was obtained through high-speed centrifugation, and subjected to Strep-Tactin agarose affinity chromatography to purify Strep-AmTARS. The obtained protein was intensive-dialyzed using 1×PBS (pH 7.4) and then used for an experiment.

FLAG-tagged proteins were purified by affinity chromatography using FLAG M2 affinity gel.

The DNA constructs used in the present example are shown in Table 1 below.

TABLE 1

| | Name | SEQ ID NO | Expression vector | Tag | Expression system |
|---|---|---|---|---|---|
| 1 | AmTARS | 2 | pEXPR-IBA105 | 2 × Strep | Mammal |
| 2 | AmTARS | 2 | pET21a(+) | 6 × His | Bacteria |
| 3 | ΔU1AmTARS (AmTARSΔ1) | 7 | pET21a(+) | 6 × His | Bacteria |
| 4 | ΔU2AmTARS (AmTARSΔ2) | 8 | pET21a(+) | 6 × His | Bacteria |
| 5 | ΔU1ΔU2AmTARS (AmTARSΔ1Δ2) | 9 | pEXPR-IBA105 | 2 × Strep | Mammal |
| 6 | AmYARS | 10 | pET21a(+) | 6 × His | Bacteria |
| 7 | AmPARS | 11 | pET21a(+) | 6 × His | Bacteria |
| 8 | AmGAPDH | 12 | pET21a(+) | 6 × His | Bacteria |
| 9 | BfTARS | 13 | pET21a(+) | 6 × His | Bacteria |
| 10 | eTARS | 14 | pET21a(+) | 6 × His | Bacteria |
| 11 | RbTARS | 15 | pET21a(+) | 6 × His | Bacteria |
| 12 | hTARS | 16 | pET21a(+) | 6 × His | Bacteria |
| 13 | TLR2 | 17 | pIRES-FLAG | FLAG | Mammal |

Example 2: Analysis of Immune Cell-Secreted Cytokines According to AmTARS Treatment

*Akkermansia muciniphila* has been known to regulate immune cytokines in the gut environment, and thus to determine whether cytokines were also secreted from immune cells by AmTARS treatment, ELISA was performed using mammalian-derived immune cells.

Specifically, mouse bone marrow-derived macrophages (BMDMs) as mouse-derived immune cells were extracted from the mouse thighbone and shinbone, and then cultured in DMEM containing 10% fetal bovine serum (FBS) and antibiotics. Human macrophages (THP1) as human-derived immune cells were cultured in RPMI media containing 10% FBS and antibiotics.

The cultured cells were treated with AmTARS at 0.1 μM, 0.2 μM, and 0.5 μM for 24 h to obtain cell cultures. For cell removal, the media were centrifuged at 500×g for 10 min to obtain supernatants, which were then analyzed using an ELISA set (mouse interleukin (IL)-6, mouse IL-10, mouse tumor necrosis factor (TNF)-α, human IL-6, human IL-10, human TNF-α; BD Biosciences) to investigate the secretion of mouse- and human-derived immune cytokines.

Figure 2:
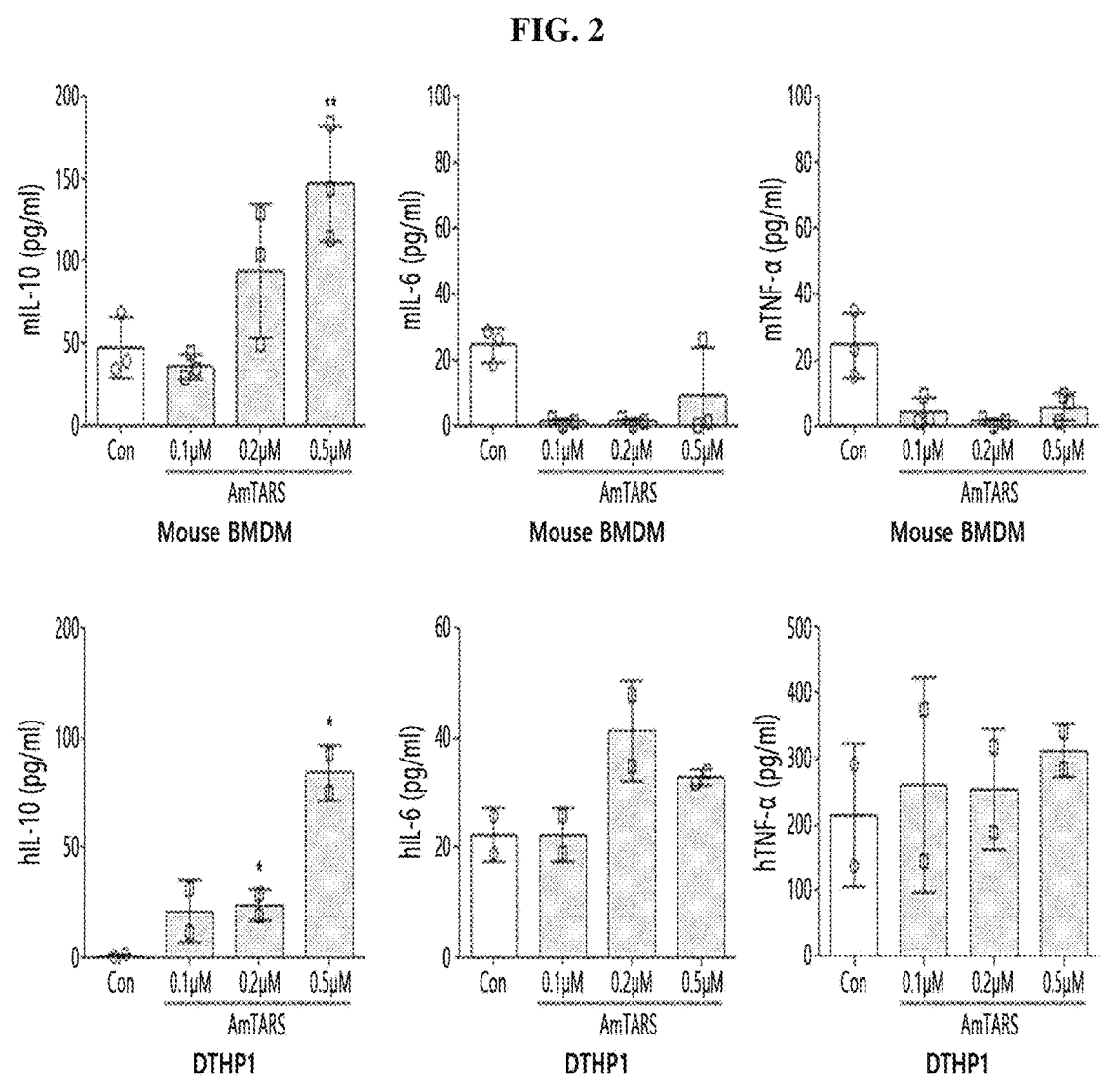

As a result, as shown in FIG. 2, when BMDMs were treated with AmTARS, the inflammatory cytokines IL-6 and TNF-α were not secreted while the secretion of the inflammatory cytokine IL-10 was increased in a dose-dependent manner based on AmTARS.

Similar to BMDMs, when THP1 were treated with AmTARS, IL-6 and TNF-α were not secreted while the secretion of IL-10 was increased in a dose-dependent manner based on AmTARS.

It was therefore confirmed that AmTARS induced the secretion of the inflammatory cytokine IL-10 from immune cells.

Next, To examine the involvement of commensal ARSs in immune regulation, we purified *A. muciniphila* ARSs (AmARSs) and tested their anti-inflammatory activity against bone marrow-derived macrophages (BMDMs). We found that AmTARS, but not other AmARSs, triggered a significant increase in production of anti-inflammatory IL-10 by BMDMs under steady state conditions (FIG. 3A). In addition, BMDMs treated with TARSs from other representative gut commensals, including *Bacteroides fragilis, Escherichia coli,* and *Ruminococcus bromii,* as well as from human, did not produce IL-10, suggesting a specific role for AmTARS in immune regulation (FIG. 3B). Next, we asked whether AmTARS is secreted extracellularly to play a role in immune regulation. An immunoassay using an AmARS-specific antibody revealed that *A. muciniphila* secretes AmTARS, but not tyrosyl-tRNA synthetase (AmYARS was used as a control), under normal steady-state conditions (FIG. 3C). Communication between Gram-negative bacteria is often mediated through secretion of soluble mediators and extracellular vesicles (EVs), and the same is true for *A. muciniphila*. Thus, we examined AmTARS detected predominantly in soluble fractions rather than in EVs purified from culture supernatants (FIG. 3D).

Of note, although AmTARS induced production of anti-inflammatory IL-10 by BMDMs under normal conditions, it had no effect on production of pro-inflammatory cytokines IL-6 and TNF-α (FIGS. 3E-3G).

Example 3: Regulation of Cytokine Secretion by AmTARS in Inflammatory Environment To determine whether AmTARS affects immune cytokine secretion when cellular inflammation was induced, mouse bone marrow-derived macrophages BMDMs as mouse-derived immune cells and human macrophages THP1 as human-derived immune cells were cultured by way of the same method as in Example 2.

Specifically, the cultured BMDMs and THP1 were treated with lipopolysaccharide (LPS) to induce an inflammatory response and were simultaneously treated with AmTARS at 0.1 μM, 0.2 μM, and 0.5 μM for 24 h to obtain cell cultures. The obtained cell cultures were analyzed for immune cytokine secretion by way of the same method as in Example 2.

As a result, AmTARS increased IL-10 levels, and suppressed IL-6 and TNF-α to an even greater extent following stimulation of BMDMs with lipopolysaccharide (LPS) (FIG. 3H-3J).

Also, as shown in FIG. 4, when the inflammation-induced BMDMs were treated with AmTARS, the secretion of the inflammatory cytokines IL-6 and TNF-α were reduced in a dose-dependent manner based on AmTARS while the secretion of the inflammatory cytokine IL-10 was increased in a dose-dependent manner based on AmTARS.

Similar results were observed in AmTARS-treated THP1 cells under both normal and inflammatory (LPS) conditions (FIG. 5).

In addition, as shown in FIG. 6, similar to BMDMs, when the inflammation-induced THP1 was treated with AmTARS, the secretion of IL-6 and TNF-α was reduced in a dose-dependent manner based on AmTARS while IL-10 was increased in a dose-dependent manner based on AmTARS.

Taken together, these results suggest that the commensal bacterium *A. muciniphila* secretes AmTARS to maintain (under normal conditions) and induce (under inflammatory conditions) host immune homeostasis.

Example 4: Regulation of Inflammatory Disease-Associated Intracellular Signaling by AmTARS To determine which signaling pathway was involved in the anti-inflammatory effect by the immune cytokine secretion regulation of AmTARS, an inflammatory environment was created through LPS treatment on mouse macrophage Raw264.7 as mouse-derived immune cells, and then changes in phosphorylation of signal transducers involved in the regulation of immune cytokine secretion according to the presence or absence of AmTARS treatment and the elapsed time (0.5 to 3 hours) were investigated. Raw264.7 cells were cultured in DMEM (Hyclone) containing 10% FBS and antibiotics.

As a result, as shown in FIG. 7, the signal transducers affected by AmTARS treatment were p38, c-Jun N-terminal kinase (JNK), and nuclear factor kappa-light-chain-enhancer of activated B cells (NF-kB), while extracellular signal-regulated kinase (ERK) was not affected by AmTARS treatment. JNK was affected through the regulation of phosphorylation from 30 min after AmTARS treatment, and p38 and NF-kB showed distinctive differences in phosphorylation from a control from 2 h after AmTARS treatment.

Next, to determine whether the anti-inflammatory function of AmTARS affected the regulation of metabolic disease-associated intracellular signaling, immunoblot analysis was performed using the mouse adipocyte 3T3-L1.

Specifically, 3T3-L1 cells were cultured in DMEM containing 10% bovine calf serum (BCS) and antibiotics under conditions of 5% $CO_2$ and 37° C. The cells were treated with 2 µM phorbol 12-myristate 13-acetate (PMA) or 20 ng/ml TNF-α to create an inflammatory environment in the cultured cells. The cells were treated with 100 nM insulin and 0.5 µM AmTARS for 24 h, and then changes in intracellular signaling were investigated.

As a result, as shown in FIG. 8, the treatment with insulin resulted in the phosphorylation of protein kinase B (AKT) compared with a control subjected to no treatment, and the treatment with insulin and PMA reduced the phosphorylation compared with the treatment with insulin alone. However, the treatment with AmTARS after insulin and PMA treatment again increased the phosphorylation.

In addition, as shown in FIG. 9, when insulin resistance was induced by TNF-α treatment, the phosphorylation of AKT was reduced in spite of the treatment with insulin, and the further treatment with AmTARS increased the phosphorylation. In the same experiment, glycogen synthase kinase (GSK)-3β, a downstream signal transducer of AKT, was phosphorylated and inhibited, and S6 kinase (S6K), affected by mammalian target of rapamycin (mTOR) complex 1 (mTORC1), was phosphorylated and activated. However, insulin receptor substrate (IRS), an upstream signal transducer of AKT in the insulin signaling, showed no significant change.

It was therefore confirmed that with the induction of cellular inflammation, the treatment with AmTARS inhibited inflammatory responses and increased the production of anti-inflammatory cytokines by regulating the phosphorylation of intracellular signal transducers, and affected the metabolic disease-associated intracellular signaling.

Example 5: Anti-Inflammatory Efficacy of AmTARS in Inflammatory Bowel Disease (IBD) Mouse Model Since the cell experiments confirmed that AmTARS had an anti-inflammatory function through immune cytokine regulation, an experiment was performed to verify the efficacy of AmTARS in an inflammatory bowel disease mouse model.

We evaluated the anti-inflammatory function of AmTARS in a mouse model of dextran sulfate sodium (DSS)-induced colitis. First, we assessed dose-dependent responses (i.e., changes in body weight and colon length) to intraperitoneal (i.p.) administration of AmTARS (0.05-0.4 mg/kg) once every other day for 10 days (FIG. 10A).

Overall, administration of AmTARS attenuated body weight loss and colon shortening in a dose-dependent manner (up to 0.2 mg/kg) (FIG. 11A). Administration of AmTARS at a dose of 0.4 mg/kg significantly attenuated body weight loss for up to 7 days, but yielded similar outcomes to those in colitis mice treated with phosphate-buffered saline (PBS) by Day 10, suggesting that high doses of AmTARS may have adverse effects (FIGS. 11A and 11B). Thus, we used a dose of 0.2 mg/kg for further in vivo evaluation of the anti-inflammatory immune effects of AmTARS. IP administration of AmTARS ameliorated disease activity scores, in addition to body weight loss and colon shortening, in colitis mice (FIGS. 10B, 11C, and 11D). Disruption of the epithelial lining and the damage score, particularly in the proximal colon, were significantly lower in AmTARS-treated colitis mice than in control mice (FIGS. 10C and 10D).

The disease activity score was calculated by adding up scores ranging from 0 to 4 points for each item of bloody stool, diarrhea, and weight loss, and the epithelial damage score was calculated by assigning 0 to 4 points according to the degree of colon tissue damage.

To identify the cells targeted by AmTARS, mice with injected i.p. with fluorescently labeled AmTARS, and fluorescence-positive cells in peritoneal exudate cells (PECs), were analyzed by flow cytometry. Fluorescently labeled Alexa568-AmTARS was detected predominantly on macrophages (F4/80+) rather than T cells (CD3+) and B cells (CD19+) (FIG. 10E). Next, we used a Mac-2 immunofluorescence antibody to test whether i.p.-injected AmTARS targets intestinal macrophages. Intense expression of Mac2 was detected in colonic epithelium, as well as in macrophages located in the lamina propria. Administered AmTARS (His) co-localized mainly with macrophages in the lamina propria, further demonstrating that AmTARS targets macrophages in the gut (FIG. 10F).

Since M2 macrophage polarization precedes production of anti-inflammatory cytokines such as IL-10, we assessed the effects of AmTARS on macrophage polarization. BMDMs were treated with PBS (negative control), LPS (to induce M1 polarization), or IL-4/IL-13 (to induce M2 polarization [positive control]) in the absence and presence of AmTARS, and the resulting M2 macrophage population was measured by flow cytometry using an antibody specific for the M2 macrophage surface marker CD206. Notably, AmTARS activated M2 polarization even in PBS-treated cells, and significantly re-polarized LPS-induced M1 macrophages to M2 macrophages (FIGS. 10G and 10H). M2 polarization was fully induced by IL-4/IL-13, in both the absence and presence of AmTARS (FIGS. 10G and 10H). Consequently, AmTARS significantly suppressed colitis-induced infiltration of inflammatory monocytes (CD11b+ F4/80−), restored IL-10-positive macrophage (CD11b+F4/ 80+IL-10+) numbers within colonic cells, and increased IL-10 levels in serum (FIG. 10I-10L).

To further validate the macrophage-dependent function of AmTARS in improving colitis, we investigated the anti-inflammatory effects of AmTARS in macrophage-depleted colitis mice.

A macrophage-deficient mice were prepared by administration of Clodrosome (administered at a concentration of 200 µL/animal to the abdominal cavity of mice a total of three times on Days 1, 5, and 8), and then the anti-inflammatory efficacy experiment was conducted by way of the same method as in Example 5. Normal mice injected with Encapsome were used as a control.

Consistent with the physiological data, AmTARS did not affect the numbers of inflammatory monocytes or IL-10-positive macrophages in macrophage-depleted mice (FIG. 12A-12C). Thus, AmTARS had no effect on colitis-induced body weight loss, shortening of the intestine, the damage score, the disease activity score, or disruption of the epithelial lining in macrophage-depleted mice (FIGS. 10M, 10N, and 12D-12F), further confirming the macrophage-specific functions of AmTARS. Collectively, these results indicate that AmTARS plays an anti-inflammatory cytokine-like role by activating IL-10-positive macrophage polarization.

Indeed, the therapeutic effects of AmTARS on colitis pathology were comparable with those of IL-10 in mice with colitis (FIG. 13).

Next, to measure IgA, mouse feces were collected and diluted in PBS containing a protein inhibitor, and then a supernatant with impurities removed was obtained, and 100 µL was placed in each well of a 96-well plate to perform protein coating at 4° C. for 2 h. The plate was washed three times with a washing solution (50 mM Tris, 0.2% in PBS) and then incubated with 100 µL of blocking solution at room temperature for 1-2 h, followed by washing. HRP conjugated IgA antibody (1:30000) was added and then incubated at room temperature for 1 h, followed by washing. Thereafter, 100 µL of a substrate solution was added, followed by incubation for 30 min, and then 50 µL of a stop solution was added, followed by measurement at 405-450 nm by an ELISA reader.

As a result, as shown in FIG. 14, the administration of AmTARS increased the secretion of the cytokine IL-10 in the mouse plasma and reduced the amount of IgA increased due to an inflammatory response.

To further validate the macrophage-dependent function of AmTARS in improving colitis, we investigated the anti-inflammatory effects of AmTARS in macrophage-depleted colitis mice. Consistent with the physiological data, AmTARS did not affect the numbers of inflammatory monocytes or IL-10-positive macrophages in macrophage-depleted mice (FIGS. 12A-12C). Thus, AmTARS had no effect on colitis-induced body weight loss, shortening of the intestine, the damage score, the disease activity score, or disruption of the epithelial lining in macrophage-depleted mice (FIGS. 10M, 10N, and 12D-12F), further confirming the macrophage-specific functions of AmTARS. Collectively, these results indicate that AmTARS plays an anti-inflammatory cytokine-like role by activating IL-10-positive macrophage polarization.

Example 6: B Cell-Mediated Anti-Inflammatory Efficacy of AmTARS in Inflammatory Bowel Disease Mouse Model To determine whether the inflammatory bowel disease alleviation effect induced through the secretion of IL-10 cytokine by AmTARS corresponded to a B cell-mediated effect, DSS was administered to B cell-deficient µMut mice (µ heavy chain mutation mice, B cell depletion mice) by way of the same method as in Example 5 to induce inflammatory bowel disease, and AmTARS was administered.

As a result, as shown in FIG. 15, the intestine length reduction and colon tissue damage due to inflammatory bowel disease were alleviated by AmTARS in the normal mice, but the alleviation effect by AmTARS was not observed in the B cell-deficient mice.

As shown in FIG. 16, in the B cell-deficient mice, the increase in B cells by AmTARS observed in the normal mice could not be shown, and the expression of IgA secreted by B cells was not observed.

It was therefore confirmed that AmTARS increased the distribution of B cells in the colon to induce an inflammatory bowel disease alleviation effect.

Example 7: Function Comparison Between TARS Derived from Main Microbes in Human Microbiome and Human-Derived TARS To determine whether TARS derived from other bacteria in the human microbiome and TARS secreted by human cells perform similar functions to AmTARS, TARSs derived from *Bacteroides fragilis, E. coli*, and *Ruminococcus bromii*, which are strains in the human microbiome, and TARS derived from *Homo sapiens* (BfTARS, eTARS, RbTARS, and hTARS, respectively) were purified and subjected to ELISA using immune cells.

Specifically, AmTARS bound to pET21a vector, BfTARS bound to pET21a vector, eTARS bound to pET21a vector, RbTARS bound to pET21a vector, and hTARS bound to pET21a vector were separately introduced into *E. coli* through heat shock, and then cells containing genes were selected using the antibiotic ampicillin and cultured in liquid. The cells were obtained by centrifuging the cultures, and then suspended using a solution of 50 mM Tris-HCl (pH 8.0), 300 mM NaCl, and 10 mM imidazole. The cells were lysed using sonication treatment, and then centrifuged at high speed to obtain supernatants. The supernatants were passed through Ni-NTA agarose affinity chromatography to purify AmTARS-His, BfTARS-His, eTARS-His, RbTARS-His, and hTARS-His proteins. The obtained proteins were intensively dialyzed with a solution of 1×PBS (pH 7.4, 137 mM NaCl, 2.7 mM KCl, 10 mM $Na_2HPO_4$, $2K_2HPO_4$), and lipopolysaccharide (LPS) of *E. coli* was removed using TX-114 to obtain high-purity proteins (Left in FIG. 17).

Thereafter, BMDMs were treated with each TARS (AmTARS, BfTARS, eTARS, and RbTARS) by way of the same method as in Example 2 and subjected to ELISA to investigate the secretion of IL-10.

As a result, as shown in FIG. 17, the secretion of the anti-inflammatory cytokine IL-10 was specific to AmTARS.

Next, BMDMs were treated with LPS to create an inflammatory environment by way of the same method as in Example 3, and then treated with each TARS (AmTARS, BfTARS, eTARS, and hTARS) to investigate the secretion of IL-10.

As a result, as shown in FIG. 17, IL-10 was increased in a protein concentration-dependent manner in the AmTARS treatment group, but the secretion of IL-10 was not significantly increased in TARSs of other species (BfTARS, eTARS, and hTARS) compared with the LPS treatment control.

It was therefore confirmed that as a result of comparing functions in the immune responses of TARSs derived from strains in the microbiome, the anti-inflammatory response through an increase in IL-10 secretion was shown only in the case of AmTARS treatment.

Example 8: Analysis of AmTARS Functional Sites

To uncover the molecular mechanism underlying the anti-inflammatory immune function of AmTARS, we compared its amino acid sequence with that of human TARS1, and with those of TARSs from bacterial species representative of the gut microbiota. AmTARS contains two additional unique regions within its N-terminal (SEQ ID NO: 3, residues 99-113 of SEQ ID NO: 1 (A region encoded by the nucleotide sequence of SEQ ID NO: 5, which is the sequence corresponding to the 295th to 339th nucleotides of SEQ ID NO: 2), hereafter referred to as U1) and catalytic (SEQ ID NO: 4, residues 290-312 of SEQ ID NO: 1 (A region encoded by the nucleotide sequence of SEQ ID NO: 6, which is the sequence corresponding to the 868th to 936th nucleotides of SEQ ID NO: 2), hereafter referred to as U2) domains, which are not found in other TARSs (FIG. 18A). In addition, Blast-based sequence searches (blast.ncbi.nlm-.nih.gov/Blast.cgi) detected no sequences with significant homology to the unique regions, suggesting that these unique regions may have been evolutionarily assimilated by A. muciniphila specifically for immune regulation.

Next, we modeled the structure of AmTARS using AlphaFold (Jumper et al., 2021), and found that it showed significant structural similarity to other TARSs, including Staphylococcus aureus TARS (PDB ID 1NYQ) and human TARS1 (PDB ID 4HWT) (FIG. 18B). This suggests that both U1 and U2 within AmTARS are surface-exposed, and may be involved in interactions with immune-related host targets (FIG. 19A). Subsequently, we evaluated the functionality of U1 and U2 by generating mutant proteins (ΔU1 and ΔU2) harboring deletions in these unique regions. ΔU1 and ΔU2 mutants were constructed according to Table 1 and named ΔU1AmTARS (AmTARSΔ1) and ΔU2AmTARS (AmTARSΔ2), respectively.

To purify ΔU1AmTARS and ΔU2AmTARS, ΔU1AmTARS bound to pET21a vector and ΔU2AmTARS bound to pET21a vector were separately introduced into E. coli through heat shock, and then cells containing genes were selected using the antibiotic ampicillin and cultured in liquid. The cells were obtained by centrifuging the cultures, and then suspended using a solution of 50 mM Tris-HCl (pH 8.0), 300 mM NaCl, and 10 mM imidazole. The cells were lysed using sonication treatment, and then centrifuged at high speed to obtain supernatants. The supernatants were passed through Ni-NTA agarose affinity chromatography to purity ΔU1AmTARS-His and ΔU2AmTARS-His proteins. The obtained proteins were intensively dialyzed with a solution of 1×PBS (pH 7.4, 137 mM NaCl, 2.7 mM KCl, 10 mM Na₂HPO₄, 2K₂HPO₄), and then LPS from E. coli was removed using TX-114 to obtain high-purity proteins (FIG. 20).

TARS is an aminoacylase involved in protein synthesis, and the domain and site involved in its function are well known. The constructed deletion mutants were confirmed to have deletions of parts irrelevant to the function, but the aminoacylation reaction experiment was conducted to determine whether the deletion mutants performed the intrinsic functions thereof appropriately.

Specifically, a 2× reaction solution (100 mM Tris-HCl (pH 7.5), 20 mM MgCl₂, 200 mM NaCl, 200 mM KCl, 2 mM DTT, 500 μM ATP, and 5 mM L-threonine) was prepared, and 25 μL of a reaction solution, 20 μL of distilled water, and 5 μL of protein were added to make a final 50 μL volume, followed by incubation for 30 min. Thereafter, a reaction was conducted using a malachite green phosphate assay kit (Bioassay Systems) for 30 min, and the free monophosphate group (P$_i$) was measured at a wavelength of 620 nm.

As a result, as shown in FIG. 20, there was no reaction for AmYARS used as a control for threonine amino acid-specific reaction, but an aminoacylation reaction was shown for all of AmTARS, ΔU1AmTARS, and ΔU2AmTARS. It was therefore confirmed that the deletion sites had no effect on the intrinsic function of the proteins.

Next, BMDMs were treated with AmTARS, ΔU1AmTARS, and ΔU2AmTARS separately and analyzed by ELISA by way of the same method as in Example 2. As a result, Neither mutant protein was different from the wild-type (WT) AmTARS with respect to its enzymatic activity (FIG. 19B), but both abolished the IL-10 production in BMDMs (FIG. 19C).

Next, to determine whether the regulation of immune cytokine secretion by AmTARS in an inflammatory environment was induced by the two functional sites, the mouse-derived immune cell Raw 264.7 cells were treated with LPS to induce an immune response by the method as in Example 3, and treated with AmTARS, ΔU1AmTARS, and ΔU2AmTARS for 24 h separately to obtain cell cultures. The obtained cell cultures were analyzed for Immune cytokine secretion by way of the same method as in Example 2.

As a result, as shown in FIG. 21, the secretion of the inflammatory cytokines IL-6 and TNF-α was reduced in a protein concentration-dependent manner through AmTARS treatment, and IL-10 was increasingly secreted in an AmTARS concentration-dependent manner, but the treatment with ΔU1AmTARS and ΔU2AmTARS had no effect on the secretion of IL-6, TNF-α, and IL-10.

To determine whether U1 and U2 as deletion sites exhibited an anti-inflammatory effect of AmTARS, peptides were prepared using respective sequences, and the effect thereof was investigated.

A total of four types of fragments (AmTARS, U1 (R1, SEQ ID NO: 3), U2 (R2, SEQ ID NO: 4), Tat-function site 1 (Tat-R1), and Tat-function site 2 (Tat-R2)) were synthesized including U1, U2, and fragments obtained by adding, to the functional sites, Tat tag, which is a tag for favorable delivery into cells.

An inflammatory environment was created through LPS in BMDMs by way of the same method as in Example 3, and then the cells were treated with the four types of fragments, and the immune cytokine secretion was determined by ELISA.

As a result, as shown in FIG. 22, the secretion of IL-6 was reduced, and the secretion of IL-10 was increased by AmTARS, R2, and Tat-R2 in the created inflammatory environment.

When the concentrations of U2 were 100 μM, 200 μM, 300 μM in the same conditions, the secretion of IL-6 was reduced and the secretion of IL-10 was increased by all of U2 (R2) 100 μM and 300 μM and Tat-R2 100 μM, 200 μM, and 300 μM. Of these, the secretion of IL-10 was increased by 2-fold in the Tat-R2 treatment groups compared with AmTARS.

It was therefore confirmed that the AmTARS-specific regulation of immune cytokine secretion was exerted from U1 and U2.

Example 9: Efficacy of AmTARS Functional Sites in Inflammatory Bowel Disease Mouse Model To verify the anti-inflammatory efficacy of specific functional sites of AmTARS, AmTARS, ΔU1AmTARS, and ΔU2AmTARS were separately administered to the inflammatory bowel disease mouse model of Example 5, and then an anti-inflammatory efficacy experiment was performed.

Neither mutant protein promoted recovery of body weight loss, disease activity scores, shortening of the intestine, or epithelial lining disruption and damage scores, in colitis-induced mice (FIGS. 19D-19F, 23A, and 23B). The positive immune regulatory functions of AmTARS that reduced colitis-induced pro-inflammatory monocytes and enhanced IL-10-positive macrophages in the colon were eliminated when mutant AmTARSs were administered to colitis mice (FIGS. 19G and 23C). Thus, these data clearly demonstrate that the unique regions U1 and U2 within AmTARS are essential for its anti-inflammatory function.

In addition, as shown in FIG. 24, ΔU1AmTARS and ΔU2AmTARS, unlike AmTARS, reduced the efficacy of increasing B cells in the colon, and did not show an effect of reducing the amount of IgG increased by an inflammatory bowel disease. It was therefore confirmed that U1 and U2 were essential for anti-inflammatory efficacy in AmTARS.

Example 10: Human Interactome of AmTARS

To identify the host target of AmTARS, we performed membrane protein interactome analysis using THP1 cells. Several potential interactors, which are receptors involved in innate immunity, were identified, and their interactions with AmTARS were evaluated using a pull-down assay.

Specifically, THP1 was separated into cytoplasmic and cell membrane components by using Mem-PER™ Plus Membrane Protein Extraction Kit. The separated lysate was incubated with His-tagged AmTARS and then pulled down with His-tagged resin. Proteins bound to the resin were eluted and then loaded on SDS-PAGE gel to identify proteins by CBB staining.

As a result, as shown in FIG. 25, many proteins including AmTARS were precipitated.

Then, each gel was largely divided into five, which were then subjected to liquid chromatograph-tandem mass spectrometer (LC-MS/MS) analysis. A part of the gel to be analyzed was placed in a 1.5 ml tube. The gel was de-stained with 25 mM ammonium bicarbonate (ABC)/50% acetonitrile (ACN) until the gel was transparent. Thereafter, 10 mM DL-dithiothreitol (DTT) and 55 mM iodoacetamide (IAA) were added, followed by reduction and alkylation. Upon the end of the reaction, the gel was dried, and then 0.0125 μg/μL trypsin was added with the same volume as the gel, followed by incubation overnight. Thereafter, the sample was collected and then dried with a vacuum pump.

The sample was dissolved in 10 μL of 2% ACN/0.1% formic acid (FA) solution, and 5 μL thereof was injected. The LTQ-Orbitrap Elite and Easy nano-LC 1000 by Thermo were used for analysis, and solution A used for LC was 0.1% FA/water, and solution B was 0.1% FA/ACN, and solution B was allowed to flow at a gradient of 2% to 32% for 120 min, and the flow rate was 0.3 L/min. The trap column used was pepamap 100 (75 μm×2 cm, C18, 3 μm, 100 Å), and the analytical column was pepmap RSLC (C18 2 μm, 100 Å, 75

μm×15 cm). The analytical column temperature was 50° C., and the full MS resolution was 60,000, and AGC target was 1E5. MS/MS used the HCD method with a resolution of 15,000, and MS/MS was set to top 15, IT 100 ms, and threshold 200,000.

The raw data obtained by LC-MS/MS were analyzed using Maxquant. For the database, uniprot_Homo sapiens was used, and modification was set as fixed modification—carbamidomethyl (c), variable modification—oxidation (M), acetyl (protein N-term). Peptide 2 or more were assigned, and LFQ and match between run were applied to perform analyses. "LFQ intensities" were compared by filtration through at least 2 razor+unique peptide.

As a result, as shown in FIG. 26, a total of 1178 proteins were identified in the pull-down sample using the cellular membrane fraction, and 805 proteins were identified in the cell lysate fraction. Several potential interactors, which are receptors involved in innate immunity, were identified (FIG. 27A). Of these, Toll-like receptor 2 (TLR2) was selected as an interactome candidate involved in the immune response on the basis of higher intensity and higher score compared with a control that did not react with AmTARS. Thereafter, an interaction experiment was performed on the candidate as a target.

Then, Strep-tagged AmTARS, AmTARS having deletions of two functional site (AmTARSΔ1Δ2), and FLAG-tagged TLR2 were transduced into human-derived HEK 293T cells through PEI, and thereafter, the cells were lysed using a lysis buffer containing 50 mM Tris-HCl (pH 7.5), 100 mM NaCl, 1% NP-40, 1 mM EDTA, 0.25% Na-deoxycholate, and a protease inhibitor cocktail. The cell lysates each were incubated with Strep Tactin beads and washed with a buffer containing 137 mM NaCl, 2.7 mM KCl, 10 mM Na$_2$HPO$_4$, 1.8 mM KH$_2$PO$_4$, and 1 mM EDTA, and proteins attached to the beads were eluted and analyzed by immunoblotting.

In addition, His-tagged AmTARS and FLAG-tagged protein were mixed at a ratio of 1:2, incubated with Ni-NTA beads, and then washed with a buffer containing 50 mM Tris-HCl (pH 8.0), 300 mM NaCl, 30 mM imidazole, and 1% NP-40, and the proteins attached to the beads were eluted and identified on SDS-PAGE gel.

The results suggested that among the candidates tested, AmTARS interacted only with TLR2 (FIGS. 28A, 27B, and 27C); thus, TLR2 may be the receptor targeted by AmTARS to trigger IL-10-mediated anti-inflammatory immune regulation. By contrast, the pull-down assay clearly showed no interaction between AmTARS and TLR4 (FIG. 27D). To further validate the interaction between AmTARS and TLR2, in vitro pull-down assays were performed using purified TLR2 and AmTARS proteins (FIG. 28B). The results clearly showed that AmTARS interacts directly with TLR2 via the U2-containing catalytic domain (CD). The interaction between the U2-deleted CD (ΔU2CD) protein and TLR2 was markedly weaker. There was no direct interaction between the U1-containing N-terminal domain (NTD) and TLR2, suggesting that U1 might be involved indirectly in the interaction between AmTARS and TLR2.

The TLR2-dependent immune function of AmTARS was further corroborated using TLR2 knock-out (KO) mice. AmTARS did not induce IL-10 production in BMDMs from TLR2-KO mouse, demonstrating that interaction between AmTARS and TLR2 is indispensable for anti-inflammatory immune activation (FIG. 28C). We furthermore confirmed that a unique region was required by engineering E. coli TARS (EcTARS), which had no anti-inflammatory immune function in BMDMs (FIG. 3B). Incorporation of the AmTARS U1 and U2 sequences into the corresponding regions in EcTARS [EcTARS (U1/U2), SEQ ID NO: 18] conferred the ability to trigger IL-10 production on EcTARS (FIG. 28D). However, IL-10 production by EcTARS (U1/U2) was abolished in BMDMs from TLR2-KO mice, providing further evidence that AmTARS regulates host immune cells via its unique regions in a TLR2-dependent manner (FIG. 28D).

Example 11: TLR2-Mediated Anti-Inflammatory Efficacy of AmTARS in Inflammatory Bowel Disease Mouse Model We assessed the role of TLR2 in AmTARS function in vivo. To verify whether the binding between AmTARS and TLR2 actually acted on the anti-inflammatory effect of AmTARS, an inflammatory bowel disease mouse model was prepared from TLR2-deficient mice by way of the same method as in Example 5 and investigated for anti-inflammatory efficacy after the administration of AmTARS. TLR2-KO mice were slightly more susceptible to DSS-induced colitis than WT mice, as reported previously (Rakoff-Nahoum et al., 2004).

Colitis-induced body weight loss and the disease activity score in TLR2-KO mice did not improve after AmTARS treatment (FIGS. 28E and 29A). The same was true for shortening of intestine length, disruption of the epithelial lining, and the damage score (FIGS. 28F, 28G, and 29B). Consistent with these results, AmTARS did not induce either a reduction in pro-inflammatory monocyte numbers or an increase in IL-10-secreting macrophage numbers in colitis TLR2-KO mice (FIGS. 28H and 28I). Furthermore, AmTARS did not cause M2 macrophage polarization of peritoneal macrophages from TLR2-KO mice under non-inflammatory conditions (FIG. 28J). Likewise, no M2 macrophages were observed in PECs isolated from TLR2-KO mice (FIG. 28K).

As shown in FIG. 30, in the TLR2-deficient mice, AmTARS did not show efficacy of increasing B cells in the colon, and a significant change in the amount of IgA could not be observed.

These results strongly suggest that AmTARS is a commensal-derived TLR2 ligand required to maintain host immune homeostasis.

Example 12: AmTARS/TLR2 Efficiently Induces Anti-Inflammatory Responses by Activating CREB To identify the signaling pathway triggered by AmTARS, we first evaluated kinases and CREB. IL-10 production and M2 polarization were measured in BMDMs treated with inhibitors of ERK (PD98059), p38 (SB203580), MSK1/2 (SB747651A), CREB (666-15), PI3K (Wortmannin) and AKT (AKT1/2) before subsequent stimulation with AmTARS. Inhibition of each of these molecules resulted in significant suppression of IL-10 production (FIG. 31A) and macrophage polarization (CD206 positive) by AmTARS (FIG. 31B), suggesting that AmTARS triggers the MAPK and PI3K/AKT signaling pathways to induce anti-inflammatory responses.

Subsequently, we conducted immunoblotting assays to measure the time-dependent activation of AmTARS/TLR2-induced signaling molecules in both BMDMs and THP1 cells. AmTARS rapidly activated ERK, p38, and MSK1/2 within 15 min and, subsequently, phosphorylation of CREB at Ser133 (which is essential for IL-10 production) within 30 min in BMDMs (FIG. 31C) and THP1 cells (FIG. 31D). We then compared AmTARS-triggered TLR2 signaling with typical ligand-triggered signaling using Pam3CSK4 (the synthetic canonical TLR2/1 agonist, referred to hereafter as Pam3) in BMDMs stimulated for 30 min. Overall, the TLR2-dependent activation pattern of the signaling molecules in the AmTARS-triggered pathway was similar to that of molecules triggered by Pam3, which was completely blocked by an TLR2 antibody (FIG. 31E). However, significantly greater activation of CREB was observed in AmTARS-treated BMDMs than in Pam3-treated BMDMs (FIG. 31E). By contrast, activation of NF-κB was greater in Pam3-treated BMDMs than in AmTARS-treated BMDMs (FIG. 31E).

CREB phosphorylated at Ser133 inhibits NF-κB activation by competing for limited amounts of their shared coactivator, CREB-binding protein (CBP)/p300, thereby suppressing pro-inflammatory responses. Our results show that AmTARS induces production of IL-10, and even inhibits production of pro-inflammatory cytokines IL-6 and TNF-α, in macrophages under inflammatory conditions (FIGS. 3H-3J and 5D-5F). These data indicate that, distinct from typical TLR2 ligands, AmTARS is a gut commensal-derived TLR2 ligand that maintains immune homeostasis by limiting inflammatory signaling.

AmTARS activated PI3K and AKT, and subsequently inhibited GSK3β activity via AKT-mediated phosphorylation at Ser9, in BMDMs (FIG. 31F) and THP1 cells (FIG. 31G) within 15 min. TLR-stimulated inhibition of GSK3β also enhances association of coactivator CBP with CREB, rather than NF-κB, thereby increasing IL-10 production and suppressing release of pro-inflammatory cytokines. Thus, these data demonstrate that the interaction between AmTARS and TLR2 efficiently activates CREB by triggering the MAPK and PI3K/AKT signaling pathways.

Since TLR2 forms heterodimers with either TLR1 or TLR6 during activation, we assessed which form is targeted by AmTARS. An immunoassay showed that AmTARS-induced TLR2 signaling is shut down by antibodies targeting TLR1, TLR6, and TLR2, indicating that AmTARS targets both the TLR2/1 and TLR2/6 forms to activate anti-inflammatory signaling (FIG. 31H).

We next performed global gene expression profiling of BMDMs treated with AmTARS or Pam3 for 1 or 3 h (FIG. 32A). Principle components analysis (PCA) revealed a similar gene expression pattern for AmTARS and Pam3 at 1 h, but clearly different profiles at 3 h (FIG. 32B). The number of genes whose expression was affected by AmTARS, and the extent of their (up- or down-) regulation, was dissimilar to those affected by Pam3, further indicating that AmTARS acts as an immune regulator distinct from typical TLR2 ligands (FIG. 33A). Subsets of genes showing different expression patterns between AmTARS and Pam3 were classified into six clusters by hierarchical clustering analysis (FIGS. 33A and 33B). The gene expression pattern at 3 h was particularly different for clusters 3 and 4 (FIGS. 32C, 33A, and 33B). In general, genes belonging to clusters 3 and 4 are associated with inflammation and anti-inflammation, respectively (FIG. 32C). Gene set enrichment analysis revealed significant induction of inflammatory response-related genes in Pam3-treated BMDMs compared with AmTARS (FIG. 32D). Notably, treatment of BMDMs with Pam3 was significantly associated with up-regulation of inflammation-related transcription factors such as NF-κB, RELA, and TFAP2A, whereas AmTARS treatment was associated with up-regulation of the anti-inflammation-related transcription factor CREB (FIG. 32E).

Next, we validated the anti-inflammatory function of AmTARS using the Tg (NFκB:EGFP) zebrafish transgenic line, which allows monitoring of NF-κB activity in vivo. Consistent with the gene set enrichment analysis patterns (FIGS. 32D and 32E) and the signaling pathway results (FIG. 31C-31G), the increased NF-κB activity in the distal intestine of zebrafish larvae induced by repeated DSS treatment (FIG. 32F) was significantly dampened by AmTARS (FIGS. 32G and 32H), indicating the suppressive function of AmTARS on pro-inflammatory responses in vivo.

Taken together, these data provide further evidence that AmTARS secreted by the commensal bacterium *A. mucin-iphila* is a steady-state immune homeostatic mediator that is distinct from typical TLR2 ligands, and which maintains and induces immune homeostasis in response to inflammatory challenges (FIG. 32I).

Example 13: Verification of Anti-Inflammatory Efficacy of AmTARS in Inflammatory Bowel Disease (IBD) Mouse Model To verify whether the administration of AmTARS via an intramuscular injection exhibits an anti-inflammatory efficacy, an inflammatory bowel disease mouse model was prepared in accordance with Example 5. Further, AmTARS was intramuscularly injected into the mouse model to confirm the anti-inflammatory efficacy thereof.

As a result, AmTARS, when intramuscularly injected at 0.4 mg/kg or more, was confirmed to have the efficacy of decreasing the weight and intestinal length of the mouse model caused by the inflammatory bowel disease. Further, AmTARS was confirmed to alleviate the damage to intestinal epithelial cells caused by the same (FIG. 34).

The results of the above examples confirmed that *Akkermansia muciniphila* TARS or a fragment thereof according to the present invention increased the secretion of the anti-inflammatory cytokine IL-10 by promoting the differentiation of M2 macrophages as anti-inflammatory macrophages to attain the proliferation of macrophages, and thus led to the proliferation of B cells to exhibit an anti-inflammatory effect, thereby exhibiting an effect of alleviating not only an inflammatory disease but also an immune disease, an infectious disease, and a metabolic disease, which were accompanied by inflammation, and in particular, had an excellent effect on the prevention or treatment of inflammatory bowel disease or the like.

As set forth above, a person skilled in the art to which the present invention pertains will be able to understand that the present invention may be embodied in other specific forms without departing from the technical spirit or essential characteristics thereof. Therefore, the embodiments described above should be construed as being exemplified and not limiting the present invention. The scope of the present invention is not defined by the detailed description as set forth above but by the accompanying claims of the invention, and it should also be understood that all changes or modifications derived from the definitions and scopes of the claims and their equivalents fall within the scope of the invention.

The invention claimed is:

1. A method for treating an inflammatory bowel disease in a subject in need thereof, the method comprising administering to the subject a pharmaceutical composition comprising a purified *Akkermansia muciniphila*-derived threonyl-tRNA synthetase (TARS) or a purified fragment thereof as an active ingredient, wherein the TARS comprises an amino acid sequence of SEQ ID NO:1, and the purified fragment comprises an amino acid sequence selected from a group consisting of SEQ ID NO:3 and SEQ ID NO:4.

2. The method of claim 1, wherein the purified TARS or the purified fragment exhibits at least one effect selected from the group consisting of:

(i) increasing IL-10 secretion;

(ii) reducing IL-6 or TNF-α secretion;

(iii) increasing B cells;

(iv) increasing macrophages; and (v) promoting the differentiation of macrophages into M2 macrophages.

3. The method of claim 1, wherein the inflammatory bowel disease is at least one selected from the group consisting of colitis, ulcerative colitis, Crohn's disease, and Behçet's enteritis.

4. The method of claim 1, wherein the pharmaceutical composition is a pharmaceutical composition or a quasi-drug composition.

5. A method for differentiation or proliferation of B cells, the method comprising administering to a subject the pharmaceutical composition of claim 1.

6. A method for differentiation or proliferation of M2 macrophages, the method comprising administering to a subject the pharmaceutical composition of claim 1.

* * * * *

SEQUENCE LISTING

```
Sequence total quantity: 18
SEQ ID NO: 1              moltype = AA  length = 630
FEATURE                   Location/Qualifiers
REGION                    1..630
                          note = Akkermansia muciniphila TARS
source                    1..630
                          mol_type = protein
                          organism = unidentified
SEQUENCE: 1
MSEHKERKTL EERQQMSDLE RLRHSCAHVL ATAICRLWPD AQLAGGPAVD NGFYYDVELD  60
HRISTEDFER IEEEMKKVVK ENQVFQKEVI SRADAMKMAE SGELGALGPR SEPSRFKIDL  120
LNDIPEDEEI SLYRNGDFTD LCAGPHVGRT GNCKAFKIMS VASAFYKGDK NRPMLQRIYG  180
TCFPNRTQLD EHLERLEEAR RRDHRKLGRE LGLFCIDESV GQGLILWKPK GALIRRSLQD  240
FITEELDKLG YSQVYTPNIG KLDLYRTSGH FPYYQESQYA PIPERDAMEK LSQEGASCAE  300
LFNGLATGTI EGYMLKPMNC PHHIKIYAND AHSYRDLPVR LAEFGTVYRW EQSGELGGMT  360
RVRGFTQDDA HIFCTPDQLA GEIRQCLGIV KTIFGTLGMT DYRVRLSMRD PESDKYVGSP  420
ENWDKAEQAL REAAEWLGAD YSEEAGEAAF YGPKIDFIVR DAIGREWQLG TVQVDYNLPE  480
RFDLHYTGAD NKPHRPVMVH RAPFGSMERF TGLLIEHFEG KFPTWLSPEQ VRVLPISDKV  540
TDVAAAHRTA LAARGVRVTV DETPDKIGAK IRNARLDRVP YMLVLGQREA EDGTVSVRHR  600
DKGDLGAMPF EQFADLVARE IAERHISPVI                                   630

SEQ ID NO: 2              moltype = DNA  length = 1893
FEATURE                   Location/Qualifiers
misc_feature              1..1893
                          note = Akkermansia muciniphila TARS
source                    1..1893
                          mol_type = other DNA
                          organism = unidentified
SEQUENCE: 2
atgtccgaac acaaggaaag aaagactctt gaagaacgcc aacagatgtc tgatctggaa  60
cggctgcgcc actcctgcgc gcacgttctg gctacggcca tttgccgcct ctggccggat  120
gcccagctgg ccggcgggcc tgccgtggat aacggttttt attacgacgt ggagctggac  180
caccgcatca gcacagagga tttttgaacgc attgaggagg agatgaaaaa agtggtgaag  240
gaaaaccagg ttttccagaa ggaagtcatt tcccgcgcgg atgccatgaa gatggcggaa  300
tccggggagc tgggcgccct gggcccccgc agcgagcctt cccgcttcaa gattgacctg  360
ctgaacgaca tcccggaaga cgaggagatt tccctctacc gcaacgggga ttttacggac  420
ttgtgcgccg gtcccacgt gggccgcacg ggcaactgca aggcattcaa aatcatgagc  480
gtggcgagcg ccttctacaa gggggacaaa aaccgcccca tgctccagcg catttacggc  540
acctgcttcc cgaaccgcac ccagcttgac gaacacctgg aacggctgga agaggcgcgg  600
cgccgcgacc accgcaaact gggccgcgaa ctgggcctgt tctgcattga cgaatccgtg  660
gggcaggggc tcatcctctg gaagcccaag ggggctctca tccgccgttc cctgcaggac  720
```

```
ttcatcacgg aagagctgga caagctgggc tactcccagg tgtacacgcc caacatcggc   780
aagctggacc tgtaccgcac gtccggacac ttcccgtatt atcaggaaag ccagtacgcg   840
cccatcccag aacgggacgc catggaaaaa ctcagccagg aggggggcttc ctgcgcggaa   900
ctgttcaacg gcctggccac cggcaccatt gagggctata tgctcaagcc gatgaactgc   960
ccccaccaca tcaagattta cgcgaatgac gcccactcct accgggacct tcccgtgcgg   1020
ctggcggaat tcggcacggt gtaccgttgg gaacagagcg gagagctggg cggcatgacg   1080
cgcgtgcgcg gtttcacgca ggatgacgcc catatcttct gcacgccgga ccagcttgcc   1140
ggggaaatcc gccagtgcct gggcatcgtg aaaaccattt tcggtacgct gggcatgacg   1200
gactaccgcg tgcgcctttc catgcgcgac ccggaaagcg acaaatacgt gggttctccg   1260
gaaaattggg acaaagcgga acaggctttc cgggaagctg cggaatggct ggggggcgaac   1320
tacagcgagg aagctgggga agccgccttc tacggcccca agatcgactt catcgtgcgc   1380
gacgccatcg gccgcgaatg gcagctggga accgtgcagg tggactacaa cctgccggaa   1440
cgctttgacc tccattacac cggagcggac aacaagccgc accggcccgt gatggtgcac   1500
cgcgccccct tcggctccat ggaacgcttc acggggcttc tgattgaaca ctttgaaggc   1560
aaattcccca cctggctttc cccggaacag gtgcgcgtgc ttcccatctc cgacaaggtg   1620
acggacgtgg ccgccgcgca tcgaaccgcc ctggccgcca gaggcgtgcg cgtcacggtg   1680
gacgaaacgc cggacaaaat aggcgccaaa atccgcaatg cccgtctgga ccgcgttccc   1740
tacatgctgg tgctcggcca gcggggaggc gaagacggca ccgtctccgt ccgccaccgg   1800
gacaaggggg atctgggcgc gatgcccttt gagcaattcg cggacctcgt agcccgggaa   1860
atcgcggagc gtcatatttc tcccgtgatt tga                                1893
```

```
SEQ ID NO: 3               moltype = AA   length = 15
FEATURE                    Location/Qualifiers
REGION                     1..15
                           note = Functional region 1(99~113)
source                     1..15
                           mol_type = protein
                           organism = unidentified
SEQUENCE: 3
AESGELGALG PRSEP                                                        15

SEQ ID NO: 4               moltype = AA   length = 23
FEATURE                    Location/Qualifiers
REGION                     1..23
                           note = Functional region 2(290~312)
source                     1..23
                           mol_type = protein
                           organism = unidentified
SEQUENCE: 4
KLSQEGASCA ELFNGLATGT IEG                                               23

SEQ ID NO: 5               moltype = DNA   length = 45
FEATURE                    Location/Qualifiers
misc_feature               1..45
                           note = Functional region 1(295-339)
source                     1..45
                           mol_type = other DNA
                           organism = unidentified
SEQUENCE: 5
gcggaatccg gggagctggg cgccctgggc ccccgcagcg agcct                      45

SEQ ID NO: 6               moltype = DNA   length = 69
FEATURE                    Location/Qualifiers
misc_feature               1..69
                           note = Functional region 2(868-936)
source                     1..69
                           mol_type = other DNA
                           organism = unidentified
SEQUENCE: 6
aaactcagcc aggaggggggc ttcctgcgcg gaactgttca acggcctggc caccggcacc   60
attgagggc                                                              69

SEQ ID NO: 7               moltype = DNA   length = 1848
FEATURE                    Location/Qualifiers
misc_feature               1..1848
                           note = Akkermansia muciniphila TARS_del_Functional region 1
source                     1..1848
                           mol_type = other DNA
                           organism = synthetic construct
SEQUENCE: 7
atgtccgaac acaaggaaag aaagactctt gaagaacgcc aacagatgtc tgatctggaa   60
cggctgcgcc actcctgcgc gcacgttctg gctacggcca tttgccgcct ctggccggat   120
gcccagctgg ccggcggggcc tgccgtggat aacggttttt attacgacgt ggagctggac   180
caccgcatca gcacagagga tttttgaacgc attgaggagg agataggaaaa agtggtgaag   240
gaaaaccagg ttttccagaa ggaagtcatt tcccgcgcgg atgccatgaa gatgtcccgc   300
ttcaagattg acctgctgaa cgacatcccg gaagacgagg agatttccct ctaccgcaac   360
ggggatttta cggacttgtg cgccggtccc cacgtgggcc gcacgggcaa ctgcaaggca   420
ttcaaaatca tgagcgtggc gagcgccttc tacaaggggg acaaaaaccg ccccatgctc   480
cagcgcattt acggcacctg cttcccgaac cgcacccagc ttgacgaaca cctggaacgg   540
```

-continued

```
ctggaagagg cgcggcgccg cgaccaccgc aaactgggcc gcgaactggg cctgttctgc    600
attgacgaat ccgtggggca ggggctcatc ctctggaagc ccaaggggggc tctcatccgc   660
cgttccctgc aggacttcat cacggaagag ctggacaagc tgggctactc ccaggtgtac    720
acgcccaaca tcggcaagct ggacctgtac cgcacgtccg gacacttccc gtattatcag    780
gaaagccagt acgcgcccat cccagaacgg gacgccatgg aaaaactcag ccaggagggg    840
gcttcctgcg cggaactgtt caacggcctg gccaccggca ccattgaggg ctatatgctc    900
aagccgatga actgccccca ccacatcaag atttacgcga atgacgccca ctcctaccgg    960
gaccttcccg tgcggctggc ggaattcggc acggtgtacc gttgggaaca gagcggagag    1020
ctgggcgcgg tgacgcgcgt gcgcggtttc acgcaggatg acgcccatat cttctgcacg    1080
ccggaccagc ttgccgggga aatccgccag tgcctgggca tcgtgaaaac cattttcggt    1140
acgctgggca tgacggacta ccgcgtgcgc ctttccatgc gcgacccgga aagcgacaaa    1200
tacgtgggtt ctccggaaaa ttgggacaaa gcggaacagg ctctgcggga agctgcggaa    1260
tggctggggg cggactacag cgaggaagct ggggaagccg ccttctacgg ccccaagatc    1320
gacttcatcg tgcgcgacgc catcggccgg gaatggcagc tgggaaccgt gcaggtgac    1380
tacaacctgc cggaacgctt tgacctccat tacaccggag cggacaacaa gccgcaccgg    1440
cccgtgatgg tgcaccgcgc cccttcggc tccatggaac gcttcacggg gcttctgatt    1500
gaacactttg aaggcaaatt ccccacctgg ctttccccgg aacaggtgcg cgtgcttccc    1560
atctccgaca aggtgacgga cgtggccgcc gcgcatcgaa cgccctgcc gccagaggc    1620
gtgcgcgtca cggtggacga aacgccggac aaaataggcg ccaaaatccg caatgcccgt    1680
ctggaccgcg ttccctacat gctggtgctc ggccagcggg aggcggaaga cggcaccgtc    1740
tccgtccgcc accgggacaa ggggggatctg ggcgcgatgc cctttgagca attcgcggac    1800
ctcgtagccc gggaaatcgc ggagcgtcat atttctcccg tgatttga                 1848
```

```
SEQ ID NO: 8              moltype = DNA  length = 1824
FEATURE                   Location/Qualifiers
misc_feature              1..1824
                          note = Akkermansia muciniphila TARS_del_Functional region 2
source                    1..1824
                          mol_type = other DNA
                          organism = synthetic construct
SEQUENCE: 8
atgtccgaac acaaggaaag aaagactctt gaagaacgcc aacagatgtc tgatctggaa    60
cggctgcgcc actcctgcgc gcacgttctg gctacggcca tttgccgcct ctggccggat    120
gcccagctgg ccggcgggcc tgccgtggat aacggttttt attacgacgt ggagctggac    180
caccgcatca gcacagagga ttttgaacgc attgaggagg agatgaaaaa agtggtgaag    240
gaaaaccagg ttttccagaa ggaagtcatt tcccgcgcgg atgccatgaa gatggcggaa    300
tccgggggagc tgggcgccct gggcccccgc agcgagcctt cccgcttcaa gattgacctg    360
ctgaacgaca tcccggaaga cgaggagatt tccctctacc gcaacgggga tttttacggac    420
ttgtgcgccg gtcccacgt gggccgcacg ggcaactgca aggcattcaa aatcatgagc    480
gtggcgagcg ccttctacaa gggggacaaa aaccgcccca tgctccagcg catttacggc    540
acctgcttcc cgaaccgcac ccagcttgac gaacacctgg aacggctgga agaggcgcgg    600
cgccgcgacc accgcaaact gggccgcgaa ctgggcctgt tctgcattga cgaatccgtg    660
gggcaggggc tcatcctctg gaagcccaag ggggctctca tccgccggac cctggc        720
ttcatcacgg aagagctgga caagctgggc tactcccagg tgtacacgcc caacatcggc    780
aagctggacc tgtaccgcac gtccggacac ttcccgtatt atcaggaaag ccagtacgcg    840
cccatccag aacgggacgc catggaatat atgctcaagc cgatgaactg cccccaccac    900
atcaagattt acgcgaatga cgcccactcc taccgggacc ttccgtgcg gctggcggaa    960
ttcggcacgg tgtaccgttg ggaacagagc ggagagctgg gcgggcatgac gcgcgtgcgc    1020
ggtttcacgc aggatgacgc ccatatcttc tgcacgccgg accagcttgc cggggaaatc    1080
cgccagtgcc tgggcatcgt gaaaaccatt ttcggtacgc tgggcatgac ggactaccgc    1140
gtgcgccttt ccatgcgcga cccggaaagc gacaaatacg tgggttctcc ggaaaattg     1200
gacaaagcgg aacaggctct gcgggaagct gcggaatggc tggggcggga ctacagcgag    1260
gaagctgggg aagccgcctt ctacggcccc aagatcgact tcatcgtgcg cgacgccatc    1320
ggccgcgaat ggcagctggg aaccgtgcag gtggactaca acctgccgga acgctttgac    1380
ctccattaca ccggagcgga caacaagccg caccggcccg tgatggtgca ccgcgcccct    1440
ttcggctcca tggaacgctt cacggggctt ctgattgaac actttgaagg caaattcccc    1500
acctggcttt ccccggaaca ggtgcgcgtg cttcccatct ccgacaaggt gacggacgtg    1560
gccgccgcgc atcgaaccgc cctggccgcc agaggcgtgc gcgtcacggt ggacgaaacg    1620
ccggacaaaa taggcgccaa aatccgcaat gcccgtctgg accgcgttcc ctacatgctg    1680
gtgctcggcc agcggggagc ggaagacggc accgtctccg tccgccaccg ggacaagggg    1740
gatctgggcg cgatgccctt tgagcaattc gcggacctcg tagcccggga aatcgcggag    1800
cgtcatattt ctcccgtgat ttga                                           1824
```

```
SEQ ID NO: 9              moltype = DNA  length = 1779
FEATURE                   Location/Qualifiers
misc_feature              1..1779
                          note = Akkermansia muciniphila TARS_del_Functional region
                          1_Functional region 2
source                    1..1779
                          mol_type = other DNA
                          organism = synthetic construct
SEQUENCE: 9
atgtccgaac acaaggaaag aaagactctt gaagaacgcc aacagatgtc tgatctggaa    60
cggctgcgcc actcctgcgc gcacgttctg gctacggcca tttgccgcct ctggccggat    120
gcccagctgg ccggcgggcc tgccgtggat aacggttttt attacgacgt ggagctggac    180
caccgcatca gcacagagga ttttgaacgc attgaggagg agatgaaaaa agtggtgaag    240
gaaaaccagg ttttccagaa ggaagtcatt tcccgcgcgg atgccatgaa gatgtcccgc    300
ttcaagattg acctgctgaa cgacatcccg gaagacgagg agatttccct ctaccgcaac    360
gggggatttta cggacttgtg cgccggtccc cacgtgggcc gcacgggcaa ctgcaaggca    420
```

```
ttcaaaatca tgagcgtggc gagcgccttc tacaaggggg acaaaaaccg ccccatgctc    480
cagcgcattt acggcacctg cttcccgaac cgcacccagc ttgacgaaca cctgggaacgg    540
ctggaagagg cgcggcgccg cgaccaccgc aaactgggcc gcgaactggg cctgttctgc    600
attgacgaat ccgtggggca ggggctcatc ctctggaagc ccaagggggc tctcatccgc    660
cgttccctgc aggacttcat cacggaagag ctggacaagc tgggctactc ccaggtgtac    720
acgcccaaca tcggcaagct ggacctgtac cgcacgtccg gacacttccc gtattatcag    780
gaaagccagt acgcgcccat cccagaacgg gacgccatgg aatatatgct caagccgatg    840
aactgccccc accacatcaa gatttacgcg aatgacgccc actcctaccg ggaccttccc    900
gtgcggctgg cggaattcgg cacggtgtac cgttgggaac agagcggaga gctgggcggc    960
atgacgcgcg tgcgcggttt cacgcaggat gacgcccata tcttctgcac gccggaccag    1020
cttgccgggg aaatccgcca gtgcctgggc atcgtgaaaa ccattttcgg tacgctgggc    1080
atgacggact accgcgtgcg cctttccatg cgcgacccgg aaagcgacaa atacgtgggt    1140
tctccggaaa attgggacaa agcggaacag gctctgcggg aagctgcgga atggctgggg    1200
gcggactaca gcgaggaagc tggggaagcc gccttctacg cccccaagat cgacttcatc    1260
gtgcgcgacg ccatcggccg cgaatgcag ctgggaaccg tgcaggtgga ctacaacctg    1320
ccggaacgct ttgacctcca ttacaccgga gcggacaaca agccgcaccg gcccgtgatg    1380
gtgcaccgcg ccccccttcg gctccatgga cgcttcacgg ggcttctgat tgaacacttt    1440
gaaggcaaat tccccacctg gctttccccg gaacaggtgc gcgtgcttcc catctccgac    1500
aaggtgacgg acgtggccgc cgcgcatcga accgccctgg ccgccagagg cgtgcgcgtc    1560
acggtggacg aaacgccgga caaaataggc gccaaaatcc gcaatgcccg tctggaccgc    1620
gttccctaca tgctggtgct cggccagcgg gaggcggaag acggcaccgt ctccgtccgc    1680
caccgggaca aggggggatct gggcgcgatg cccctttgagc aattcgcgga cctcgtagcc    1740
cgggaaatcg cggagcgtca tatttctccc gtgatttga    1779

SEQ ID NO: 10       moltype = DNA  length = 1182
FEATURE             Location/Qualifiers
misc_feature        1..1182
                    note = Akkermansia muciniphila YARS
source              1..1182
                    mol_type = other DNA
                    organism = unidentified
SEQUENCE: 10
atgactatag atgagcaatt agacatattg atgggcggta ccgccgtcgt gatcagccgc    60
gaagagctga aggagcgtct caagctgggc cgccccctgc gcgtgaagct gggcgtggac    120
cctactgcgc cggacatcca cctgggccat accgtgcgta ttgagaaatt gggccagttc    180
caggaacttg gccaccaggc tgtttttgctc atcggggatt tcaccgccac gatcggcgac    240
ccttccggcc gttccgtgac ccgcccccccc ctttcccgtg aacaggtgct ggagaatgcg    300
gagacatata ccaagcaggc gttcaagatt ctggaccgtg acaagacgga gatcgtgtat    360
aatgggact ggttccgcaa gatgacgtat gaggaggtgc tgaagcttaa ttcccgcgtg    420
accatgcagc agatgctggc ccgggaggat ttcaaggccc gtgtggaggg aggtaaggag    480
gtgcgcctgc atgagatgca gtatccgatt atgcagggct gggattccgt ggaaatccgt    540
gcggacgtgg aactgggcgg gacggaccag cttttcaaca tcctggtggg ccgcgacctt    600
cagaaggagg aaggcatgtt gccgcagatc gccatgacga tgcctcttct ggaaggtctg    660
gacggcgttc ggaagatgtc caagtcctac gggaattacg tgggcgtgga tgagtctccg    720
gagatgatgt tcggcaagat gatgagcgcc agcgacgaac tgatggaccg ttattacctg    780
gtgctgctgt gtgagaagcg ggacatggga ttgcatccga tggaagccaa aaagctcctg    840
gcctggaaaa tcacggcacg ctatcatgat tccgccgcg cggatgccgc gcgttctgac    900
tgggaaaccc gttttttccaa gagggatttg gctgccgcgg atttgccgga agtggagatt    960
gcctccctgc ctgccgacat gaatgccctg gccctggttt ccttcctgtt tgagaatgtt    1020
ttccaggtga aaaaatccaa tggcgttctc cgcaaggagc atttcacgcc cggcgctatc    1080
cagttgaatg atgtgaaaat gacagacccc tccgccgttt tggaactggc tccgggcagc    1140
atcctgcgcc tgagcaagaa gcatgctgtg cgtttcaaat ag    1182

SEQ ID NO: 11       moltype = DNA  length = 1521
FEATURE             Location/Qualifiers
misc_feature        1..1521
                    note = Akkermansia muciniphila PARS
source              1..1521
                    mol_type = other DNA
                    organism = unidentified
SEQUENCE: 11
atgtctcagc aaaccgcaat caccctacc cgcgcccagg atttccccga gtggtaccag    60
caagtcatca aggccgccga catggcggaa aattccgagg tccgcggctg catggtcatc    120
aagccatggg gctacgccat ttgggaactc attcaaaagg acctggacca gcgcttcaag    180
gacaccggcc atacgaacgc ctatttcccc ctcctgattc ctatctccta tctgaaaag    240
gaagcggagc atgctgaagg cttcgccacg gaatgcgccg tagtcaccca ccacaggctg    300
gaagcgcaaa aggatgaagc caccggcaag acacgcatga ttcccaccgg ggagcttacg    360
gaacccttcg tcatccggcc cacctcggaa accgtcatcg gcgcggcttt cgccgcctgg    420
acctccagtt accgggacct gcccctcaaa gtcaaccagt ggtgcaacgt gatgcgctag    480
gaaatgaggc cccgaatctt cctgcgcacg gcggaattcc tgtggcagga agggcatacg    540
gcccatgaaa cccgcgagga agccattgag gaaaccctca ccatgcacaa ggtttatgaa    600
gaattccagc gggacgtgct cgccatcccc accattccag gggaaaagac ggaggcggaa    660
cgcttccccg gagcggaaca aacctacacg gtggaagcca tggtgcagga ccgcaaggcc    720
atccaggcag ggacctccca cttcctgggg cagaatttct ccaagtccca gaacatctga    780
ttcgccggaa gggacaacac ccagcaattc gcatggacaa gctcctgggg cgttccacc    840
cgcatgatcg gagcgctcat catgatgcac tccgacgacg acggactcgt ctgcccgccc    900
cgcgtcgctc cccagcaaat cgtcatcatt cccgtcacgc ccaaggaaga aagccggccag    960
gccgttctgc accactgcga ggaactggcg cgcaccctcc gcgccaaaac cttccacggc    1020
cagccgctgc gcgtgctggt ggacaggcgc gacctgggcg gcggcgccaa gaaatgggaa    1080
```

-continued

```
tgggtgaaaa aaggcgtgcc cgtgcgtctg gaaataggcc cccgggacct ggaaaaaggc    1140
tccgtctgcc ttcagcggcg cgaccggccc gccaatgaaa aatccttcgt cccggaaacg    1200
gaactgatcg ataccgctgc ggatattctc caaagcatcc aggacaccct gcttcagcgg    1260
gccattgcct tccgggactc ccatatccgc cccgcctcca ctctgcggga attggaagaa    1320
aacttctccg gagagggaga tgcagattgg ctccaggtgc cgtgggacgg gtctccggaa    1380
gaagaagaag aactggctaa acggctgcgc atttccatcc gctgcatccc gctcggcgag    1440
ctgggccgcg gcgaaccggc accctgcatc ctcaccggac gtatgacgaa acgccgtgtt    1500
ctctgggcca gaagctactg a                                             1521
```

SEQ ID NO: 12            moltype = DNA  length = 1026
FEATURE                  Location/Qualifiers
misc_feature             1..1026
                         note = Akkermansia muciniphila GAPDH
source                   1..1026
                         mol_type = other DNA
                         organism = unidentified
SEQUENCE: 12

```
atggccaaat acgctattaa cggttttgga cgcattggtc gcaacgtact gcgcgccatg    60
tccaaggaag aacgcaacaa ggttgttgcc atcaatgacc tgactcctat cgaaacgatc    120
gcccacctgc tcaagtatga ctccacgcag ggcaagtttg acggtgaaat ttccatcgag    180
ggtgattatc tggtcgttga cggtcacaag atcctcatca ccgtgaaacg tgatcccgcc    240
aaccttccct ggaaggatct gggcgtggac gtcgttctgg aatccaccgg cctgttcacc    300
aagcgcgacg ccgccaagga gcaccttgac gccggcgcca agaaggttct tatttccgct    360
ccctccccgg atccggacct gactttcgtt ctgggcatca acgacagcga atacgatcct    420
gccaagcacg atatcgtttc caacgcttcc tgcaccacca actgccttgc tccgatggtg    480
aaggtgctgg acgacaagtt cggcgttgaa aagggcatga tgagcacgat tcactcctac    540
acgaacgacc agcgcattct ggaccttccg cacaaggatc cccgccgtgc ccgcgccgcc    600
gcgatcaaca tcattccgac gaccaccggc gccgccaagg ccattggtga gtaatgccg    660
aacctgaagg gttccctgaa cggcgcttcc ttccgcgttc cgactccgac cggttccctg    720
accgactttg tggccgtgct caagaaggat gtgaccgtgg aagaagtaaa cgccgccatg    780
aaggaagccg ctgaaggccc gctgaaggcc attctggctt actccgaaga agcgctcgtt    840
cttcaggaca tcgtttccga cccccactcc tgcatctttg actccggctt cacgtatgtg    900
gtcggcggca acctggtgaa ggtctgcggc tggtacgaca cgaatgggg ttactccaac    960
cgcgccgccc aggccatgaa gaagctgggc gacagcctgg gctgcggatg ctcctgcggc    1020
aagtaa                                                             1026
```

SEQ ID NO: 13            moltype = DNA  length = 1941
FEATURE                  Location/Qualifiers
misc_feature             1..1941
                         note = Bacteroides fragilis TARS
source                   1..1941
                         mol_type = other DNA
                         organism = unidentified
SEQUENCE: 13

```
atgataaaaa taacatttcc tgatggctct gttcgtgagt ataacgaagg agtaaacgga    60
ctgcaaattg cagaaagtat cagttcgcgt ttggcgcaag acgtactggc gtgcggagtg    120
aacggtgaga tttatgattt aggacgtccc atcaatgaag atgcttcggt agtactctat    180
aagtgggaag atgaacaggg aaaagcatgct ttctggcaca cgagtgccca cttgctggct    240
gaagctttac aggaactgta tccgggcatt cagtttggta tcggtccggc tattgaaaac    300
ggtttctact atgatgttga tccggagag gcggtcatca aagaggctga tctgcctgct    360
attgaagcga agatggctga gttggttgca aagaaagagg ctgtcgtgcg tcgggatatt    420
gcaaaaggcg atgctttaaa gatgtttggc gaccgtggag aaacatataa atgtgagctg    480
atttccgaat ggaagacggg acatataact acatatacac aaggtgattt tacggatctt    540
tgccgtggtc ctcacttgat gacaactgct cctattaagg cgataaagct gacttctgtg    600
gcaggagctt actggcgtgg ccatgaagat cgtaagatgc tgacccgtat atatggtatc    660
actttcccga aaagaagat gctggatgag tatctggctt taatggaaga agctaaaaaa    720
cgcgaccatc gtaaaattgg taaggagatg cagttgttca tgttctctga tacggtgggt    780
aaaggattgc ctatgtggtt gccgaaaggt actgctttgc gtttgcgctt acaggacttc    840
ttgcgccgta tacagactcg ttatgactat caggaggtga ttactccgcc tatcggtaac    900
aagctgctgt atgtgacttc gggacattat gcgaaaatatg gtaaagatgc attccagccc    960
atccatacac cggaagaggg tgaagagtac ttcctgaagc cgatgaactg tcctcatcat    1020
tgtgaaattt ataagaattt cccgcgttcg tataaggatt gcctttacg tattgccgaa    1080
ttcggaactg tttgtcggta cgagcagagt ggtgagcttc acgggttgac tcgtgtgcgt    1140
agttttactc aggatgatgc acatattttc tgtcgtccgg atcaggtgga gggagaattc    1200
ctccgtgtaa tggacattat ttcgattgtg ttccgttcta tggatttcga taacttcgaa    1260
gcacagattt ctttacgcga taaagtgaat cgtgaaaaat atatcggtag tgatgaaaac    1320
tgggaaaaag ccgagcaggc cattattgaa gcatgtgagg aaaaaggatt gaaggcaaag    1380
atagaatatg gtgaagctgc tttctatggc cctaaattgg attttatggt gaaagatgcc    1440
atcggtcgcc gctggcagtt aggtactatc caggttgact ataatttgcc ggagcgcttc    1500
gaactggaat atatgggatc ggataatcag aaacaccgtc cggtaatgat tcaccgtgct    1560
ccgtttggat ctatggaacg ctttgtcgct gtattgattg agcatactgc cggtaaattc    1620
ccgttgtggt tgactccgga acaggtagtt attctcccga ttagtgaaaa attcaacgaa    1680
tatgcagaga aagtgaaaac ttatctgaag atgaaggaaa ttcgtgctat tgtagatgat    1740
cgtaatgaaa aaatcggcg taagatacgc gacaatgaga tgaaacgtat tccgtatatg    1800
ctgattgtcg gtgagaaaga agccgaaaat ggggaagttt ctgttcgtcg acagggcgaa    1860
ggggacaaag gaaccatgaa atttgaagaa tttggtgaaa ttttgaacga agaagttcag    1920
aatatgataa ataaatggta a                                           1941
```

SEQ ID NO: 14            moltype = DNA  length = 1929

-continued

```
FEATURE              Location/Qualifiers
misc_feature         1..1929
                     note = Escherichia coli TARS
source               1..1929
                     mol_type = other DNA
                     organism = unidentified
SEQUENCE: 14
atgcctgtta taactcttcc tgatggcagc caacgccatt acgatcacgc tgtaagcccc   60
atggatgttg cgctggacat tggtccaggt ctggcgaaag cctgtatcgc agggcgcgtt  120
aatggcgaac tggttgatgc ttgcgatctg attgaaaacg acgcacaact gtcgatcatt  180
accgccaaag acgaagaagg tctggagatc attcgtcact cctgtgcgca cctgttaggg  240
cacgcgatta aacaactttg gccgcatacc aaaatggcaa tcggcccggt tattgacaac  300
ggttttttatt acgacgttga tcttgaccgc acgttaaccc aggaagatgt cgaagcactc  360
gagaagcgga tgcatgagct tgctgagaaa aactacgacg tcattaagaa gaaagtcagc  420
tggcacgaag cgcgtgaaac tttcgccaac cgtggggaga gctacaaagt ctccattctt  480
gacgaaaaca tcgcccatga tgacaagcca ggtctgtact tccatgaaga atatgtcgat  540
atgtgccgcg gtccgcacgt accgaacatg cgtttctgcc atcatttcaa actaatgaaa  600
acggcagggg cttactggcg tggcgacagc aacaacaaaa tgttgcaacg tatttacggt  660
acggcgtggg cagacaaaaa agcacttaac gcttacctgc agcgcctgga agaagccgcg  720
aaacgcgacc accgtaaaat cggtaaacag ctcgacctgt accatatgca ggaagaagcg  780
ccgggtatgg tattctggca caacgacggc tggaccatct tccgtgaact ggaagtgttt  840
gttcgttcta aactgaaaga gtaccagtat caggaagtta aagtccgtt catgatggac  900
cgtgtcctgt gggaaaaaac cggtcactgg gacaactaca aagatgcaat gttcaccaca  960
tcttctgaga accgtgaata ctgcattaag ccgatgaact gcccgggtca cgtacaaatt 1020
ttcaaccagg ggctgaagtc ttatcgcgat ctgccgctgc gtatggccga gtttggtagc 1080
tgccaccgta acgagccgtc aggttcgctg catggcctga tgcgcgtgcg tggatttacc 1140
caggatgacg cgcatatctt ctgtactgaa gaacaaattc gcgatgaagt taacggatgt 1200
atccgtttag tctatgatat gtacagcact tttggcttcg agaagatcgt cgtcaaactc 1260
tccactcgtc ctgaaaaacg tattggcagc gacgaaatgt gggatcgtgc tgaggcggac 1320
ctggcggttg cgctggaaga aaacaacatc ccgtttgaat atcaactggg tgaaggcgct 1380
ttctacggtc cgaaaattga atttaccctg tatgactgcc tcgatcgtgc atggcagtgc 1440
ggtacagtac agctggactt ctctttgccg tctcgtctga gcgcttctta tgtaggcgaa 1500
gacaatgaac gtaaagtacc ggtaatgatt caccgcgcaa ttctggggtc gatggaacgt 1560
ttcatcggta tcctgaccga agagttcgct ggtttcttcc cgacctggct tgcgccggtt 1620
caggttgtta tcatgaatat taccgattca cagtctgaat acgttaacga attgacgcaa 1680
aaactatcaa atgcgggcat tcgtgttaaa gcagacttga gaaatgagaa gattggcttt 1740
aaaatccgcg agcacacttt gcgtcgcgtc ccatatatgc tggtctgtgg tgataaaagag 1800
gtggaatcag gcaaagttgc cgttcgcacc cgccgtggta aagacctggg aagcatggac 1860
gtaaatgaag tgatcgagaa gctgcaacaa gagattcgca gccgcagtct taaacaattg 1920
gaggaataa                                                        1929

SEQ ID NO: 15         moltype = DNA  length = 1947
FEATURE              Location/Qualifiers
misc_feature         1..1947
                     note = Ruminococcus brommi TARS
source               1..1947
                     mol_type = other DNA
                     organism = unidentified
SEQUENCE: 15
atgattaatg ttgaattaaa aggcggagca gtcaaggaat ttgaaaacgg tacaactcct   60
gccgaaattg caaatcaat cggtgcaggc ttgtacaagt ctgtttgctg tgcaaaggtt  120
gacggcgacc tttgtgacct cagaacaccg cttgaaaaag attgtaaggt tgaacttctc  180
acatttgata atgttgacgg tcagaaaact ttctggcaca cagcctctca tgttcttgct  240
caggcagtaa aaagacttta tccgaatgca aagtgtgcaa tcggtcctgc cgttgacaac  300
ggtttttact atgattttga tgttgaaaag cctttctcac gcgaagacct tgaaaaaatc  360
aaggctgaga tgaagaaaat cgtaaaatcg ggtcttgagc ttgaaagagt tgagctttct  420
cccgaggagg ctgaaaagaa acttgaagag atgaacgagc cttacaaggt tgaacttgtt  480
aaggaacatt ccgacaaggg cgagcatatc acattctata aacagggtga gtttatcgac  540
ctctgcgcag gtcctcatct catgagtgtt gcaccgatca aggctattga actcactgcc  600
tgcacaggcg cttactggag aggtgacgca aacaacgcac agctttgccg tgtttacggt  660
gtagctttcc caaaggcatc aatgcttgaa gaacacctca aaaagcttga agaagcaaag  720
cttcgtgacc acaacaagct cggccgtgaa cttgaatact ttacaactgt tgactatgtc  780
ggtcagggac ttcctattct tcttccaaag ggtgcaagag ttgttcagct tttacagaga  840
tgggttgaag atgttgagca gtcaaagggc tgtcttcttg caaaaactcc tcttcttgca  900
aagagagatc tttataagat ttcaggtcac tgggatcatt atcttgacgg tatgtttgta  960
ctcggcgatc cgcatgatga agaaaaggaa tgcttcgcac ttcgtcctat gacttgcccg 1020
ttccagtatc aggtttatct taacaaacag cgttcatatc gtgaccttcc gatgcgtctt 1080
acggaaacat caacacttt ccgtaacgag gcaagcggtg agatgcacgg tcttatccgt 1140
gttcgtcagt tcacaatttc agaaggacac tacattctcc gtcccgatca gcttgaacag 1200
gaattcaagg gttgtcttga gcttgctaaa tatttccttg cacggtagg acttcttgaa 1260
aactgtactt tcagattctc acagtgggat cctgaaaaca agaataataa gtatgagggt 1320
acaaaggaac agtgggaaga gtcacaggct gttatgaaaa ctattctcga tgaccttgat 1380
gttgactatg agattggtat tgacgaggcc gcattctacg gtccgaagct tgatattcag 1440
tacaagaatg tattcggtaa gaagacaca attgttacaa tccagattga tatgctcctt 1500
gccgaaagat tcggtatgta ctacatcgac aaggacggtc agaagaagct tccgtatatt 1560
attcacagaa cttcactcgg ttgctttgaa agaactcttg catatatgat tgagagattt 1620
gccggtgtaa tgccgctttg gcttgctccc gagcagatca gacttcttcc gataaaagag 1680
ggtaatgttg agtatgcaca gggtattgca gacagactta cttcactcgg tatgagagtt 1740
actgttgaca gcagagatga aaacatcggt ccaaagatta aggctgcaag acttgaaaga 1800
```

-continued

```
attccgtata ttcttgtaat cggcgcacaac gagatgaatt catcaacagt tacggttcgt   1860
tcaagaaaaa gaggagaaat cccgaatatg cccgttgacg agtttgttgc tcttgttaag   1920
aacgaagtag atacaaagga aaaataa                                        1947

SEQ ID NO: 16            moltype = DNA   length = 2175
FEATURE                  Location/Qualifiers
misc_feature             1..2175
                         note = Homo sapiens TARS
source                   1..2175
                         mol_type = other DNA
                         organism = unidentified
SEQUENCE: 16
atgtttgagg agaaggccag cagtccttca gggaagatgg gaggcgagga gaagccgatt    60
ggtgctggtg aagagaagca aaaggaagga ggcaaaaga agaacaaaga aggatctgga    120
gatgggaggtc gagctgagtt gaatcctgg cctgaatata tttacacacg tcttgagatg   180
tataatatac taaaagcaga acatgattcc attctggcag aaaaggcaga aaagatagc    240
aagccaatta aagtcacttt gcctgatggt aaacaggttg atgcggaatc ttggaaaact    300
acaccatatc aaattgcctg tggaattagt caaggcctgg ccgacaacac cgttattgct    360
aaagtaaata atgttgtgtg ggacctggac cgccctctgg aagaagattg taccttggag    420
cttctcaagt ttgaggatga ggaagctcag gcagtgtatt ggcactctag tgctcacata    480
atgggtgaag ccatggaaag agtctatggt ggatgtttat gctacggtcc gccaatagaa    540
aatggattct attatgacat gtacctcgaa gaaggggtg tgtctagcaa tgatttctct    600
tctctggagg ctttgtgtaa gaaaatcatt aaagaaaaac aagcttttga aagactggaa    660
gttaagaaag aaactttact ggcaatgttt aagtacaaca agttcaaatg ccggatattg    720
aatgaaaagg tgaatactcc aactaccaca gtctatagat gtggcccttt gatagatctc    780
tgccgggggtc ctcatgttag acacacgggc aaaattaagg ctttaaaaat acacaaaaat    840
tcctccacgt actgggaagg caaagcagat atggagactc tccagagaat ttatggcatt    900
tcattcccag atcctaaaat gttgaaagag tgggagaagt tccaagagga agctaaaaac    960
cgagatcata ggaaaattgg cagggaccaa gaactatatt tctttcatga actcagccct   1020
ggaagttgct tttttctgcc aaaaggagcc tacatttata atgcacttat tgaattcatt   1080
aggagcgaat ataggaaaag aggattccga gaggtagtca ccccaaacat cttcaacagc   1140
cgactctgga tgacctcggg ccactggcag cactacagcg agaacatgtt ctcctttgag   1200
gtggagaagg agctgtttgc cctgaaaccc atgaactgcc caggacactg ccttatgttt   1260
gatcatcggc caaggtcctg gcgagaactg cctctgcggc tagctgattt tggggtactt   1320
cataggaacg agctgtctgg agcactcaca ggactcaccc gggtacgaag attccaacag   1380
gatgatgctc acatattctg tgccatggag cagattgaag atgaaataaa aggttgtttg   1440
gattttctac gtacggtata tagcgtattt ggattttctt ttaaactaaa cctttctact   1500
cgcccggaaa aattccttgg agatatcgaa gtatgggatc aagctgagaa acaacttgaa   1560
aacagtctga atgaatttgg tgaaaagtgg gagttaaact ctggagatgg agctttctat   1620
ggcccaaaga ttgacataca gattaaagat gcgattgggc ggtaccacca gtgtgcaacc   1680
atccagctgg atttccagtt gcccatcaga tttaatctta cttatgtaag ccatgatggt   1740
gatgataaga aaaggccagt gattgttcat cgagccatct tgggatcagt ggaaagaatg   1800
attgctatcc tcacagaaaa ctatggggcc aaatggcc tt ttggctgtc ccctcgccag   1860
gtaatggtag ttccagtggg accaacctgt gatgaatatg cccaaaaggt acgacaacaa   1920
ttccacgatg ccaaattcat ggcagacatt gatctggatc caggctgtac attgaataaa   1980
aagattcgaa atgcacagtt agcacagtat aacttcattt tagttgttgg tgaaaaagag   2040
aaaatcagtg gcactgttaa tatccgcaca agagacaata aggtccacgg ggaacgcacc   2100
atttctgaaa ctatcgagcg gctacagcag ctcaaagagt tccgcagcaa acaggcagaa   2160
gaagaatttt aatga                                                     2175

SEQ ID NO: 17            moltype = DNA   length = 2433
FEATURE                  Location/Qualifiers
misc_feature             1..2433
                         note = Toll-like receptor2 (TLR2)
source                   1..2433
                         mol_type = other DNA
                         organism = unidentified
SEQUENCE: 17
atgccacata ctttgtggat ggtgtgggtc ttgggggtca tcatcagcct ctccaaggaa    60
gaatcctcca atcaggcttc tctgtcttgt gaccgcaatg gtatctgcaa gggcagctca   120
ggatctttaa actccattcc ctcagggctc acagaagctg taaaaagcct tgacctgtcc   180
aacaacagga tcacctacat tagcaacagt gacctacaga ggtgtgtgaa cctccaggct   240
ctggtgctga catccaatgg aattaacaca atagaggaag attcttttc ttccctgggc   300
agtcttgaac atttagactt atcctataat tacttatcta atttatcgtc ttcctggtca   360
aagccccttt cttctttaac attcttaaac ttactgggaa atcctacaa aaccctaggg   420
gaaacatctc ttttttctca tctcacaaaa ttgcaaatcc tgagagtggg aaatatggac   480
accttcacta agattcaaag aaaagatttt gctggactta ccttccttga ggaacttgag   540
attgatgctt cagatctaca gagctatgag ccaaaaagtt tgaagtcaat tcagaatgta   600
agtcatctga tccttcatat gaagcagcat attttactgc tggagatttt tgtagatgtt   660
acaagttccg tggaatgttt ggaactgcga gatactgatt tggacacttt ccattttttca   720
gaactatcca ctggtgaaac aaattcattg attaaaaagt ttacatttag aaatgtgaa    780
atcaccgatg aaagtttgtt tcaggttatg aaacttttga tcagatttc tggattgtta    840
gaattagagt ttgatgactg tacccttaat ggagttggta ttttagagc atctgataat    900
gacagagtta tagatccagg taaagtggaa acgttaacaa tccggagggct gcatattcca    960
aggtttttact tattttatga tctgagcact ttatattcac ttacagaaag agttaaaaga   1020
atcacagtag aaaacagtaa agttttttctg gttccttgtt tacttcaca acatttaaaa   1080
tcattagaat acttggatct cagtgaaaat ttgatggttg aagaatactt gaaaaattca   1140
gcctgtgagg atgcctggcc ctctctacaa acttaatttt taaggcaaaa tcatttggca   1200
tcattggaaa aaaccggaga gactttgctc actctgaaaa acttgactaa cattgatatc   1260
```

-continued

```
agtaagaata gttttcattc tatgcctgaa acttgtcagt ggccagaaaa gatgaaatat   1320
ttgaacttat ccagcacacg aatacacagt gtaacaggct gcattcccaa gacactggaa   1380
attttagatg ttagcaacaa caatctcaat ttattttctt tgaatttgcc gcaactcaaa   1440
gaactttata tttccagaaa taagttgatg actctaccag atgcctccct cttacccatg   1500
ttactagtat tgaaaatcag taggaatgca ataactacgt tttctaagga gcaacttgac   1560
tcatttcaca cactgaagac tttggaagct ggtggcaata acttcatttg ctcctgtgaa   1620
ttcctctcct tcactcagga gcagcaagca ctggccaaag tcttgattga ttggccagca   1680
aattacctgt gtgactctcc atcccatgtg cgtggccagc aggttcagga tgtccgcctc   1740
tcggtgtcgg aatgtcacag gacagcactg gtgtctggca tgtgctgtgc tctgttcctg   1800
ctgatcctgc tcacgggggt cctgtgccac cgtttccatg gcctgtggta tatgaaaatg   1860
atgtgggcct ggctccaggc caaaaggaag cccaggaaag ctcccagcag gaacatctgc   1920
tatgatgcat ttgtttctta cagtgagcgg gatgcctact gggtggagaa ccttatggtc   1980
caggagctgg agaacttcaa tcccccccttc aagttgtgtc ttcataagcg ggacttcatt   2040
cctggcaagt ggatcattga caatatcatt gactccattg aaaagagcca caaactgtc    2100
tttgtgcttt ctgaaaactt tgtgaagagt gagtggtgca agtatgaact ggacttctcc   2160
catttccgtc tttttgatga gaacaatgat gctgccattc tcattcttct ggagcccatt   2220
gagaaaaaag ccattcccca gcgcttctgc aagctgcgga agataatgaa caccaagacc   2280
tacctggagt ggcccatgga cgaggctcag cgggaaggat tttgggtaaa tctgagagct   2340
gcgataaagt cctaggttcc catatttaag accagtcttt gtctagttgg gatctttatg   2400
tcactagtta tagttaagtt cattcagaca taa                                2433
```

```
SEQ ID NO: 18          moltype = AA  length = 680
FEATURE                Location/Qualifiers
REGION                 1..680
                       note = EcTARS(U1/U2)
source                 1..680
                       mol_type = protein
                       organism = synthetic construct
SEQUENCE: 18
MPVITLPDGS QRHYDHAVSP MDVALDIGPG LAKACIAGRV NGELVDACDL IENDAQLSII   60
TAKDEEGLEI IRHSCAHLLG HAIKQLWPHT KMAIGPVIDN GFYYDVDLDR TLTQEDVEAL   120
EKRMHELAEK NYDVIKKKVS WHEARETFAN RGAESGELGA LGPRSEPESY KVSILDENIA   180
HDDKPGLYFH EEYVDMCRGP HVPNMRFCHH FKLMKTAGAY WRGDSNNKML QRIYGTAWAD   240
KKALNAYLQR LEEAAKRDHR KIGKQLDLYH MQEEAPGMVF WHNDGWTIFR ELEVFVRSKL   300
KEYQYQEVKG PFMMDRVLWE KTGHWDNYKD AMFTTSSEKL SQEGASCAEL FNGLATGTIE   360
GNREYCIKPM NCPGHVQIFN QGLKSYRDLP LRMAEFGSCH RNEPSGSLHG LMRVRGFTQD   420
DAHIFCTEEQ IRDEVNGCIR LVYDMYSTFG FEKIVVKLST RPEKRIGSDE MWDRAEADLA   480
VALEENNIPF EYQLGEGAFY GPKIEFTLYD CLDRAWQCGT VQLDFSLPSR LSASYVGEDN   540
ERKVPVMIHR AILGSMERFI GILTEEFAGF FPTWLAPVQV VIMNITDSQS EYVNELTQKL   600
SNAGIRVKAD LRNEKIGFKI REHTLRRVPY MLVCGDKEVE SGKVAVRTRR GKDLGSMDVN   660
EVIEKLQQEI RSRSLKQLEE                                               680
```